(12) United States Patent
Gonzalez Rodriguez et al.

(10) Patent No.: US 9,133,200 B2
(45) Date of Patent: Sep. 15, 2015

(54) IMIDAZO[1,2-B]PYRIDAZINE AND IMIDAZO[4,5-B]PYRIDINE DERIVATIVES AS JAK INHIBITORS

(75) Inventors: Jacob Gonzalez Rodriguez, Barcelona (ES); Bernat Vidal Juan, Barcelona (ES); Laura Vidal Gispert, Barcelona (ES); Jordi Bach Taña, Barcelona (ES)

(73) Assignee: Almirall, S.A., Barcelona (ES)

( * ) Notice: Subject to any disclaimer, the term of this patent is extended or adjusted under 35 U.S.C. 154(b) by 53 days.

(21) Appl. No.: 13/988,798

(22) PCT Filed: Nov. 24, 2011

(86) PCT No.: PCT/EP2011/005929
§ 371 (c)(1),
(2), (4) Date: Aug. 13, 2013

(87) PCT Pub. No.: WO2012/069202
PCT Pub. Date: May 31, 2012

(65) Prior Publication Data
US 2013/0309200 A1    Nov. 21, 2013

Related U.S. Application Data

(60) Provisional application No. 61/436,212, filed on Jan. 26, 2011.

(30) Foreign Application Priority Data

Nov. 26, 2010    (EP) .................................... 10382318

(51) Int. Cl.
| | |
|---|---|
| C07D 487/04 | (2006.01) |
| A61K 9/20 | (2006.01) |
| A61K 9/48 | (2006.01) |
| A61K 31/437 | (2006.01) |
| A61K 31/5025 | (2006.01) |
| A61K 45/06 | (2006.01) |
| C07D 471/04 | (2006.01) |

(52) U.S. Cl.
CPC ............ *C07D 487/04* (2013.01); *A61K 9/2018* (2013.01); *A61K 9/2054* (2013.01); *A61K 9/2059* (2013.01); *A61K 9/4858* (2013.01); *A61K 31/437* (2013.01); *A61K 31/5025* (2013.01); *A61K 45/06* (2013.01); *C07D 471/04* (2013.01)

(58) Field of Classification Search
CPC . C07D 487/04; A61K 31/5025; A61K 45/06; A61K 31/437
USPC ................ 544/235, 252.05; 514/252.05, 235
See application file for complete search history.

(56) References Cited

U.S. PATENT DOCUMENTS

| | | |
|---|---|---|
| 7,074,801 B1 | 7/2006 | Yoshida et al. |
| 8,501,735 B2 | 8/2013 | Rosales et al. |
| 2013/0089512 A1 | 4/2013 | Eastwood et al. |
| 2013/0209400 A1 | 8/2013 | Tana et al. |
| 2013/0216498 A1 | 8/2013 | Eastwood et al. |
| 2014/0170110 A1 | 6/2014 | Eastwood et al. |
| 2014/0271543 A1 | 9/2014 | Eastwood et al. |

FOREIGN PATENT DOCUMENTS

| | | |
|---|---|---|
| EP | 1382603 A1 | 1/2004 |
| WO | WO 2009/106442 | 0/2009 |
| WO | WO 01/14375 A1 | 3/2001 |
| WO | WO 02/16359 A1 | 2/2002 |
| WO | WO 03/000682 A1 | 1/2003 |
| WO | WO 03/092595 A2 | 11/2003 |
| WO | WO 2005/095400 | 10/2005 |
| WO | WO 2006/038001 A1 | 4/2006 |
| WO | WO 2006/068826 A2 | 6/2006 |
| WO | WO 2007/146087 A2 | 12/2007 |
| WO | WO 2008/043031 A1 | 4/2008 |
| WO | WO 2008/045393 A2 | 4/2008 |
| WO | WO 2008/078100 A2 | 7/2008 |
| WO | WO 2008/081914 | 7/2008 |
| WO | WO 2008/118823 | 10/2008 |
| WO | WO 2009/021990 A1 | 2/2009 |
| WO | WO 2009/026254 A1 | 2/2009 |
| WO | WO 2009/050183 A2 | 4/2009 |
| WO | WO 2009/054941 | 4/2009 |
| WO | WO 2009/085913 A1 | 7/2009 |
| WO | WO 2009/086123 A1 | 7/2009 |
| WO | WO 2010/016005 A1 | 2/2010 |
| WO | WO 2010/072823 | 7/2010 |
| WO | WO 2011/076419 A1 | 6/2011 |
| WO | WO 2011/101161 A1 | 8/2011 |
| WO | WO 2011/157397 A1 | 12/2011 |
| WO | WO 2012/069202 A1 | 5/2012 |
| WO | WO 2012/160030 A1 | 11/2012 |
| WO | WO 2013/017461 | 2/2013 |

OTHER PUBLICATIONS

Vippagunta et al (2001).*

(Continued)

*Primary Examiner* — Paul V Ward
(74) *Attorney, Agent, or Firm* — Finnegan, Henderson, Farabow, Garrett & Dunner

(57) ABSTRACT

New imidazo[1,2-b]pyridazine and imidazo[4,5-b]pyridine derivatives having the chemical structure of formula (I) are disclosed; as well as process for their preparation, pharmaceutical compositions comprising them and their use in therapy as inhibitors of Janus Kinases (JAK).

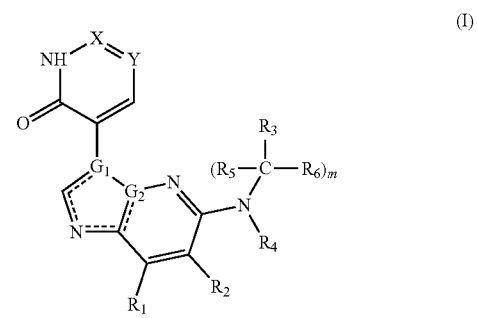

28 Claims, No Drawings

(56) References Cited

OTHER PUBLICATIONS

Atreya et al., "Blockade of Interleukin 6 trans Signaling Suppresses T-cell Resistance Against Apoptosis in Chronic Intestinal Inflammation: Evidence in Crohn Disease and Experimental Colitis in vivo," Nature Medicine, vol. 6, No. 5 (May 2000) pp. 583-588.

Baird et al., "T Cell Development and Activation in Jak3-deficient Mice, J. Leukocyte Biol.," vol. 63 (Jun. 1998) pp. 669-677.

Bright et al., "Tyrphostin B42 Inhibits IL-12-Induced Tyrosine Phosphorylation and Activation of Janus Kinase-2 and Prevents Experimental Allergic Encephalomyelitis," J. Immunol. vol. 162 (1999) pp. 6255-6262.

Briscoe et al., "Kinase-negative Mutants of JAK1 Can Sustain Interferon-?-Inducible Gene Expression But Not an Antiviral State," EMBO Journal, vol. 15, No. 4, (1996) pp. 799-809.

Buckley G. M., et al., "IRAK-4 inhibitors. Part II: A structure-based assessment of imidazo[1,2-a]pyridine binding," Bioorganic & Medicinal Chemistry Letters (2008) 18, pp. 3291-3295.

Buckley G. M., et al., "IRAK-4 inhibitors. Part III: A series of imidazo[1,2-a]pyridines," Bioorganic & Medicinal Chemistry Letters (2008) 18, pp. 3656-3660.

Chang et al., "JAK3 Inhibition Significantly Attenuates Psoriasiform Skin Inflammation in CD18 Mutant PL/J Mice," J. Immunol., vol. 183 (2009) pp. 2183-2192.

Chang et al., "JAK3 Inhibition Significantly Attenuates Psoriasiform Skin Inflammation in CD18 Mutant PL/J Mice," J. Immunol., vol. 183 (2009) Supplemental Data (3 pages).

Disanto et al., "Lymphoid Development in Mice With a Targeted Deletion of the Interleukin 2 Receptor ? Chain," PNAS, vol. 92 (Jan. 1995) pp. 377-381.

English language abstract of WO 2008/081914 A1 (2008).

Flex et al., "Somatically Acquired JAK1 Mutations in Adult Acute Lymphoblastic Leukemia," J. Exper. Med., vol. 205, No. 4 (Apr. 2008) pp. 751-758.

Grossman et al., "Dysregulated Myelopoiesis in Mice Lacking JAK3," Blood, vol. 94 (1999) pp. 932-939.

Guschin et al., "A Major Role for the Protein Tyrosine Kinase JAK1 in the JAK/STAT Signal Transduction Pathway in Response to Interleukin-6," EMBO Journal, vol. 14, No. 7 (1995) pp. 1421-1429.

Heinrich et al., "Principles of Interleukin (IL)-6-type Cytokine Signaling and Its Regulation," Biochem. J., vol. 374 (2003) pp. 1-20.

Hexner et al., "Lestaurtinib (CEP701) is a JAK2 Inhibitor That Suppresses JAK2/STAT5 Signaling and the Proliferation of Primary Erythroid Cells Form Patients With Myeloproliferative Disorders," Blood, vol. 111, No. 12, (Jun. 2008).

International Search Report of International Application No. PCT/EP2012/059394 (filed May 21, 2012), dated Jul. 6, 2012 (for 0096).

International Search Report, PCT/EP2010/007913, mailed Jun. 1, 2011.

International Search Report, PCT/EP2011/000792, mailed Jul. 21, 2011.

International Search Report, PCT/EP2011/002917, mailed Sep. 6, 2011.

Ivashkiv et al., "The JAK/STAT Pathway in Rheumatoid Arthritis: Pathogenic or Protective?" Arthritis & Rheumatism, vol. 48, No. 8 (Aug. 2003) pp. 2092-2096.

Karaghiosoff et al., "Partial Impairment of Cytokine Responses in Tyk2-Deficient Mice," Immunity, vol. 13 (Oct. 2000) pp. 549-560.

Kudlacz et al., "The JAK-3 Inhibitor CP-690550 is a Potent Anti-Inflammatory Agent in a Murine Model of Pulmonary Eosinophilia," European J. Pharmacol., vol. 582 (2008) pp. 154-161.

Lim et al., "Biologic Therapies for Inflammatory Eye Disease," Clin. Exper. Opthalmology, vol. 34 (2006) pp. 365-374.

Lovato et al., "Constitutive STAT3 Activation in Intestinal T Cells From Patients with Crohn's Disease," J. Biol. Chem., vol. 278, No. 19 (May 2003) pp. 16777-16781.

Malaviya et al., "Targeting Janus Kinase 3 in Mast Cells Prevents Immediate Hypersensitivity Reactions and Anaphylaxis," J. Biol. Chem., vol. 274, No. 38 (Sep. 1999) pp. 27028-27038.

Malaviya et al., "Treatment of Allergic Asthma by Targeting Janus Kinase 3-Dependent Leukotriene Synthesis in Mast Cells with 4-(3', 5'-Dibromo-4'-hydroxyphenyl)amino-6,7-dimethoxyquinazoline (WHI-P97)," J. Pharmacol. Exp. Ther., vol. 295, No. 3 (2000) pp. 912-926.

Manshouri et al., "The JAK Kinase Inhibitor CCP-690,550 Suppresses the Growth of Human Polycythemia Vera Cells Carrying the JAK2V617F Mutation," Cancer Sci., vol. 99, No. 6, (Jun. 2008) pp. 1265-1273.

McInnes et al., "Cytokines in the Pathogenesis of Rheumatoid Arthritis," Nature, vol. 7 (Jun. 2007) pp. 429-442.

Meydan et al., "Inhibition of Acute Lymphoblastic Leukaemia by a JAK-2 Inhibitor," Nature, vol. 379 (Feb. 1996) pp. 645-648.

Migone et al., "Constitutively Activated Jak-STAT Pathway in T Cells Transformed with HTLV-I," Science, vol. 269 (Jul. 1995) pp. 79-81.

Milici et al., "Cartilage Preservation by Inhibition of Janus Kinase 3 in Two Rodent Models of Rheumatoid Arthritis," Arthritis Research & Therapy, vol. 10, No. 1, (2008) pp. 1-9.

Minegishi et al., "Human Tyrosine Kinase 2 Deficiency Reveals Its Requisite Roles in Multiple Cytokine Signals Involved in Innate and Acquired Immunity," Immunity, vol. 25, (Nov. 2006) pp. 745-755.

Murray, Peter J., "The JAK-STAT Signaling Pathway: Input and Output Integration," J. Immunol., vol. 178 (2007) pp. 2623-2629.

Nickoloff, Brian J., "Cracking the Cytokine Code in Psoriasis," Nature Medicine, vol. 13, No. 3 (Mar. 2007) pp. 242-244.

O'Shea et al., "Jak3 and the Pathogenesis of Severe Combined Immunodeficiency," Mol. Immunol., vol. 41 (2004) pp. 727-737.

Ozaki et al., "The Control of Allergic Conjunctivitis by Suppressor of Cytokine Signaling (SOCS)3 and SOCS5 in a Murine Model," J. Immunol., vol. 175 (2005) pp. 5489-5497.

Pardanani et al., "TG101209, A Small Molecule JAK2-Selective Kinase Inhibitor Potently Inhibits Myeloproliferative Disorder-Associated JAK2V617F and MPLW515L/K Mutations," Leukemia, vol. 21, (2007) pp. 1658-1668.

Pardanani, et al., "CYT387, A Selective JAK1/JAK2 Inhibitor: in vitro Assessment of Kinase Selectivity and Preclinical Studies Using Cell Lines and Primary Cells from Polycythema Vera Patients," Leukemia, vol. 23 (2009) pp. 1441-1445.

Parganas et al., "Jak2 Is Essential for Signaling Through a Variety of Cytokine Receptors," Cell, vol. 93 (May 1998) pp. 385-395.

Park et al., "Developmental Defects of Lymphoid Cells in Jak3 Kinase-Deficient Mice," Immunity, vol. 3, (Dec. 1995) pp. 771-782.

Peschon et al., "Early Lymphocyte Expansion Is Severely Impaired in Interleukin 7 Receptor-Deficient Mice," J. Exp. Med., vol. 180 (Nov. 1994) pp. 1955-1960.

Rodig et al., "Disruption of the Jak1 Gene Demonstrates Obligatory and Nonredundant Roles of the Jaks in Cytokine-Induced Biologic Responses," Cell, vol. 93 (May 1998) pp. 373-383.

Russell et al., "Mutation of Jak3 in a Patient with SCID: Essential Role of Jak3 in Lymphoid Development," Science, vol. 270 (Nov. 1995) pp. 797-800.

Shimoda et al., "Tyk2 Plays a Restricted Role in IFNa Signaling, for IL-12-Mediated T Cell Function," Immunity, vol. 13 (Oct. 2000) pp. 561-571.

Siddiquee et al., "STAT3 as a Target for Inducing Apopotosis in Solid and Hematological Tumors," Cell Res., vol. 18, No. 2, (Feb. 2008) pp. 254-267.

Skarica et al., "Signal Transduction Inhibition of APCs Diminishes Th17 and Th1 Responses in Experimental Autoimmune Encephalomyelitis," J. Immunol., vol. 182 (2009) pp. 4192-4199.

Steinman, Lawrence, "Nuanced Roles of Cytokines in Three Major Human Brain Disorders," J. Clin. Invest., vol. 118 (2008) pp. 3557-3563.

Strober et al., "The Immunology of Mucosal Models of Inflammation," Annu. Rev. Immunol., vol. 20 (2002) pp. 495-549.

Thomis et al., "Defects in B Lymphocyte Maturation and T Lymphocyte Activation in Mice Lacking Jak3," Science, vol. 270 (Nov. 1994) pp. 794-797.

Tomita et al., "Inhibition of Constitutively Active Jak-Stat Pathway Suppresses Cell Growth of Human T-cell Leukemia Virus Type I-infected T-cell lines and Primary Adult T-cell Leukemia Cells," Retrovirology, vol. 3, No. 22 (Apr. 2006) pp. 1-10.

(56) References Cited

OTHER PUBLICATIONS

U.S. Appl. No. 13/518,863, filed Jun. 22, 2012.
U.S. Appl. No. 13/579,344, filed Aug. 16, 2012.
U.S. Appl. No. 13/704,302, filed Dec. 14, 2012.
U.S. Appl. No. 14/119,920, filed Nov. 25, 2013.
Vallochi et al., "The Role of Cytokines in the Regulation of Ocular Autoimmune Inflammation, Cytokine & Growth Factor Reviews," vol. 18 (2007) pp. 135-141.
Von Freeden-Jeffry et al., "Lymphopenia in Interleukin (IL)-7 Gene-Deleted Mice Identifies IL-7 as a Nonredundant Cytokine," J. Exp. Med., vol. 18 (Apr. 1995) pp. 1519-1526.
Wernig et al., "Efficacy of TG101348, A Selective JAK2 Inhibitor, in Treatment of a Murine Model of JAK2V617F-Induced Polycythemia Vera," Cancer Cell, vol. 13 (2008) Supplemental Data (9 pages).
Wernig et al., "Efficacy of TG101348, A Selective JAK2 Inhibitor, in Treatment of a Murine Model of JAK2V617F-Induced Polycythemia Vera," Cancer Cell, vol. 13, Part 4, (2008) pp. 311-320.
West, Kevin, "CP-690550, A JAK3 Inhibitor as an Immunosuppressant for the Treatment of Rheumatoid Arthritis, Transplant Rejection, Psoriasis and Other Immune-Mediated Disorders," Current Opinion in Investigational Drugs, vol. 10, No. 5 (2009) pp. 491-504.
Wu et al., "Design and synthesis of 3,7-diarylimidazopyridines as inhibitors of the VEGF-receptor KDR," Bioorganic & Medicinal Chemistry Letters (2004) 14, pp. 909-912.
U.S. Appl. No. 14/236,340, filed May 14, 2014.
Office Action dated Dec. 18, 2014, in U.S. Appl. No. 13/579,344.
Office Action dated Feb. 10, 2015, in U.S. Appl. No. 14/119,920.
Notice of Allowance dated Mar. 3, 2015, in U.S. Appl. No. 14/236,340.
Clinical trials, "A Open-Label Study of CP-690,550 As Long-Term Therapy (48 Weeks) in Subjects With Crohn's Disease," (NCT01470599) retrieved Sep. 17, 2014.
Clinical trials, "A Phase 3, Multi Site, Randomized, Double Bind, Placebo Controlled Study of the Efficacy and Safety Comparing CP-690,550 and Etanercept in Subjects With Moderate: To Severe Chronic Plaque Psoriasis," (NCT0141591) retrieved Sep. 17, 2014.
Clinical trials, "A Study Evaluating the Efficacy and Safety CP-690,550 in Patients with Moderate to Severe Ulcerative Colitis (OCTAVE)," Clinicaltrials.gov (NCT01465763) retrieved Sep. 17, 2014.
Clinical trials, "Effectiveness and Safety of 3 Dosing Regimens of CP-690,550 to Placebo in Subjects With Moderate to Severe Chronic Plaque Psoriasis," (NCT00678210) retrieved Sep. 17, 2014.
Clinial trials, Immunomodulatory effect of the topical ophthalmic Janus kinase inhibitor tofacitinib (CP-690,550) in patients with dry eye disease, Ophthalmology. Jul. 2012;119(7):e43-50.
Clinial trials, "Tofacitinib Ointment for Atopic Dermatitis (Atopic Eczema)," (NCT02001181) retrieved Sep. 17, 2014.
Dorwald, F. Zaragoza, Side Reactions in Organic Synthesis: A Guide to Successful Synthesis Design, Weinheim: WILEY-VCH Verlag GmbH & Co. KGaA, 2005, Preface.
International Search Report for International Application No. PCT/EP2012/064426, dated Sep. 25, 2012.
International Search Report of International Application No. PCT/EP2011/005929, dated Feb. 17, 2012.
Jordan, V. C., "Tamoxifen: A most unlikely pioneering medicine," Nature Reviews: Drug Discovery, 2, 2003, 205-213.
Lucet, Isabel, et al, "The structural basis of Janus kinase 2 inhibition by a potent and specific pan-janus kinase inhibitor." Blood. (2006), vol. 107, No. 1, pp. 176-183.
Mandal, A. "Cancer Classification."© 2014 Available from <http://www.news-medical.net/health/Cancer-Classification.aspx.
MD Anderson Cancer Center, "Myeloproliferative Disease Prevention and Screening." (c) 2014.
Office Action (Restriction Requirement) dated Mar. 11, 2014. in U.S. Appl. No. 13/704,302.
Office Action (Restriction Requirement) dated Oct. 10, 2013, in U.S. Appl. No. 13/518,853.
Office Action (Restriction Requirement) dated Oct. 24, 2013, in U.S. Appl. No. 13/579,344.
Office Action (Restriction Requirement) dated Sep. 29, 2014, in U.S. Appl. No. 14/119,920.
Office Action dated Jan. 8, 2014, in U.S. Appl. No. 13/579,344.
Office Action dated Jun. 20, 2014, in U.S. Appl. No. 13/579,344.
Office Action dated May 22, 2014, in U.S. Appl. No. 13/518,863.
Office Action (Restriction Requirement) dated Nov. 13, 2014, in U.S Appl. No. 13/988,798.
Oxford Dictionary of Biochemistry and Molecular Biology, 1997, Oxford University Press, pp. 314-315.
Parks, Deborah L. "Tofacitinib and Other Kinase inhibitors Offer New Approach to Treating Rheumatoid Arthritis." The Rheumatologist. Jun. 2013, pp. 1-12. Available from: < http://www.therheumatologist.org/details/article/4871 781 IT ofacitin ib and_ Other_Kinase Inhibitors_Offer_New_Approach_to_Treating_Rheurnatoi.htm >.
Wang, Z. et al, IRAK-4 Inhibitors for Inflammation. Current Topics in Medicinal Chemistry, 2009, 9, 724-737.
Clark, James, D., et al. "Discovery and Development of Janus Kinase (JAK) Inhibitors for Inflammatory Diseases." (miniperspective) J. Med. Chem., Article ASAP; Publication Date (Web). Jan. 13, 2014.
MD Anderson Cancer Center. "Leukemia Prevention and Screening." (c) 2014.
Vippagunta, et al., "Crystalline solids," Advanced Drug Delivery Reviews, 48, 2001, 3-26.
Office Action dated Apr. 27, 2015, in U.S. Appl. No. 13/579,344, Examiner Douglas M. Willis.
Office Action dated May 1, 2015 in U.S. Appl. No. 14/589,056, Examiner Douglas M. Willis.

* cited by examiner

IMIDAZO[1,2-B]PYRIDAZINE AND IMIDAZO[4,5-B]PYRIDINE DERIVATIVES AS JAK INHIBITORS

This application is the national stage entry under 35 U.S.C. §371 of International Application No. PCT/EP2011/005929, filed on Nov. 24, 2011, which claims priority to U.S. Provisional Application No. 61/436,212, filed Jan. 26, 2011, and to European Application No. 10382318.3, filed Nov. 26, 2010. The contents of all three of the foregoing applications are incorporated herein by reference.

Cytokines have critical functions in regulating many aspects of immunity and inflammation, ranging from the development and differentiation of immune cells to the suppression of immune responses. Type I and type II cytokine receptors lack intrinsic enzymatic activity capable of mediating signal transduction, and thus require association with tyrosine kinases for this purpose. The JAK family of kinases comprises four different members, namely JAK1, JAK2, JAK3 and TYK2, which bind to type I and type II cytokine receptors for controlling signal transduction (Murray P J, (2007). The JAK-STAT signalling pathway: input and output integration. *J Immunol*, 178: 2623). Each of the JAK kinases is selective for the receptors of certain cytokines. In this regard, JAK-deficient cell lines and mice have validated the essential role of each JAK protein in receptor signalling: JAK1 in class II cytokine receptors (IFN and IL-10 family), those sharing the gp130 chain (IL-6 family) and the common gamma chain (IL-2, IL-4, IL-7, IL-9, IL-15 and IL-21) (Rodig et al. (1998). Disruption of the JAK1 gene demonstrates obligatory and nonredundant roles of the Jaks in cytokine-induced biological response. *Cell*, 93:373; Guschin et al. (1995). A major role for the protein tyrosine kinase JAK1 in the JAK/STAT signal transduction pathway in response to interleukin-6. *EMBO J.* 14: 1421; Briscoe et al. (1996). Kinase-negative mutants of JAK1 can sustain intereferon-gamma-inducible gene expression but not an antiviral state. *EMBO J.* 15:799); JAK2 in hematopoietic factors (Epo, Tpo, GM-CSF, IL-3, IL-5) and type II IFNs (Parganas et al., (1998). JAK2 is essential for signalling through a variety of cytokine receptors. *Cell*, 93:385); JAK3 in receptors sharing the common gamma chain (IL-2 family) (Park et al., (1995). Developmental defects of lymphoid cells in JAK3 kinase-deficient mice. *Immunity*, 3:771; Thomis et al., (1995). Defects in B lymphocyte maturation and T lymphocyte activation in mice lacking JAK3. *Science*, 270:794; Russell et al., (1995). Mutation of JAK3 in a patient with SCID: Essential role of JAK3 in lymphoid development. *Science*, 270:797); and Tyk2 in the receptors of IL-12, IL-23, IL-13 and type I IFNs (Karaghiosoff et al., (2000). Partial impairment of cytokine responses in Tyk2-deficient mice. *Immunity*, 13:549; Shimoda et al., (2000). Tyk2 plays a restricted role in IFNg signaling, although it is required for IL-12-mediated T cell function. Immunity, 13:561; Minegishi et al., (2006). Human Tyrosine kinase 2 deficiency reveals its requisite roles in multiple cytokine signals involved in innate and acquired immunity. Immunity, 25:745).

Receptor stimulation leads sequentially to JAK activation by phosphorylation, receptor phosphorylation, STAT protein recruitment and STAT activation and dimerization. The STAT dimer then functions as a transcription factor, translocating to the nucleus and activating the transcription of multiple response genes. There are seven STAT proteins identified: STAT1, STAT2, STAT3, STAT4, STAT5a, STAT5b and STAT6. Each particular cytokine receptor associates preferentially with a particular STAT protein. Some associations are independent of cell type (ex: IFNg-STAT1) while others may be cell type dependent (Murray P J, (2007). The JAK-STAT signaling pathway: input and output integration. *J Immunol*, 178: 2623).

The phenotype of deficient mice has provided insights on the function of each JAK and the cytokine receptors signaling through them. JAK3 associates exclusively with the common gamma chain of the receptors for IL-2, IL-4, IL-7, IL-9, IL-15 and IL-21 cytokines. By virtue of this exclusive association, JAK3 knock out mice and common gamma chain deficient mice have an identical phenotype (Thomis et al., (1995). Defects in B lymphocyte maturation and T lymphocyte activation in mice lacking JAK3. *Science*, 270:794; DiSanto et al., (1995). Lymphoid development in mice with a targeted deletion of the interleukin 2 receptor gamma chain. PNAS, 92:377). Moreover, this phenotype is shared to a great extent with SCID patients that hold mutations/defects in the common gamma chain or JAK3 genes (O'Shea et al., (2004). JAK3 and the pathogenesis of severe combined immunodeficiency. *Mol Immunol*, 41: 727). JAK3-deficient mice are viable but display abnormal lymphopoiesis which leads to a reduced thymus size (10-100 fold smaller than wild type). JAK3-deficient peripheral T cells are unresponsive and have an activated/memory cell phenotype (Baird et al., (1998). T cell development and activation in JAK3-deficient mice. *J. Leuk. Biol.* 63: 669). The thymic defect in these mice strongly resembles that seen in IL-7 and IL-7 receptor knockout mice, suggesting that the absence of IL-7 signaling accounts for this defect in JAK3-/-mice (von Freeden-Jeffry et al., (1995). Lymphopenia in Interleukin (IL)-7 Gene-deleted Mice Identifies IL-7 as a non-redundant Cytokine. *J Exp Med*, 181: 1519; Peschon et al, (1994). Early lymphocyte expansion is severely impaired in interleukin 7 receptor-deficient mice. *J Exp Med*, 180: 1955). These mice, like SCID humans, have no NK cells, probably due to the absence of IL-15 signaling, a survival factor for these cells. JAK3 knockout mice, unlike SCID patients, show deficient B cell lymphopoiesis while in human patients, B cells are present in circulation but are not responsive leading to hypoglobulinemia (O'Shea et al., (2004). JAK3 and the pathogenesis of severe combined immunodeficiency. *Mol Immunol*, 41: 727). This is explained by species-specific differences in IL-7 function in B and T cell development in mice and humans. On the other hand, Grossman et al. (1999. Dysregulated myelopoiesis in mice lacking JAK3. *Blood*, 94:932:939) have shown that the loss of JAK3 in the T-cell compartment drives the expansion of the myeloid lineages leading to dysregulated myelopoiesis.

JAK2-deficient mice are embrionically lethal, due to the absence of definitive erythropoiesis. Myeloid progenitors fail to respond to Epo, Tpo, IL-3 or GM-CSF, while G-CSF and IL-6 signaling are not affected. JAK2 is not required for the generation, amplification or functional differentiation of lymphoid progenitors (Parganas et al., (1998). JAK2 is essential for signaling through a variety of cytokine receptors. *Cell*, 93:385).

JAK1-deficient mice die perinatally due to a nursing defect. JAK1 binds exclusively to the gp130 chain shared by the IL-6 cytokine family (i.e. LIF, CNTF, OSM, CT-1) and along with JAK3, is an essential component of the receptors sharing the common gamma chain, by binding to the non-shared receptor subunit. In this regard, JAK1-deficient mice show similar hematopoiesis defects as JAK3-deficient mice. In addition, they show defective responses to neurotrophic factors and to all interferons (class II cytokine receptors) (Rodig et al., (1998). Disruption of the JAK1 gene demonstrates obligatory and non-redundant roles of the JAKs in cytokine-induced biological response. *Cell*, 93:373).

Finally, Tyk2-deficient mice show an impaired response to IL-12 and IL-23 and only partially impaired to IFN-alpha (Karaghiosoff et al., (2000). Partial impairment of cytokine responses in Tyk2-deficient mice. *Immunity*, 13:549; Shimoda et al., (2000). Tyk2 plays a restricted role in IFNg signaling, although it is required for IL-12-mediated T cell function. *Immunity*, 13:561). However, human Tyk2 deficiency demonstrates that Tyk2 is involved in the signaling from IFN-α, IL-6, IL-10, IL-12 and IL-23 (Minegishi et al., (2006). Human Tyrosine kinase 2 deficiency reveals its requisite roles in multiple cytokine signals involved in innate and acquired immunity. *Immunity*, 25:745).

The role of JAK kinases in transducing the signal from a myriad of cytokines makes them potential targets for the treatment of diseases in which cytokines have a pathogenic role, such as inflammatory diseases, including but not limited to allergies and asthma, chronic obstructive pulmonary disease (COPD), psoriasis, autoimmune diseases such as rheumatoid arthritis, amyotrophic lateral sclerosis and multiple sclerosis, uveitis, transplant rejection, as well as in solid and hematologic malignancies such as myeloproliferative disorders, leukemia and lymphomas.

Inhibition of JAK kinases, especially JAK1 and JAK3, could give rise to potent immunosuppression which could be used therapeutically to prevent transplant rejection. In this regard, the JAK inhibitor CP-690,550 (tasocitinib) has shown efficacy in several animal models of transplantation (heretopic heart transplantation in mice, cardiac allografts implanted in the ear of mice, renal allotransplantation in cynomolgous monkeys, aorta and tracheal transplantation in rats) by prolonging the mean survival time of grafts (West K (2009). CP-690,550, a JAK3 inhibitor as an immunosuppressant for the treatment of rheumatoid arthritis, transplant rejection, psoriasis and other immune-mediated disorders. *Curr. Op. Invest. Drugs* 10: 491).

In rheumatoid joints, an imbalance between pro and anti-inflammatory cytokine activities favours the induction of autoimmunity, followed by chronic inflammation and tissue destruction. In this regard, the pathogenic role of IL-6 in rheumatoid arthritis (RA) has been validated clinically by the use of the anti-IL-6R antibody tocilizumab. IL-6 activates the transcription factor STAT3, through the use of JAK1 binding to the gp130 receptor chain (Heinrich et al., (2003). Principles of interleukin (IL)-6-type cytokine signaling and its regulation. *Biochem J.* 374: 1). Constitutive STAT3 mediates the abnormal growth and survival properties of RA synoviocytes (Ivashkiv and Hu (2003). The JAK/STAT pathway in rheumatoid arthritis: pathogenic or protective? *Arth & Rheum.* 48:2092). Other cytokines that have been implicated in the pathogenesis of arthritis include IL-12 and IL-23, implicated in Th1 and Th17 cell proliferation, respectively; IL-15, and GM-CSF (McInnes and Schett, (2007). Cytokines in the pathogenesis of rheumatoid arthritis. *Nature Rew Immunol.* 7:429). The receptors for these cytokines also utilize JAK proteins for signal transduction, making JAK inhibitors potential pleiotropic drugs in this pathology. Consequently, administration of several JAK inhibitors in animal models of murine collagen-induced arthritis and rat adjuvant-induced arthritis has shown to reduce inflammation, and tissue destruction (Milici et al., (2008). Cartilage preservation by inhibition of Janus kinase 3 in two rodent models of rheumatoid arthritis. *Arth. Res.* 10:R14).

Inflammatory bowel disease (IBD) encloses two major forms of intestinal inflammation: ulcerative colitis and Crohn's disease. Growing evidence has shown that multiple cytokines, including interleukins and interferons, are involved in the pathogenesis of IBD (Strober et al, (2002). The immunology of mucosal models of inflammation. *Annu Rev Immunol.* 20: 495). Activation of the IL-6/STAT3 cascade in lamina propia T cells has been shown to induce prolonged survival of pathogenic T cells (Atreya et al, (2000). Blockade of interleukin 6 trans signaling suppresses T-cell resistance against apoptosis in chronic intestinal inflammation: Evidence in Crohn's disease and experimental colitis in vivo. *Nature Med.* 6:583). Specifically, STAT3 has been shown to be constitutively active in intestinal T cells of Crohn's disease patients and a JAK inhibitor has been shown to block the constitutive activation of STAT3 in these cells (Lovato et al, (2003). Constitutive STAT3 activation in intestinal T cells from patients with Crohn's disease. *J Biol. Chem.* 278:16777). These observations indicate that the JAK-STAT pathway plays a pathogenic role in IBD and that a JAK inhibitor could be therapeutic in this setting.

Multiple sclerosis is an autoimmune demyelinating disease characterized by the formation of plaques in the white matter. The role of cytokines in the generation of multiple sclerosis has long been known. Potential therapies include blockade of IFN-g, IL-6, IL-12 and IL-23 (Steinman L. (2008). Nuanced roles of cytokines in three major human brain disorders. *J Clin Invest.* 118:3557), cytokines that signal through the JAK-STAT pathways. Use of tyrphostin, a JAK inhibitor, has been shown to inhibit IL-12-induced phosphorylation of STAT3, and to reduce the incidence and severity of active and passive experimental autoimmune encephalitis (EAE) (Bright et al., (1999) Tyrphostin B42 inhibits IL-12-induced tyrosine phosphorylation and activation of Janus kinase-2 and prevents experimental allergic encephalomyelitis. *J Immunol.* 162:6255). Another multikinase inhibitor, CEP701, has been shown to reduce secretion of TNF-alpha, IL-6 and IL-23 as well as the levels of phospho-STAT1, STAT3, and STAT5 in peripheral DCs of mice with EAE, significantly improving the clinical course of EAE in mice (Skarica et al, (2009). Signal transduction inhibition of APCs diminishes Th17 and Th1 responses in experimental autoimmune encephalomyelitis. *J. Immunol.* 182:4192).

Psoriasis is a skin inflammatory disease which involves a process of immune cell infiltration and activation that culminates in epithelial remodeling. The current theory behind the cause of psoriasis states the existence of a cytokine network that governs the interaction between immune and epithelial cells (Nickoloff B J. (2007). Cracking the cytokine code in psoriasis, *Nat Med,* 13:242). In this regard, IL-23 produced by dendritic cells is found elevated in psoriatic skin, along with IL-12. IL-23 induces the formation of Th17 cells which in turn produce IL-17 and IL-22, the last one being responsible for epidermis thickening. IL-23 and IL-22 induce the phosphorylation of STAT-3, which is found abundantly in psoriatic skin. JAK inhibitors may thus be therapeutic in this setting. In accordance, a JAK1/3 inhibitor, R348, has been found to attenuate psoriasiform skin inflammation in a spontaneous T cell-dependent mouse model of psoriasis (Chang et al., (2009). JAK3 inhibition significantly attenuates psoriasiform skin inflammation on CD18 mutant PUJ mice. *J Immunol.* 183:2183).

Th2 cytokine-driven diseases such as allergy and asthma could also be a target of JAK inhibitors. IL-4 promotes Th2 differentiation, regulates B-cell function and immunoglobulin class switching, regulates eotaxin production, induces expression of IgE receptor and MHC II on B cells, and stimulates mast cells. Other Th2 cytokines like IL-5 and IL-13 can also contribute to eosinophil recruitment in bronchoalveolar lavage by stimulating eotaxin production. Pharmacological inhibition of JAK has been shown to reduce the expression of IgE receptor and MHCII induced by IL-4 stimulation on B cells (Kudlacz et al., (2008). The JAK3 inhibitor CP-690,550 is a potent anti-inflammatory agent in a murine model of pulmonary eosinophilia. *European J. Pharm.* 582: 154). Furthermore, JAK3-deficient mice display poor eosinophil recruitment and mucus secretion to the airway lumen upon OVA challenge, as compared to wild type mice (Malaviya et al, (2000). Treatment of allergic asthma by targeting Janus kinase 3-dependent leukotriene synthesis in mast cells with 4-(3',5'-dibromo-4'-hydroxyphenyl)amino-6,7-dimethoxyquinazoline (WHI-P97). *JPET* 295:912). In this regard, systemic administration of the CP-690,550 JAK inhibitor in mice has been shown to reduce the eosinophil count as well as the levels of eotaxin and IL13 in BAL in a murine model of pulmonary eosinophilia (Kudlacz et al., (2008). The JAK3 inhibitor CP-690,550 is a potent anti-inflammatory agent in a murine model of pulmonary eosinophilia. *European J. Pharm.* 582:154).

There is increasing evidence that cytokines play a pathogenetic role in ocular inflammatory disease such as uveitis or dry eye syndrome. Some cytokines implicated in experimental autoimmune uveitis, such as IL-2, IL-6, IL-12 and IFNg, would be amenable to JAK inhibition (Vallochi et al, (2007). The role of cytokines in the regulation of ocular autoimmune inflammation. *Cytok Growth Factors Rev.* 18:135). In this regard, drugs or biologicals that interfere with IL-2 signaling such as cyclosporine or anti-IL-2 receptor antibody (daclizumab) have shown efficacy in the treatment of keratoconjuctivitis sicca and refractory uveitis, respectively (Lim et al, (2006). Biologic therapies for inflammatory eye disease. *Clin Exp Opht* 34:365). Similarly, allergic conjunctivitis, a common allergic eye disease characterized by conjunctival congestion, mast cell activation and eosinophil infiltration, could benefit from JAK inhibition. STAT6-deficient mice, showing decreased TH2-mediated immune responses which are normally triggered by IL-4, do not develop the classical early and late phase responses, suggesting that IL-4 pathway abrogation through JAK inhibition may be therapeutic in this setting (Ozaki et al, (2005). The control of allergic conjunctivitis by suppression of cytokine signaling (SOCS)$_3$ and SOCS5 in a murine model. *J Immunol,* 175:5489).

There is growing evidence of the critical role of STAT3 activity in processes involved in tumorigenesis like cell cycle dysregulation, promotion of uncontrolled growth, induction of survival factors and inhibition of apoptosis (Siddiquee et al., (2008). STAT3 as a target for inducing apoptosis in solid and haematological tumors. *Cell Res.* 18: 254). Antagonism of STAT3 by means of dominant-negative mutants or antisense oligonucleotides has shown to promote apoptosis of cancer cells, inhibition of angiogenesis and up-regulation of host immunocompetence. Inhibition of constitutively active STAT3 in human tumors by means of JAK inhibitors may provide a therapeutic option to the treatment of this disease. In this regard, the use of the JAK inhibitor tyrphostin has been shown to induce apoptosis of malignant cells and inhibit cell proliferation in vitro and in vivo (Meydan et al., (1996). Inhibition of acute lymphoblastic leukemia by a JAK-2 inhibitor. *Nature,* 379:645).

Hematological malignancies with dysregulated JAK-STAT pathways may benefit from JAK inhibition. Recent studies have implicated dysregulation of JAK2 kinase activity by chromosomal translocations and mutations within the pseudokinase domain (such as the JAK2V617F mutation) in a spectrum of myeloproliferative diseases (Ihle and Gililand, 2007), including polycythemia vera, myelofibrosis and essential thrombocythemia. In this regard, several JAK inhibitors that tackle JAK2 potently, such as TG-101209 (Pardanani et al., (2007). TG101209, a small molecular JAK2-selective inhibitor potently inhibits myeloproliferative disorder-associated JAK2V617F and MPLW515L/K mutations *Leukemia.* 21:1658-68), TG101348 (Wernig et al, (2008). Efficacy of TG101348, a selective JAK2 inhibitor, in treatment of a murine model of JAK2V617F-induced polycythemia vera. *Cancer Cell,* 13: 311), CEP701, (Hexner et al, (2008). Lestaurtinib (CEP701) is a JAK2 inhibitor that suppresses JAK2/STAT5 signaling and the proliferation of primary erythroid cells from patients with myeloproliferative disorders. *Blood,* 111: 5663), CP-690,550 (Manshouri et al, (2008). The JAK kinase inhibitor CP-690,550 suppresses the growth of human polycythemia vera cells carrying the JAK2V617F mutation. *Cancer Sci,* 99:1265), and CYT387 (Pardanani et al., (2009). CYT387, a selective JAK1/JAK2 inhibitor: invitro assessment of kinase selectivity and preclinical studies using cell lines and primary cells from polycythemia vera patients. *Leukemia,* 23:1441) have been proposed for treating myeloproliferative diseases on the basis of their antiproliferative activity on cells carrying the JAK2V617F mutation. Similarly, T-cell leukemia due to human T-cell leukemia virus (HTLV-1) transformation is associated with JAK3 and STAT5 constitutive activation (Migone et al, (1995). Constitutively activated JAK-STAT pathway in T cells transformed with HTLV-I. *Science,* 269: 79) and JAK inhibitors may be therapeutic in this setting (Tomita et al, (2006). Inhibition of constitutively active JAK-STAT pathway suppresses cell growth of human T-cell leukemia virus type I-infected T cell lines and primary adult T-cell leukemia cells. *Retrovirology,* 3:22). JAK1-activating mutations have also been identified in adult acute lymphoblastic leukemia of T cell origin (Flex et al, (2008). Somatically acquired JAK1 mutations in adult acute lymphoblastic leukemia. *J. Exp. Med.* 205:751-8) pointing to this kinase as a target for the development of novel antileukemic drugs.

Conditions in which targeting of the JAK pathway or modulation of the JAK kinases, particularly JAK1, JAK2 and JAK3 kinases, are contemplated to be therapeutically useful for the treatment or prevention of diseases include: neoplastic diseases (e.g. leukemia, lymphomas, solid tumors); transplant rejection, bone marrow transplant applications (e.g., graft-versus-host disease); autoimmune diseases (e.g. diabetes, multiple sclerosis, rheumatoid arthritis, inflammatory bowel disease); respiratory inflammation diseases (e.g. asthma, chronic obstructive pulmonary disease), inflammation-linked ocular diseases or allergic eye diseases (e.g. dry eye, glaucoma, uveitis, diabetic retinopathy, allergic conjunctivitis or age-related macular degeneration) and skin inflammatory diseases (e.g., atopic dermatitis or psoriasis).

In view of the numerous conditions that are contemplated to benefit by treatment involving modulation of the JAK pathway or of the JAK Kinases it is immediately apparent that new compounds that modulate JAK pathways and use of these compounds should provide substantial therapeutic benefits to a wide variety of patients.

Provided herein are novel imidazo[1,2-b]pyridazine and imidazo[4,5-b]pyridine derivatives for use in the treatment of conditions in which targeting of the JAK pathway or inhibition of JAK kinases can be therapeutically useful.

The compounds described in the present invention are simultaneously potent JAK1, JAK2 and JAK3 inhibitors, i.e. pan-JAK inhibitors. This property makes them useful for the treatment or prevention of pathological conditions or diseases such as myeloproliferative disorders (such as polycythemia vera, essential thrombocythemia or myelofibrosis), leukemia, lymphomas and solid tumors; bone marrow and organ transplant rejection; immune-mediated diseases and inflammatory diseases, including rheumatoid arthritis, multiple sclerosis, inflammatory bowel disease (such as ulcerative colitis or Crohn's disease), inflammation-linked ocular diseases or allergic eye diseases (such as dry eye, uveitis, or allergic conjunctivitis), allergic rhinitis, asthma, chronic obstructive pulmonary disease (COPD), and skin inflammatory diseases (such as atopic dermatitis or psoriasis).

It has now been found that certain imidazo[1,2-b]pyridazine and imidazo[4,5-b]pyridine derivatives are novel and potent JAK inhibitors and can therefore be used in the treatment or prevention of these diseases.

Thus the present invention is directed to compounds of formula (I), or a pharmaceutically acceptable salt, or solvate, or N-oxide, or stereoisomer or deuterated derivative or tautomer thereof:

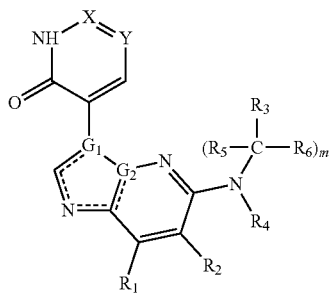

Formula (I)

wherein,
m is 0 or an integer from 1 to 3;
X and Y each independently represent a nitrogen atom or a —$CR_7$ group, wherein at least one of X and Y represents a —$CR_7$ group;
One of $G_1$ and $G_2$ represents a nitrogen atom and the other represents a carbon atom;
$R_1$ and $R_2$ each independently represent a hydrogen atom, a halogen atom, a hydroxy group, a cyano group, a linear or branched $C_1$-$C_6$ alkyl group, a $C_1$-$C_4$ haloalkyl group, a $C_1$-$C_4$ hydroxyalkyl group, a $C_3$-$C_{10}$ cycloalkyl group, a $C_3$-$C_{10}$ cycloalkenyl group, a monocyclic or polycyclic $C_5$-$C_{14}$ aryl group, a 5- to 14-membered heteroaryl group containing at least one heteroatom selected from O, S and N, a 5- to 14-membered heterocyclyl group containing at least one heteroatom selected from O, S and N,
  wherein the alkyl, haloalkyl, hydroxyalkyl, cycloalkyl, cycloalkenyl, aryl, heteroaryl, and heterocyclyl groups are unsubstituted or substituted by one or more substituents selected from a halogen atom, a cyano group, a linear or branched $C_1$-$C_6$ alkyl group, a $C_1$-$C_4$ haloalkyl group, a $C_1$-$C_4$ hydroxyalkyl group, a $C_1$-$C_4$ alkylsulfonyl group, a $C_3$-$C_7$ cycloalkyl group, a phenyl group, a pyridyl group, a pyrimidinyl group or a piperidyl group;
or $R_1$ and $R_2$ each independently represent a —$(CH_2)_{0-2}OR_9$ group, a —O—$(CH_2)_{1-2}OR_9$ group, or a —$NR_8R_9$ group;
$R_3$ represents a hydrogen atom, a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_{10}$ cycloalkyl group, a $C_3$-$C_{10}$ cycloalkenyl group, a monocyclic or polycyclic $C_5$-$C_{14}$ aryl group, a 5- to 14-membered heteroaryl group containing at least one heteroatom selected from O, S and N, a 5- to 14-membered heterocyclyl group containing at least one heteroatom selected from O, S and N,
  wherein the alkyl, haloalkyl, hydroxyalkyl, cycloalkyl, cycloalkenyl, aryl, heteroaryl, and heterocyclyl groups are unsubstituted or substituted by one or more substituents selected from a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a phenyl group, a pyridyl group, a pyrimidinyl group, a piperidyl group, a —$(CH_2)_nOR_9$ group, a —$NR_8R_9$ group, a —C(O)—$(CH_2)_n$—$R_8$ group, a —C(O)—$(CH_2)_n$—$NR_8R_9$ group, a —$S(O)_2(CH_2)_nR_9$ group or a —$S(O)_2(CH_2)_nNR_8R_9$ group; wherein each n is 0, 1 or 2;
$R_4$ represents a hydrogen atom, a $C_1$-$C_4$ haloalkyl group, a $C_1$-$C_4$ hydroxyalkyl group or a linear or branched $C_1$-$C_6$ alkyl group, which alkyl group is unsubstituted or substituted by one or more substituents selected from a cyano group, a $C_3$-$C_7$ cycloalkyl group, a phenyl group, a pyridyl group, a pyrimidinyl group or a piperidyl group;
$R_5$ and $R_6$ each independently represent a hydrogen atom, a $C_1$-$C_4$ haloalkyl group, a $C_1$-$C_4$ hydroxyalkyl group or a linear or branched $C_1$-$C_6$ alkyl group, which alkyl group is unsubstituted or substituted by one or more substituents selected from a cyano group, a $C_3$-$C_7$ cycloalkyl group, a phenyl group, a pyridyl group, a pyrimidinyl group or a piperidyl group;
$R_7$ represents a hydrogen atom, a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_{10}$ cycloalkyl group, a $C_3$-$C_{10}$ cycloalkenyl group, a monocyclic or polycyclic $C_5$-$C_{14}$ aryl group, a 5- to 14-membered heteroaryl group containing at least one heteroatom selected from O, S and N, a 5- to 14-membered heterocyclyl group containing at least one heteroatom selected from O, S and N,
  wherein the alkyl, haloalkyl, hydroxyalkyl, cycloalkyl, cycloalkenyl, aryl, heteroaryl, and heterocyclyl groups are unsubstituted or substituted by one or more substituents selected from a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl, a phenyl group, a pyridyl group, a pyrimidinyl group or a piperidyl group;
$R_8$ represents a hydrogen atom, a cyano group, a $C_1$-$C_4$ haloalkyl group, a $C_1$-$C_4$ hydroxyalkyl group or a linear or branched $C_1$-$C_6$ alkyl group, which alkyl group is unsubstituted or substituted by one or more substituents selected from a cyano group, a $C_3$-$C_7$ cycloalkyl group, a phenyl group, a pyridyl group, a pyrimidinyl group or a piperidyl group;
$R_9$ represents a hydrogen atom, a $C_1$-$C_4$ haloalkyl group, a $C_1$-$C_4$ hydroxyalkyl group or a linear or branched $C_1$-$C_6$ alkyl group, which alkyl group is unsubstituted or substituted by one or more substituents selected from a cyano group, a $C_3$-$C_7$ cycloalkyl group, a phenyl group, a pyridyl group, a pyrimidinyl group or a piperidyl group.

The invention further provides synthetic processes and intermediates described herein, which are useful for preparing said compounds.

The invention is also directed to a compound of the invention as described herein for use in the treatment of the human or animal body by therapy.

The invention also provides a pharmaceutical composition comprising the compounds of the invention and a pharmaceutically-acceptable diluent or carrier.

The invention is also directed to the compounds of the invention as described herein, for use in the treatment of a pathological condition or disease susceptible to amelioration by inhibition of Janus Kinases (JAK), in particular wherein the pathological condition or disease is selected from myeloproliferative disorders, leukemia, lymphoid malignancies and solid tumors; bone marrow and organ transplant rejection; immune-mediated diseases and inflammatory diseases;

more in particular wherein the pathological condition or disease is selected from rheumatoid arthritis, multiple sclerosis, inflammatory bowel disease, dry eye, uveitis, allergic conjunctivitis, allergic rhinitis, asthma, chronic obstructive pulmonary disease (COPD), atopic dermatitis and psoriasis.

The invention is also directed to use of the compounds of the invention as described herein, in the manufacture of a medicament for treatment of a pathological condition or disease susceptible to amelioration by inhibiton of Janus Kinases (JAK), in particular wherein the pathological condition or disease is selected from myeloproliferative disorders, leukemia, lymphoid malignancies and solid tumors; bone marrow and organ transplant rejection; immune-mediated diseases and inflammatory diseases; more in particular wherein the pathological condition or disease is selected from rheumatoid arthritis, multiple sclerosis, inflammatory bowel disease, dry eye, uveitis, allergic conjunctivitis, allergic rhinitis, asthma, chronic obstructive pulmonary disease (COPD), atopic dermatitis and psoriasis.

The invention also provides a method of treatment of a pathological condition or disease susceptible to amelioration by inhibition of Janus Kinases (JAK), in particular wherein the pathological condition or disease is selected from myeloproliferative disorders, leukemia, lymphoid malignancies and solid tumors; bone marrow and organ transplant rejection; immune-mediated diseases and inflammatory diseases, more in particular wherein the pathological condition or disease is selected from rheumatoid arthritis, multiple sclerosis, inflammatory bowel disease, dry eye, uveitis, allergic conjunctivitis, allergic rhinitis, asthma, chronic obstructive pulmonary disease (COPD), atopic dermatitis and psoriasis; comprising administering a therapeutically effective amount of the compounds of the invention or a pharmaceutical composition of the invention to a subject in need of such treatment.

The invention also provides a combination product comprising (i) the compounds of the invention as described herein; and (ii) one or more additional active substances which are known to be useful in the treatment of myeloproliferative disorders (such as polycythemia vera, essential thrombocythemia or mielofibrosis), leukemia, lymphoid malignancies and solid tumors; bone marrow and organ transplant rejection; immune-mediated diseases and inflammatory diseases, more in particular wherein the pathological condition or disease is selected from rheumatoid arthritis, multiple sclerosis, inflammatory bowel disease (such as ulcerative colitis or Crohn's disease), dry eye, uveitis, allergic conjunctivitis, allergic rhinitis, asthma, chronic obstructive pulmonary disease (COPD), atopic dermatitis and psoriasis.

The invention also provides a combination product as defined herein for simultaneous, separate or sequential use in the treatment of the human or animal body.

As used herein the term $C_1$-$C_6$ alkyl embraces linear or branched radicals having 1 to 6 carbon atoms, preferably 1 to 4 carbon atoms. Examples include methyl, ethyl, n-propyl, i-propyl, n-butyl, sec-butyl, t-butyl, n-pentyl, 1-methylbutyl, 2-methylbutyl, isopentyl, 1-ethylpropyl, 1,1-dimethylpropyl, 1,2-dimethylpropyl, n-hexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 2-methylpentyl, 3-methylpentyl and iso-hexyl radicals.

When it is mentioned that the alkyl radical may be optionally substituted it is meant to include linear or branched alkyl radical as defined above, which may be unsubstituted or substituted in any position by one or more substituents, for example by 1, 2 or 3 substituents. When two or more substituents are present, each substituent may be the same or different.

As used herein, the term $C_1$-$C_4$ haloalkyl group is an alkyl group, for example a $C_1$-$C_4$ or $C_1$-$C_2$ alkyl group, which is bonded to one or more, preferably 1, 2 or 3 halogen atoms. Preferably, said haloakyl group is chosen from —$CCl_3$, —$CHF_2$ and —$CF_3$.

As used herein, the term $C_1$-$C_4$ hydroxyalkyl embraces linear or branched alkyl radicals having 1 to 4 carbon atoms, any one of which may be substituted by one or more, preferably 1 or 2, more preferably 1 hydroxyl radicals. Examples of such radicals include hydroxymethyl, hydroxyethyl, hydroxypropyl, and hydroxybutyl.

As used herein, the term $C_1$-$C_4$ alkylsulfonyl embraces radicals containing an optionally substituted, linear or branched alkyl radicals of 1 to 4 carbon atoms attached to a divalent —$SO_2$— radical.

As used herein, the term $C_3$-$C_{10}$ cycloalkyl embraces saturated monocyclic or polycyclic carbocyclic radicals having from 3 to 10 carbon atoms, preferably from 3 to 7 carbon atoms. An optionally substituted $C_3$-$C_{10}$ cycloalkyl radical is typically unsubstituted or substituted by 1, 2 or 3 substituents which may be the same or different. When a $C_3$-$C_{10}$ cycloalkyl radical carries 2 or more substituents, the substituents may be the same or different. Typically the substituents on a $C_3$-$C_{10}$ cycloalkyl group are themselves unsubstituted. Polycyclic cycloalkyl radicals contains two or more fused cycloalkyl groups, preferably two cycloalkyl groups. Typically, polycyclic cycloalkyl radicals are selected from decahydronaphthyl(decalyl), bicyclo[2.2.2]octyl, adamantly, camphyl or bornyl groups.

Examples of monocyclic cycloalkyl groups include cyclopropyl, cyclobutyl, cyclopentyl, cyclohexyl, cycloheptyl, cyclooctyl, cyclononyl and cyclodecyl.

As used herein, the term $C_3$-$C_{10}$ cycloalkenyl embraces partially unsaturated carbocyclic radicals having from 3 to 10 carbon atoms, preferably from 3 to 7 carbon atoms. A $C_3$-$C_{10}$ cycloalkenyl radical is typically unsubstituted or substituted by 1, 2 or 3 substituents which may be the same or different. When a $C_3$-$C_{10}$ cycloalkenyl radical carries 2 or more substituents, the substituents may be the same or different. Typically, the substituents on a cycloalkenyl group are themselves unsubstituted. Examples include cyclobutenyl, cyclopentenyl, cyclohexenyl, cycloheptenyl, cyclooctenyl, cyclononenyl and cyclodecenyl.

As used herein, the term $C_5$-$C_{14}$ aryl radical embraces typically a $C_5$-$C_{14}$, preferably $C_6$-$C_{14}$, more preferably $C_6$-$C_{10}$ monocyclic or polycyclic aryl radical such as phenyl, naphthyl, anthranyl and phenanthryl. Phenyl is preferred. A said optionally substituted $C_5$-$C_{14}$ aryl radical is typically unsubstituted or substituted by 1, 2 or 3 substituents which may be the same or different. When a $C_5$-$C_{14}$ aryl radical carries 2 or more substituents, the substituents may be the same or different. Unless otherwise specified, the substituents on a $C_5$-$C_{14}$ aryl group are typically themselves unsubstituted.

As used herein, the term 5- to 14-membered heteroaryl radical embraces typically a 5- to 14-membered ring system, preferably a 5- to 10-membered ring system, more preferably a 5- to 6-membered ring system, comprising at least one heteroaromatic ring and containing at least one heteroatom selected from O, S and N. A 5- to 14-membered heteroaryl radical may be a single ring or two or more fused rings wherein at least one ring contains a heteroatom.

A said optionally substituted 5- to 14-membered heteroaryl radical is typically unsubstituted or substituted by 1, 2 or 3 substituents which may be the same or different. When a 5- to 14-membered heteroaryl radical carries 2 or more substituents, the substituents may be the same or different. Unless otherwise specified, the substituents on a 5- to 14-membered heteroaryl radical are typically themselves unsubstituted.

Examples include pyridyl, pyrazinyl, pyrimidinyl, pyridazinyl, furyl, benzofuranyl, oxadiazolyl, oxazolyl, isoxazolyl, benzoxazolyl, imidazolyl, benzimidazolyl, thiazolyl, thiadiazolyl, thienyl, pyrrolyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, imidazolidinyl, pteridinyl, thianthrenyl, pyrazolyl, 2H-pyrazolo[3,4-d]pyrimidinyl, 1H-pyrazolo[3,4-d]pyrimidinyl, thieno[2,3-d]pyrimidinyl and the various pyrrolopyridyl radicals.

As used herein, the term 5- to 14-membered heterocyclyl radical embraces typically a non-aromatic, saturated or unsaturated $C_5$-$C_{14}$ carbocyclic ring system, preferably $C_5$-$C_{10}$ carbocyclic ring system, more preferably $C_5$-$C_6$-carbocyclic ring system, in which one or more, for example 1, 2, 3 or 4 of the carbon atoms preferably 1 or 2 of the carbon atoms are replaced by a heteroatom selected from N, O and S. A heterocyclyl radical may be a single ring or two or more fused rings wherein at least one ring contains a heteroatom. When a 5 to 14-membered heterocyclyl radical carries 2 or more substituents, the substituents may be the same or different.

A said optionally substituted 5- to 14-membered heterocyclyl radical is typically unsubstituted or substituted by 1, 2 or 3 substituents which may be the same or different. Typically, the substituents on a 5 to 14-membered heterocyclyl radical are themselves unsubstituted.

Examples of 5- to 14-membered heterocyclyl radicals include piperidyl, pyrrolidyl, pyrrolinyl, piperazinyl, morpholinyl, thiomorpholinyl, pyrrolyl, pyrazolinyl, pirazolidinyl, quinuclidinyl, triazolyl, pyrazolyl, tetrazolyl, imidazolidinyl, imidazolyl, oxiranyl, thiaranyl, aziridinyl, oxetanyl, thiatanyl, azetidinyl, 4,5-dihydro-oxazolyl, 2-benzofuran-1(3H)-one, 1,3-dioxol-2-one, tetrahydrofuranyl, 3-aza-tetrahydrofuranyl, tetrahydrothiophenyl, tetrahydropyranyl, tetrahydrothiopyranyl, 1,4-azathianyl, oxepanyl, thiephanyl, azepanyl, 1,4-dioxepnayl, 1,4-oxathiepanyl, 1,4-oxaazepanyl, 1,4-dithiepanyl, 1,4-thiezepanyl, 1,4-diazepanyl, tropanyl, (1S,5R)-3-aza-bicyclo[3.1.0]hexyl, 3,4-dihydro-2H-pyranyl, 5,6-dihydro-2H-pyranyl, 2H-pyranyl, 2,3-hydrobenzofuranyl, 1,2,3,4-tetrahydropyridinyl, 1,2,5,6-tetrahydropyridinyl, isoindolinyl and indolinyl.

Where a 5- to 14-membered heterocyclyl radical carries 2 or more substituents, the substituents may be the same or different.

As used herein, the term 5- to 7-membered saturated N-containing heterocyclic group is a $C_5$-$C_7$ saturated carbocyclic ring system in which one of the carbon atoms is replaced by N and optionally in which 1, 2, or 3, preferably 1 or 2, further carbon atoms are replaced by heteroatoms selected from N and O.

A said 5- to 7-membered saturated N-containing heterocyclic group is typically unsubstituted or substituted by 1, 2 or 3 substituents which may be the same or different. Typically, the substituents on a 5- to 7-membered saturated N-containing heterocyclic group are themselves unsubstituted, unless otherwise specified.

Examples of 5- to 7-membered saturated N-containing heterocyclic group include pyrrolidinyl, piperidyl, piperazinyl and azepanyl.

As used herein, some of the atoms, radicals, moieties, chains and cycles present in the general structures of the invention are "optionally substituted". This means that these atoms, radicals, moieties, chains and cycles can be either unsubstituted or substituted in any position by one or more, for example 1, 2, 3 or 4, substituents, whereby the hydrogen atoms bound to the unsubstituted atoms, radicals, moieties, chains and cycles are replaced by chemically acceptable atoms, radicals, moieties, chains and cycles. When two or more substituents are present, each substituent may be the same or different. The substituents are typically themselves unsubstituted.

As used herein, the term halogen atom embraces chlorine, fluorine, bromine and iodine atoms. A halogen atom is typically a fluorine, chlorine or bromine atom, most preferably chlorine or fluorine. The term halo when used as a prefix has the same meaning.

Compounds containing one or more chiral centre may be used in enantiomerically or diastereoisomerically pure form, in the form of racemic mixtures and in the form of mixtures enriched in one or more stereoisomer. The scope of the invention as described and claimed encompasses the racemic forms of the compounds as well as the individual enantiomers, diastereomers, and stereoisomer-enriched mixtures.

Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomehc mixture may be separated by chromatography and/or fractional crystallization and one or both of the diastereoisomers converted to the corresponding pure enantiomer(s) by means well known to one skilled in the art. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomer conglomerates may be separated by conventional techniques known to those skilled in the art. See, e.g. "Stereochemistry of Organic Compounds" by Ernest L. Eliel (Wiley, New York, 1994).

As used herein, the term pharmaceutically acceptable salt refers to a salt prepared from a base or acid which is acceptable for administration to a patient, such as a mammal. Such salts can be derived from pharmaceutically-acceptable inorganic or organic bases and from pharmaceutically-acceptable inorganic or organic acids.

Pharmaceutically acceptable acids include both inorganic acids, for example hydrochloric, sulphuric, phosphoric, diphosphoric, hydrobromic, hydroiodic and nitric acid; and organic acids, for example citric, fumaric, gluconic, glutamic, lactic, maleic, malic, mandelic, mucic, ascorbic, oxalic, pantothenic, succinic, tartaric, benzoic, acetic, methanesulphonic, ethanesulphonic, benzenesulphonic, p-toluenesulphonic acid, xinafoic (1-hydroxy-2-naphthoic acid), napadisilic (1,5-naphthalenedisulfonic acid) and the like. Particularly preferred are salts derived from fumaric, hydrobromic, hydrochloric, acetic, sulfuric, methanesulfonic, xinafoic, and tartaric acids.

Salts derived from pharmaceutically-acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts.

Salts derived from pharmaceutically-acceptable organic bases include salts of primary, secondary and tertiary amines, including alkyl amines, arylalkyl amines, heterocyclyl amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

Other preferred salts according to the invention are quaternary ammonium compounds wherein an equivalent of an anion ($X^-$) is associated with the positive charge of the N atom. $X^-$ may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. $X^-$ is preferably an anion selected from chloride, bromide, iodide, sulphate, nitrate, acetate, maleate, oxalate, succinate or trifluoroacetate. More preferably $X^-$ is chloride, bromide, trifluoroacetate or methanesulphonate.

As used herein, an N-oxide is formed from the tertiary basic amines or imines present in the molecule, using a convenient oxidising agent.

The compounds of the invention may exist in both unsolvated and solvated forms. The term solvate is used herein to describe a molecular complex comprising a compound of the invention and an amount of one or more pharmaceutically acceptable solvent molecules. The term hydrate is employed when said solvent is water. Examples of solvate forms include, but are not limited to, compounds of the invention in association with water, acetone, dichloromethane, 2-propanol, ethanol, methanol, dimethylsulfoxide (DMSO), ethyl acetate, acetic acid, ethanolamine, or mixtures thereof. It is specifically contemplated that in the present invention one solvent molecule can be associated with one molecule of the compounds of the present invention, such as a hydrate.

Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-solvate form of the compounds.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$. Certain isotopically-labeled compounds of the invention, for example, those incorporating a radioactive isotope, are useful in drug and/or substrate tissue distribution studies. The radioactive isotopes tritium, $^3H$, and carbon-14, $^{14}C$, are particularly useful for this purpose in view of their ease of incorporation and ready means of detection. Substitution with heavier isotopes such as deuterium, $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Preferred isotopically-labeled compounds include deuterated derivatives of the compounds of the invention. As used herein, the term deuterated derivative embraces compounds of the invention where in a particular position at least one hydrogen atom is replaced by deuterium. Deuterium (D or $^2H$) is a stable isotope of hydrogen which is present at a natural abundance of 0.015 molar %.

Hydrogen deuterium exchange (deuterium incorporation) is a chemical reaction in which a covalently bonded hydrogen atom is replaced by a deuterium atom. Said exchange (incorporation) reaction can be total or partial.

Typically, a deuterated derivative of a compound of the invention has an isotopic enrichment factor (ratio between the isotopic abundance and the natural abundance of that isotope, i.e. the percentage of incorporation of deuterium at a given position in a molecule in the place of hydrogen) for each deuterium present at a site designated as a potential site of deuteration on the compound of at least 3500 (52.5% deuterium incorporation).

In a preferred embodiment, the isotopic enrichment factor is at least 5000 (75% deuterium). In a more preferred embodiment, the isotopic enrichment factor is at least 6333.3 (95% deuterium incorporation). In a most preferred embodiment, the isotopic enrichment factor is at least 6633.3 (99.5% deuterium incorporation). It is understood that the isotopic enrichment factor of each deuterium present at a site designated as a site of deuteration is independent from the other deuteration sites.

The isotopic enrichment factor can be determined using conventional analytical methods known too en ordinary skilled in the art, including mass spectrometry (MS) and nuclear magnetic resonance (NMR).

Prodrugs of the compounds described herein are also within the scope of the invention. Thus certain derivatives of the compounds of the present invention, which derivatives may have little or no pharmacological activity themselves, when administered into or onto the body may be converted into compounds of the present invention having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

Prodrugs in accordance with the invention can, for example, be produced by replacing appropriate functionalities present in the compounds of the present invention with certain moieties known to those skilled in the art as 'pro-moieties' as described, for example, in Design of Prodrugs by H. Bundgaard (Elsevier, 1985).

In the case of compounds that are solids, it is understood by those skilled in the art that the inventive compounds and salts may exist in different crystalline or polymorphic forms, or in an amorphous form, all of which are intended to be within the scope of the present invention.

Tautomers of the compounds described herein are also within the scope of the invention. For example, the moiety

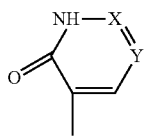

as represented in formulae (1), (1-a) and (1-b) may also exist in the form

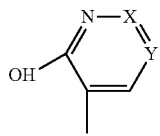

In one embodiment, the present invention includes pharmaceutically acceptable salts, solvates, N-oxides, stereoisomers, isotopically labelled derivatives, prodrugs and polymorphs of the compounds described herein, e.g. of a compound of formula (1-a).

Typically, the present invention includes pharmaceutically acceptable salts, solvates, N-oxides, stereoisomers or deuterated derivatives of the compounds described herein, e.g. of a compound of formula (1-a).

The dotted lines in the fused heterocyclic ring containing $G_1$ and $G_2$ in the compounds of formula (I) denotes that there are two double bounds in the ring, whose position may vary depending on which of $G_1$ and $G_2$ represents a nitrogen atom and which represents a carbon atom. Thus, when $G_1$ represents a nitrogen atom and $G_2$ represents a carbon atom, the ring is represented by the formula

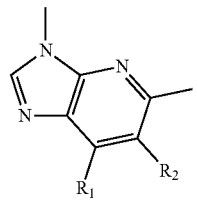

and when $G_2$ represents a nitrogen atom and $G_1$ represents a carbon atom, the ring is represented by the formula

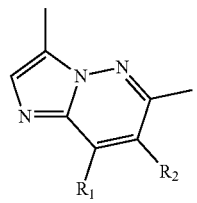

Typically, in the compound of formula (I), X and Y each independently represent a nitrogen atom or a —$CR_7$ group, wherein at least one of X and Y represents a —$CR_7$ group.

In one embodiment, in the compound of formula (I) X represents a nitrogen atom and Y represents a —$CR_7$ group.

In other embodiment, in the compound of formula (I) Y represents a nitrogen atom and X represents a —$CR_7$ group.

In another embodiment, in the compound of formula (I) X and Y independently represent a —$CR_7$ group.

In a preferred embodiment, in the compound of formula (I) X represents a nitrogen atom and Y represents a —$CR_7$ group; or X and Y independently represent a —$CR_7$ group. In a particular preferred embodiment, in the compound of formula (I) X and Y independently represent a —$CR_7$ group.

For the avoidance of doubt, when two $R_7$ groups are present, they may be the same or different.

In one embodiment, in the compound of formula (I) $G_1$ represents a nitrogen atom and $G_2$ represents a carbon atom.

In another embodiment, in the compound of formula (I) $G_2$ represents a nitrogen atom and $G_1$ represents a carbon atom.

Typically, in the compound of formula (I) $R_1$ represents a hydrogen atom, a halogen atom, a hydroxy group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a phenyl group, a 5- to 7-membered heteroaryl group containing one, two or three heteroatoms heteroatoms selected from O, S and N, a 5- to 7-membered, saturated N-containing heterocyclyl ring, which heterocyclyl ring is unsubstituted or substituted by one, two or three substituents selected from a halogen atom, a cyano group, a linear or branched $C_1$-$C_4$ alkyl group, a $C_1$-$C_4$ alkylsulfonyl group or a $C_3$-$C_7$ cycloalkyl group; or $R_1$ represents a —$(CH_2)_{0\text{-}2}OR_9$ group, a —O—$(CH_2)_{1\text{-}2}OR_9$ group, or a —$NR_8R_9$ group; wherein $R_8$ and $R_9$ are as defined above.

Preferably, $R_1$ represents a hydrogen atom, a halogen atom, a linear or branched $C_1$-$C_6$ alkyl group, a $C_3$-$C_7$ cycloalkyl group, a 5- to 7-membered, saturated N-containing heterocyclyl ring, which heterocyclyl ring is substituted by one, two or three substituents selected from a halogen atom, a cyano group, a linear or branched $C_1$-$C_4$ alkyl group, a $C_1$-$C_4$ alkylsulfonyl group or a $C_3$-$C_7$ cycloalkyl group; or $R_1$ represents a —$(CH_2)_{0\text{-}2}OR_9$ group, a —O—$(CH_2)_{7\text{-}2}OR_9$ group or a —$NR_8R_9$ group, wherein $R_8$ and $R_9$ independently represent a hydrogen atom or a linear or branched $C_1$-$C_3$ alkyl group.

More preferably $R_1$ represents a hydrogen atom, a linear or branched $C_1$-$C_3$ alkyl group, a 5- to 7-membered, saturated N-containing heterocyclyl ring, which heterocyclyl ring is substituted by a $C_1$-$C_4$ alkylsulfonyl group; or $R_1$ represents a —O—$(CH_2)_{1\text{-}2}OR_9$ group or a —$NR_8R_9$ group, wherein $R_8$ and $R_9$ independently represent a hydrogen atom or a linear or branched $C_1$-$C_3$ alkyl group. Most preferably $R_1$ represents a hydrogen atom or a methyl group.

Preferably, when $R_1$ represents a 5- to 7-membered, saturated N-containing heterocyclyl ring, said heterocyclyl group is a piperazinyl group linked to the rest of the molecule via a ring nitrogen atom, in other words it is linked to the group imidazo[1,2-b]pyridazine or imidazo[4,5-b]pyridine via a ring nitrogen atom. Substituents on the piperazinyl group may be present on any ring atom but are preferably present on the free nitrogen atom, i.e. the nitrogen atom which is not linked to the group imidazo[1,2-b]pyridazine or imidazo[4,5-b]pyridine. Preferred substituents of the piperazinyl group are a $C_1$-$C_4$ alkylsulfonyl group (preferably a methylsulfonyl group) and a —O—$(CH_2)_{1\text{-}2}$O—$CH_3$ group.

Typically, in the compound of formula (I) $R_2$ represents a hydrogen atom, a halogen atom, a hydroxy group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a phenyl group, a 5- to 7-membered heteroaryl group containing one, two or three heteroatoms selected from O, S and N, a 5- to 7-membered, saturated N-containing heterocyclyl ring, which heterocyclyl ring is unsubstituted or substituted by one, two or three substituents selected from a halogen atom, a cyano group, a linear or branched $C_1$-$C_4$ alkyl group, a $C_1$-$C_4$ alkylsulfonyl group or a $C_3$-$C_7$ cycloalkyl group; or $R_2$ represents a —$(CH_2)_{0-2}OR_9$ group, a —O—$(CH_2)_{1-2}OR_9$ group, or a —$NR_8R_9$ group; wherein $R_8$ and $R_9$ are as defined above.

Preferably $R_2$ represents a hydrogen atom, a halogen atom, a linear or branched $C_1$-$C_6$ alkyl group, a $C_3$-$C_7$ cycloalkyl group, a —$(CH_2)_{0-2}OR_9$ group, a —O—$(CH_2)_{1-2}OR_9$ group or a —$NR_8R_9$ group wherein $R_8$ and $R_9$ independently represent a hydrogen atom or a linear or branched $C_1$-$C_3$ alkyl group.

More preferably $R_2$ represents a hydrogen atom, a halogen atom, a linear or branched $C_1$-$C_3$ alkyl group or a —$NR_8R_9$ group wherein $R_8$ and $R_9$ independently represent a hydrogen atom or a linear or branched $C_1$-$C_3$ alkyl group. Most preferably $R_2$ represents a hydrogen atom or a methyl group.

For the avoidance of doubt, when $R_1$ represents a hydrogen atom, a halogen atom, a hydroxy, cyano, alkyl, haloalkyl, hydroxyalkyl, cycloalkyl, cycloalkenyl, aryl, heteroaryl, or heterocyclyl group, $R_2$ may represent a —$(CH_2)_{0-2}OR_9$ group, a —O—$(CH_2)_{1-2}OR_9$ group, or a —$NR_8R_9$ group. Likewise, when $R_1$ represents a —$(CH_2)_{0-2}OR_8$ group, a —O—$(CH_2)_{1-2}OR_9$ group, or a —$NR_8R_9$ group, $R_2$ may represent a hydrogen atom, a halogen atom, a hydroxy, cyano, alkyl, haloalkyl, hydroxyalkyl, cycloalkyl, cycloalkenyl, aryl, heteroaryl, or heterocyclyl group.

Typically, in the compound of formula (I) $R_3$ represents a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a monocyclic or polycyclic $C_6$-$C_{14}$ aryl group, a 5- to 7-membered heteroaryl group containing one, two or three heteroatoms selected from O, S and N, a 5- to 7-membered heterocyclyl group containing one, two or three heteroatoms selected from O, S and N, wherein the alkyl, haloalkyl, hydroxyalkyl, cycloalkyl, cycloalkenyl, aryl, heteroaryl, and heterocyclyl groups are unsubstituted or substituted by one or more substituents selected from a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a phenyl group, a pyridyl group, a pyrimidinyl group, a piperidyl group, a —$(CH_2)OR_9$ group, a —$NR_8R_9$ group, a —$C(O)$—$(CH_2)_n$—$R_8$ group, a —$C(O)$—$(CH_2)$, —$NR_8R_9$ group, a —$S(O)_2(CH_2)_nR_9$ group or a —$S(O)_2(CH_2)_nNR_8R_9$ group; wherein each n is 0, 1 or 2; and wherein $R_8$ and $R_9$ are as defined above.

Preferably, in the compound of formula (I) $R_3$ represents a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a phenyl group, a pyridyl group, a pyrimidinyl group or a piperidyl group, wherein the phenyl, pyridyl, pyrimidinyl or piperidyl groups are unsubstituted or substituted by one, two or three substituents selected from a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a phenyl group, a pyridyl group, a pyrimidinyl group, a piperidyl group, a —$(CH_2)OR_9$ group, a —$NR_8R_9$ group, a —$C(O)$—$(CH_2)_n$—$R_8$ group, a —$C(O)$—$(CH_2)_n$—$NR_8R_8$ group, a —$S(O)_2(CH_2)_nR_9$ group or a —$S(O)_2(CH_2)NR_8R_9$ group; wherein each n is 0, 1 or 2; and wherein $R_8$ and $R_9$ are as defined above.

More preferably, in the compound of formula (I) $R_3$ represents a phenyl group, a pyridyl group, a pyrimidinyl group or a piperidyl group.

Preferably, when $R_3$ is a phenyl group, it is unsubstituted or substituted by one, two or three substituents selected from a halogen atom (preferably a fluorine atom or a chlorine atom), a cyano group, a linear or branched $C_1$-$C_3$ alkyl group, a $C_1$-$C_4$ haloalkyl group (preferably a —$CHF_2$ group or a —$CF_3$ group), a $C_1$-$C_4$ hydroxyalkyl group or a $C_3$-$C_7$ cycloalkyl group.

Preferably, when $R_3$ is a pyridyl or pyrimidinyl group, said groups are linked to the rest of the molecule via a ring carbon atom, in other words they are linked to the group —$N(R_4)$—$(CR_5R_6)_m$— via a ring carbon atom. Pyridyl and pyrimidinyl groups are unsubstituted or substituted with one, two or three substituents selected from a halogen atom (preferably a fluorine atom or a chlorine atom), a cyano group, a linear or branched $C_1$-$C_3$ alkyl group, a $C_1$-$C_4$ haloalkyl group (preferably a —$CHF_2$ group or a —$CF_3$ group), a $C_1$-$C_4$ hydroxyalkyl group, a $C_3$-$C_7$ cycloalkyl group, a —$(CH_2)OR_9$ group, a —$NR_8R_9$ group, a —$C(O)$—$(CH_2)_n$—$R_8$ group, a —$C(O)$—$(CH_2)_n$—$NR_8R_9$ group, a —$S(O)_2(CH_2)_nR_9$ group or a —$S(O)_2(CH_2)_nNR_8R_9$ group; wherein each n is 0 or 1 and wherein $R_8$ is a nitrogen atom, a cyano group or a methyl group and $R_9$ is a nitrogen atom or a methyl group. More preferably, pyridyl and pyrimidinyl groups are substituted with one or two halogen atoms.

Substituents on a pyridyl or pyrimidinyl group may be present on any ring atom but are preferably present on a carbon atom.

Preferably, when $R_3$ is a piperidinyl group, it is linked to the rest of the molecule via a ring carbon atom, in other words it is linked to the group $N(R_4)$—$(CR_5R_6)_m$— via a ring carbon atom. Substituents on a piperidinyl group may be present on any ring atom but are preferably present on the nitrogen atom. Preferably, one substituent is present on the ring nitrogen atom. The other substituents, if present, are present on a carbon atom. More preferably, the piperidinyl group is substituted with one or two substituents selected from a halogen atom (preferably a fluorine atom or a chlorine atom) or a —$C(O)$—$(CH_2)$—$CN$ group. Most preferably, the piperidinyl group is substituted by a —$C(O)$—$(CH_2)$—$CN$ group on the nitrogen atom and, if other substituent is present, it is a halogen atom present on a carbon atom.

Typically, in the compound of formula (I), $R_4$ represents a hydrogen atom, a $C_1$-$C_4$ haloalkyl group, a $C_1$-$C_4$ hydroxyalkyl group or a linear or branched $C_1$-$C_6$ alkyl group. Preferably, $R_4$ represents a hydrogen atom, a $C_1$-$C_2$ haloalkyl group, a $C_1$-$C_2$ hydroxyalkyl group or a linear or branched $C_1$-$C_3$ alkyl group. More preferably, $R_4$ represents a hydrogen atom or a linear or branched $C_1$-$C_3$ alkyl group. Most preferably $R_4$ represents a hydrogen atom or a methyl group.

Typically, in the compound of formula (I), $R_5$ and $R_6$ each independently represent a hydrogen atom or a linear or branched $C_1$-$C_6$ alkyl group. Preferably, $R_5$ and $R_6$ each independently represent a hydrogen atom or a linear or branched $C_1$-$C_3$ alkyl group. More preferably, $R_5$ and $R_6$ each independently represent a hydrogen atom or a methyl group.

Typically, in the compound of formula (I), $R_7$ represents a represent a hydrogen atom, a halogen atom, a cyano group, a linear or branched $C_1$-$C_4$ alkyl group, a $C_1$-$C_4$ haloalkyl group, a $C_1$-$C_4$ hydroxyalkyl group, a $C_3$-$C_7$ cycloalkyl group, a phenyl group, a naphthyl group, a pyridyl group, a pyrimidinyl group or a piperidyl group, wherein the phenyl, naphthyl, pyridyl, pyrimidinyl or piperidyl groups are unsubstituted or substituted by one, two or three substituents selected from a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl, a phenyl group, a pyridyl group, a pyrimidinyl group or a piperidyl group.

Preferably, $R_7$ represents a hydrogen atom, a halogen atom, a cyano group, a linear or branched $C_1$-$C_3$ alkyl group, a $C_1$-$C_4$ haloalkyl group, a $C_1$-$C_4$ hydroxyalkyl group or a $C_3$-$C_7$ cycloalkyl group. More preferably, $R_7$ represents a hydrogen atom, a halogen atom (preferably a fluorine atom or a chlorine atom), a linear or branched $C_1$-$C_3$ alkyl group (preferably a methyl group) or a $C_1$-$C_4$ haloalkyl group (preferably a —$CHF_2$ group or a —$CF_3$ group).

Typically, when $R_1$, $R_2$, $R_3$ or $R_7$ is a said alkyl group substituted by one or more substituents, said one or more substituents do not include an alkyl group, a haloalkyl group or a hydroxyalkyl group.

Typically, when $R_1$, $R_2$, $R_3$ or $R_7$ is a said haloalkyl group substituted by one or more substituents, said one or more substituents do not include an alkyl group or a haloalkyl group.

Typically, when $R_1$, $R_2$, $R_3$ or $R_7$ is a said hydroxyalkyl group substituted by one or more substituents, said one or more substituents do not include an alkyl group or a hydroxyalkyl group.

Typically, in the compound of formula (I), m is 0, 1 or 2; preferably 0 or 1.

In a particularly preferred embodiment, in the compound of formula (I)

m is 0 or 1;

X is a nitrogen atom and Y is a —$CR_7$ group; or Y is a nitrogen atom and X is a —$CR_7$ group; or both X and Y are a —$CR_7$ group;

One of $G_1$ and $G_2$ represents a nitrogen atom and the other represents a carbon atom;

$R_1$ represents a hydrogen atom, a halogen atom, a linear or branched $C_1$-$C_6$ alkyl group, a $C_3$-$C_7$ cycloalkyl group, a 5- to 7-membered, saturated N-containing heterocyclyl ring, which heterocyclyl ring is substituted by a $C_1$-$C_4$ alkylsulfonyl group, or $R_1$ represents a —$(CH_2)_{0-2}OR_9$ group, a —$O(CH_2)_{1-2}OR_9$ group or a —$NR_8R_9$ group, wherein $R_8$ and $R_9$ independently represent a hydrogen atom or a linear or branched $C_1$-$C_3$ alkyl group;

$R_2$ represents a hydrogen atom, a halogen atom, a linear or branched $C_1$-$C_6$ alkyl group, a $C_3$-$C_7$ cycloalkyl group, a —$(CH_2)_{0-2}OR_9$ group, a —$O$—$(CH_2)_{1-2}OR_9$ group or a —$NR_8R_9$ group wherein $R_8$ and $R_9$ independently represent a hydrogen atom or a linear or branched $C_1$-$C_3$ alkyl group;

$R_3$ represents a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a monocyclic or polycyclic $C_6$-$C_{14}$ aryl group, a 5- to 7-membered heteroaryl group containing one, two or three heteroatoms selected from O, S and N, a 5- to 7-membered heterocyclyl group containing one, two or three heteroatoms selected from O, S and N, wherein the alkyl, haloalkyl, hydroxyalkyl, cycloalkyl, cycloalkenyl, aryl, heteroaryl, and heterocyclyl groups are unsubstituted or substituted by one, two or three substituents selected from a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl, a phenyl group, a pyridyl group, a pyrimidinyl group, a piperidyl group, a —$(CH_2)OR_9$ group, a —$NR_8R_9$ group, a —$C(O)$—$(CH_2)$—$R_8$ group, a —$C(O)$—$(CH_2)_n$—$NR_8R_9$ group, a —$S(O)_2(CH_2)_nR_9$ group or a —$S(O)_2(CH_2)_nNR_8R_9$ group; wherein each n is 0 or 1 and wherein $R_8$ is a hydrogen atom, a cyano group, or a linear or branched $C_1$-$C_3$ alkyl group, a $C_1$-$C_4$ haloalkyl group or a $C_3$-$C_7$ cycloalkyl group and $R_9$ is a hydrogen atom or a linear or branched $C_1$-$C_3$ alkyl group;

$R_4$ represents a hydrogen atom, a $C_1$-$C_4$ haloalkyl group, a $C_1$-$C_4$ hydroxyalkyl group or a linear or branched $C_1$-$C_6$ alkyl group;

$R_5$ and $R_6$ each independently represent a hydrogen atom or a linear or branched $C_1$-$C_3$ alkyl group;

$R_7$ represents a hydrogen atom, a halogen atom, a cyano group, a linear or branched $C_1$-$C_4$ alkyl group, a $C_1$-$C_4$ haloalkyl group, a $C_1$-$C_4$ hydroxyalkyl group, a $C_3$-$C_7$ cycloalkyl group, a phenyl group, a naphthyl group, a pyridyl group, a pyrimidinyl group or a piperidyl group, wherein the phenyl, naphthyl, pyridyl, pyrimidinyl or piperidyl groups are unsubstituted or substituted by one, two or three substituents selected from a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl, a phenyl group, a pyridyl group, a pyrimidinyl group or a piperidyl group.

In a further particular preferred embodiment, in the compound of formula (I):

m is 0 or 1;

X is a nitrogen atom and Y is a —$CR_7$ group; or Y is a nitrogen atom and X is a —$CR_7$ group; or both X and Y are a —$CR_7$ group;

One of $G_1$ and $G_2$ represents a nitrogen atom and the other represents a carbon atom;

$R_1$ represents a hydrogen atom, a halogen atom, a linear or branched $C_1$-$C_3$ alkyl group, a 5- to 7-membered, saturated N-containing heterocyclyl ring, which heterocyclyl ring is substituted by a $C_1$-$C_4$ alkylsulfonyl group or $R_1$ represents a —$O$—$(CH_2)_{1-2}OR_9$ group, wherein $R_9$ represents a $C_1$-$C_3$ alkyl group;

$R_2$ represents a hydrogen atom, a halogen atom or a linear or branched $C_1$-$C_3$ alkyl group;

$R_3$ represents a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a phenyl group, a pyridyl group, a pyrimidinyl group or a piperidinyl group, wherein the phenyl, pyridyl, pyrimidinyl or piperidinyl groups are unsubstituted or substituted by one or more substituents selected from a halogen atom, a cyano group, a linear or branched $C_1$-$C_3$ alkyl group, a $C_1$-$C_4$ haloalkyl group, a $C_1$-$C_4$ hydroxyalkyl group, a $C_3$-$C_7$ cycloalkyl, or a —$C(O)$—$(CH_2)$—$R_8$ group, wherein n is 0 or 1 and wherein $R_8$ is a cyano group, a linear or branched $C_1$-$C_3$ alkyl group, a $C_1$-$C_4$ haloalkyl group or a $C_3$-$C_7$ cycloalkyl group;

$R_4$ represents a hydrogen atom or a methyl group;

$R_5$ and $R_6$ each independently represent a hydrogen atom or a methyl group;

$R_7$ represents a hydrogen atom, a halogen atom, a cyano group, a linear or branched $C_1$-$C_3$ alkyl group, a $C_1$-$C_4$ haloalkyl group, a $C_1$-$C_4$ hydroxyalkyl group or a $C_3$-$C_7$ cycloalkyl group.

In a further particular preferred embodiment, in the compound of formula (I):

m is 0 or 1;

X is a nitrogen atom and Y is a —$CR_7$ group: or Y is a nitrogen atom and X is a —$CR_7$ group; or both X and Y are a —$CR_7$ group;

One of $G_1$ and $G_2$ represents a nitrogen atom and the other represents a carbon atom;

$R_1$ represents a hydrogen atom, a linear or branched $C_1$-$C_3$ alkyl group, a 5- to 7-membered, saturated N-containing heterocyclyl ring, which heterocyclyl ring is substituted by a $C_1$-$C_4$ alkylsulfonyl group or $R_1$ represents a —O—$(CH_2)_{1-2}$ $OR_8$ group, wherein $R_9$ represents a $C_1$-$C_3$ alkyl group;

$R_2$ represents a hydrogen atom, or a linear or branched $C_1$-$C_3$ alkyl group;

$R_3$ represents a phenyl group, a pyridyl group, a pyrimidinyl group or a piperidinyl group, wherein the phenyl, pyridyl, pyrimidinyl or piperidinyl groups are unsubstituted or substituted by one or more substituents selected from a halogen atom, or a —C(O)—$(CH_2)_n$—$R_8$ group, wherein n is 0 or 1 and wherein and $R_8$ is a cyano group;

$R_4$ represents a hydrogen atom;

$R_5$ and $R_6$ each independently represent a hydrogen atom or a methyl group;

$R_7$ represents a hydrogen atom, a halogen atom, a linear or branched $C_1$-$C_3$ alkyl group, or a $C_1$-$C_4$ haloalkyl group.

In one embodiment, the compound of formula (I) is one of formula (I-a):

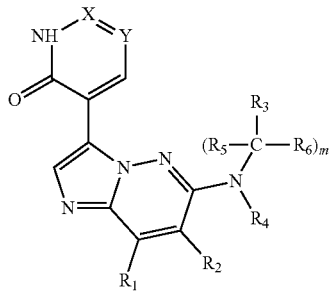

Formula (I-a)

wherein m, X, Y and $R_1$ to $R_9$ are as defined above.

In a preferred embodiment, in the compound of formula (I-a):

m is 0 or 1;

X is a nitrogen atom and Y is a —$CR_7$ group; or Y is a nitrogen atom and X is a —$CR_7$ group; or both X and Y are a —$CR_7$ group; preferably X is a nitrogen atom and Y is a —$CR_7$ group; or both X and Y are a —$CR_7$ group;

$R_1$ represents a hydrogen atom, a halogen atom, a linear or branched $C_1$-$C_6$ alkyl group, a $C_3$-$C_7$ cycloalkyl group, a 5- to 7-membered, saturated N-containing heterocyclyl ring, which heterocyclyl ring is substituted by a $C_1$-$C_4$ alkylsulfonyl group, or $R_1$ represents a —$(CH_2)_{0-2}OR_9$ group, a —O—$(CH_2)_{1-2}OR_9$ group or a —$NR_8R_9$ group, wherein $R_8$ and $R_9$ independently represent a hydrogen atom or a linear or branched $C_1$-$C_3$ alkyl group;

$R_2$ represents a hydrogen atom, a halogen atom, a linear or branched $C_1$-$C_6$ alkyl group, a $C_3$-$C_7$ cycloalkyl group, a —$(CH_2)_{1-2}OR_9$ group, a —O—$(CH_2)_{1-2}OR_9$ group or a —$NR_8R_9$ group wherein $R_8$ and $R_9$ independently represent a hydrogen atom or a linear or branched $C_1$-$C_3$ alkyl group;

$R_3$ represents a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a monocyclic or polycyclic $C_6$-$C_{14}$ aryl group, a 5- to 7-membered heteroaryl group containing one, two or three heteroatoms selected from O, S and N, a 5- to 7-membered heterocyclyl group containing one, two or three heteroatoms selected from O, S and N, wherein the alkyl, haloalkyl, hydroxyalkyl, cycloalkyl, cycloalkenyl, aryl, heteroaryl, and heterocyclyl groups are unsubstituted or substituted by one, two or three substituents selected from a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl, a phenyl group, a pyridyl group, a pyrimidinyl group, a piperidyl group, a —$(CH_2)_nOR_9$ group, a —$NR_8R_9$ group, a —C(O)—$(CH_2)_n$—$R_8$ group, a —C(O)—$(CH_2)_n$—$NR_8R_9$ group, a —$S(O)_2(CH_2)_nR_9$ group or a —$S(O)_2(CH_2)_nNR_8R_9$ group; wherein each n is 0 or 1 and wherein $R_8$ is a hydrogen atom, a cyano group, or a linear or branched $C_1$-$C_3$ alkyl group, a $C_1$-$C_4$ haloalkyl group or a $C_3$-$C_7$ cycloalkyl group and $R_9$ is a hydrogen atom or a linear or branched $C_1$-$C_3$ alkyl group;

$R_4$ represents a hydrogen atom, a $C_1$-$C_4$ haloalkyl group, a $C_1$-$C_4$ hydroxyalkyl group or a linear or branched $C_1$-$C_6$ alkyl group;

$R_5$ and $R_6$ each independently represent a hydrogen atom or a linear or branched $C_1$-$C_3$ alkyl group;

$R_7$ represents a hydrogen atom, a halogen atom, a cyano group, a linear or branched $C_1$-$C_4$ alkyl group, a $C_1$-$C_4$ haloalkyl group, a $C_1$-$C_4$ hydroxyalkyl group, a $C_3$-$C_7$ cycloalkyl group, a phenyl group, a naphthyl group, a pyridyl group, a pyrimidinyl group or a piperidyl group, wherein the phenyl, naphthyl, pyridyl, pyrimidinyl or piperidyl groups are unsubstituted or substituted by one, two or three substituents selected from a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl, a phenyl group, a pyridyl group, a pyrimidinyl group or a piperidyl group.

In a further particular preferred embodiment, in the compound of formula (I-a):

m is 0 or 1;

X is a nitrogen atom and Y is a —$CR_7$ group; or Y is a nitrogen atom and X is a —$CR_7$ group; or both X and Y are a —$CR_7$ group; preferably X is a nitrogen atom and Y is a —$CR_7$ group; or both X and Y are a —$CR_7$ group;

$R_1$ represents a hydrogen atom, a halogen atom, a linear or branched $C_1$-$C_3$ alkyl group, a 5- to 7-membered, saturated N-containing heterocyclyl ring, which heterocyclyl ring is substituted by a $C_1$-$C_4$ alkylsulfonyl group or $R_1$ represents a —O—$(CH_2)_{1-2}OR_8$ group, wherein $R_9$ represents a $C_1$-$C_3$ alkyl group;

$R_2$ represents a hydrogen atom, a halogen atom or a linear or branched $C_1$-$C_3$ alkyl group;

$R_3$ represents a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a phenyl group, a pyridyl group, a pyrimidinyl group or a piperidinyl group, wherein the phenyl, pyridyl, pyrimidinyl or piperidinyl groups are unsubstituted or substituted by one or more substituents selected from a halogen atom, a cyano group, a linear or branched $C_1$-$C_3$ alkyl group, a $C_1$-$C_4$ haloalkyl group, a $C_1$-$C_4$ hydroxyalkyl group, a $C_3$-$C_7$ cycloalkyl, or a —C(O)—$(CH_2)_n$—$R_8$ group, wherein n is 0 or 1 and wherein and $R_8$ is a cyano group, a linear or branched $C_1$-$C_3$ alkyl group, a $C_1$-$C_4$ haloalkyl group or a $C_3$-$C_7$ cycloalkyl group;

$R_4$ represents a hydrogen atom or a methyl group;

$R_5$ and $R_6$ each independently represent a hydrogen atom or a methyl group;

$R_7$ represents a hydrogen atom, a halogen atom, a cyano group, a linear or branched $C_1$-$C_3$ alkyl group, a $C_1$-$C_4$ haloalkyl group, a $C_1$-$C_4$ hydroxyalkyl group or a $C_3$-$C_7$ cycloalkyl group.

In another embodiment, the compound of formula (I) is one of formula (I-b):

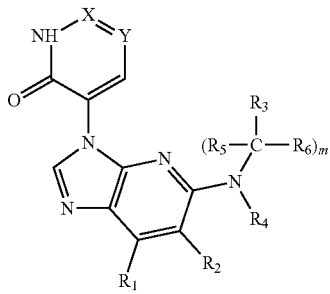

Formula (I-b)

wherein m, X, Y and $R_1$ to $R_9$ are as defined above.

In a preferred embodiment, in the compound of formula (I-b):

m is 0 or 1;

X is a nitrogen atom and Y is a —$CR_7$ group; or Y is a nitrogen atom and X is a —$CR_7$ group; or both X and Y are a —$CR_7$ group; preferably X is a nitrogen atom and Y is a —$CR_7$ group; or both X and Y are a —$CR_7$ group;

$R_1$ represents a hydrogen atom, a halogen atom, a linear or branched $C_1$-$C_6$ alkyl group, a $C_3$-$C_7$ cycloalkyl group, a 5- to 7-membered, saturated N-containing heterocyclyl ring, which heterocyclyl ring is substituted by a $C_1$-$C_4$ alkylsulfonyl group, or $R_1$ represents a —$(CH_2)_{0-2}OR_9$ group, a —O—$(CH_2)_{1-2}OR_9$ group or a —$NR_8R_9$ group, wherein $R_8$ and $R_9$ independently represent a hydrogen atom or a linear or branched $C_1$-$C_3$ alkyl group;

$R_2$ represents a hydrogen atom, a halogen atom, a linear or branched $C_1$-$C_6$ alkyl group, a $C_3$-$C_7$ cycloalkyl group, a —$(CH_2)_{0-2}OR_9$ group, a —O—$(CH_2)_{1-2}OR_9$ group or a —$NR_8R_9$ group wherein $R_8$ and $R_9$ independently represent a hydrogen atom or a linear or branched $C_1$-$C_3$ alkyl group;

$R_3$ represents a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a monocyclic or polycyclic $C_6$-$C_{14}$ aryl group, a 5- to 7-membered heteroaryl group containing one, two or three heteroatoms selected from O, S and N, a 5- to 7-membered heterocyclyl group containing one, two or three heteroatoms selected from O, S and N, wherein the alkyl, haloalkyl, hydroxyalkyl, cycloalkyl, cycloalkenyl, aryl, heteroaryl, and heterocyclyl groups are unsubstituted or substituted by one, two or three substituents selected from a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl, a phenyl group, a pyridyl group, a pyrimidinyl group, a piperidyl group, a —$(CH_2)_nOR_9$ group, a —$NR_8R_9$ group, a —$C(O)$—$(CH_2)_n$—$R_8$ group, a —$C(O)$—$(CH_2)_n$—$NR_8R_9$ group, a —$S(O)_2(CH_2)_nR_9$ group or a —$S(O)_2(CH_2)NR_8R_9$ group; wherein each n is 0 or 1 and wherein $R_8$ is a hydrogen atom, a cyano group, or a linear or branched $C_1$-$C_3$ alkyl group, a $C_1$-$C_4$ haloalkyl group or a $C_3$-$C_7$ cycloalkyl group and $R_9$ is a hydrogen atom or a linear or branched $C_1$-$C_3$ alkyl group;

$R_4$ represents a hydrogen atom, a $C_1$-$C_4$ haloalkyl group, a $C_1$-$C_4$ hydroxyalkyl group or a linear or branched $C_1$-$C_6$ alkyl group;

$R_5$ and $R_6$ each independently represent a hydrogen atom or a linear or branched $C_1$-$C_3$ alkyl group;

$R_7$ represents a hydrogen atom, a halogen atom, a cyano group, a linear or branched $C_1$-$C_4$ alkyl group, a $C_1$-$C_4$ haloalkyl group, a $C_1$-$C_4$ hydroxyalkyl group, a $C_3$-$C_7$ cycloalkyl group, a phenyl group, a naphthyl group, a pyridyl group, a pyrimidinyl group or a piperidyl group, wherein the phenyl, naphthyl, pyridyl, pyrimidinyl or piperidyl groups are unsubstituted or substituted by one, two or three substituents selected from a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl, a phenyl group, a pyridyl group, a pyrimidinyl group or a piperidyl group.

In a further particular preferred embodiment, in the compound of formula (I-b):

m is 0 or 1;

X is a nitrogen atom and Y is a —$CR_7$ group; or Y is a nitrogen atom and X is a —$CR_7$ group; or both X and Y are a —$CR_7$ group; preferably X is a nitrogen atom and Y is a —$CR_7$ group; or both X and Y are a —$CR_7$ group;

$R_1$ represents a hydrogen atom, a halogen atom, a linear or branched $C_1$-$C_3$ alkyl group, a 5- to 7-membered, saturated N-containing heterocyclyl ring, which heterocyclyl ring is substituted by a $C_1$-$C_4$ alkylsulfonyl group or $R_1$ represents a —O—$(CH_2)_{1-2}OR_9$ group, wherein $R_9$ represents a $C_1$-$C_3$ alkyl group;

$R_2$ represents a hydrogen atom, a halogen atom or a linear or branched $C_1$-$C_3$ alkyl group;

$R_3$ represents a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a phenyl group, a pyridyl group, a pyrimidinyl group or a piperidinyl group, wherein the phenyl, pyridyl, pyrimidinyl or piperidinyl groups are unsubstituted or substituted by one or more substituents selected from a halogen atom, a cyano group, a linear or branched $C_1$-$C_3$ alkyl group, a $C_1$-$C_4$ haloalkyl group, a $C_1$-$C_4$ hydroxyalkyl group, a $C_3$-$C_7$ cycloalkyl, or a —$C(O)$—$(CH_2)_n$—$R_8$ group, wherein n is 0 or 1 and wherein and $R_8$ is a cyano group, a linear or branched $C_1$-$C_3$ alkyl group, a $C_1$-$C_4$ haloalkyl group or a $C_3$-$C_7$ cycloalkyl group;

$R_4$ represents a hydrogen atom or a methyl group;

$R_5$ and $R_6$ each independently represent a hydrogen atom or a methyl group;

$R_7$ represents a hydrogen atom, a halogen atom, a cyano group, a linear or branched $C_1$-$C_3$ alkyl group, a $C_1$-$C_4$ haloalkyl group, a $C_1$-$C_4$ hydroxyalkyl group or a $C_3$-$C_7$ cycloalkyl group.

Particular individual compounds of the invention include:

3-oxo-3-((3R)-3-{[3-(2-oxo-1,2-dihydropyridin-3-yl)imidazo[1,2-b]pyridazin-6-yl]amino}piperidin-1-yl)propanenitrile;

3-(6-{[(1S)-1-Phenylethyl]amino}imidazo[1,2-b]pyridazin-3-yl)pyridin-2(1H)-one;

3-(6-{[(1S)-1-(5-Fluoropyridin-2-yl)ethyl]amino}imidazo[1,2-b]pyridazin-3-yl)pyridin-2(1H)-one;

3-(6-{[(1R)-1-(5-Fluoropyridin-2-yl)ethyl]amino}imidazo[1,2-b]pyridazin-3-yl)pyridin-2(1H)-one;

3-(6-{[(1S)-1-(5-Fluoropyrimidin-2-yl)ethyl]amino}imidazo[1,2-b]pyridazin-3-yl)pyridin-2(1H)-one;

4-(6-{[(1S)-1-Phenylethyl]amino}imidazo[1,2-b]pyridazin-3-yl)pyridazin-3(2H)-one;

5-Fluoro-3-(6-{[(1S)-1-(5-fluoropyridin-2-yl)ethyl]amino}imidazo[1,2-b]pyridazin-3-yl)pyridin-2(1H)-one;

5-Chloro-3-(6-{[(1S)-1-(5-fluoropyridin-2-yl)ethyl]amino}imidazo[1,2-b]pyridazin-3-yl)pyridin-2(1H)-one;

3-(6-{[(1S)-1-(5-Fluoropyridin-2-yl)ethyl]amino}-7-methylimidazo[1,2-b]pyridazin-3-yl)pyridin-2(1H)-one 5-Fluoro-3-(6-{[(1S)-1-(5-fluoropyridin-2-yl)ethyl]amino}-7-methylimidazo[1,2-b]pyridazin-3-yl)pyridin-2(1H)-one;

(S)-5-fluoro-3-(6-(1-(5-fluoropyrimidin-2-yl)ethylamino)imidazo[1,2-b]pyridazin-3-yl)pyridin-2(1H)-one;

(S)-3-(5-(1-(5-fluoropyridin-2-yl)ethylamino)-3H-imidazo[4,5-b]pyridin-3-yl)pyridin-2(1H)-one;

(S)-5-chloro-3-(5-(1-(5-fluoropyridin-2-yl)ethylamino)-3H-imidazo[4,5-b]pyridin-3-yl)pyridin-2(1H)-one;

(S)-5-chloro-3-(5-(1-(5-fluoropyridin-2-yl)ethylamino)-6-methyl-3H-imidazo[4,5-b]pyridin-3-yl)pyridin-2(1H)-one;

(S)-5-(difluoromethyl)-3-(6-(1-(5-fluoropyridin-2-yl)ethylamino)imidazo[1,2-b]pyridazin-3-yl)pyridin-2(1H)-one;

(S)-3-(6-(1-(5-fluoropyridin-2-yl)ethylamino)imidazo[1,2-b]pyridazin-3-yl)-5-methylpyridin-2(1H)-one;

(S)-3-(6-(1-(5-fluoropyridin-2-yl)ethylamino)-8-(2-methoxyethoxy)imidazo[1,2-b]pyridazin-3-yl)pyridin-2(1H)-one;

(S)-3-(6-(1-(5-fluoropyridin-2-yl)ethylamino)-8-(4-(methylsulfonyl)piperazin-1-yl)imidazo[1,2-b]pyridazin-3-yl)pyridin-2(1H)-one;

(S)-3-(6-(1-(5-fluoropyrimidin-2-yl)ethylamino)-7-methylimidazo[1,2-b]pyridazin-3-yl)pyridin-2(1H)-one;

(S)-5-fluoro-3-(6-(1-(5-fluoropyrimidin-2-yl)ethylamino)-7-methylimidazo[1,2-b]pyridazin-3-yl)pyridin-2(1H)-one;

(S)-6-(6-(1-(5-fluoropyridin-2-yl)ethylamino)imidazo[1,2-b]pyridazin-3-yl)pyrimidin-4(3H)-one;

and pharmaceutically acceptable salts, solvates, N-oxides, stereoisomers, deuterated derivatives and tautomers thereof.

Examples of the preferred compounds are:

3-oxo-3-((3R)-3-{[3-(2-oxo-1,2-dihydropyridin-3-yl)imidazo[1,2-b]pyridazin-6-yl]amino}piperidin-1-yl)propanenitrile;

3-(6-{[(1S)-1-Phenylethyl]amino}imidazo[1,2-b]pyridazin-3-yl)pyridin-2(1H)-one;

3-(6-{[(1S)-1-(5-Fluoropyridin-2-yl)ethyl]amino}imidazo[1,2-b]pyridazin-3-yl)pyridin-2(1H)-one;

3-(6-{[(1R)-1-(5-Fluoropyridin-2-yl)ethyl]amino}imidazo[1,2-b]pyridazin-3-yl)pyridin-2(1H)-one;

3-(6-{[(1S)-1-(5-Fluoropyrimidin-2-yl)ethyl]amino}imidazo[1,2-b]pyridazin-3-yl)pyridin-2(1H)-one;

4-(6-{[(1S)-1-Phenylethyl]amino}imidazo[1,2-b]pyridazin-3-yl)pyridazin-3(2H)-one;

5-Fluoro-3-(6-{[(1S)-1-(5-fluoropyridin-2-yl)ethyl]amino}imidazo[1,2-b]pyridazin-3-yl)pyridin-2(1H)-one;

5-Chloro-3-(6-{[(1S)-1-(5-fluoropyridin-2-yl)ethyl]amino}imidazo[1,2-b]pyridazin-3-yl)pyridin-2(1H)-one;

3-(6-{[(1S)-1-(5-Fluoropyridin-2-yl)ethyl]amino}-7-methylimidazo[1,2-b]pyridazin-3-yl)pyridin-2(1H)-one;

5-Fluoro-3-(6-{[(1S)-1-(5-fluoropyridin-2-yl)ethyl]amino}-7-methylimidazo[1,2-b]pyridazin-3-yl)pyridin-2(1H)-one;

(S)-5-fluoro-3-(6-(1-(5-fluoropyrimidin-2-yl)ethylamino)imidazo[1,2-b]pyridazin-3-yl)pyridin-2(1H)-one;

(S)-3-(5-(1-(5-fluoropyridin-2-yl)ethylamino)-3H-imidazo[4,5-b]pyridin-3-yl)pyridin-2(1H)-one;

(S)-5-chloro-3-(5-(1-(5-fluoropyridin-2-yl)ethylamino)-3H-imidazo[4,5-b]pyridin-3-yl)pyridin-2(1H)-one;

(S)-5-chloro-3-(5-(1-(5-fluoropyridin-2-yl)ethylamino)-6-methyl-3H-imidazo[4,5-b]pyridin-3-yl)pyridin-2(1H)-one;

and pharmaceutically acceptable salts, solvates, N-oxides, or stereoisomers, deuterated derivatives and tautomers thereof.

In one embodiment, particular compounds of the invention include

3-Oxo-((3R)-3-{[3-(2-oxo-1,2-dihydropyridin-3-yl)imidazo[1,2-b]pyridazin-6-yl]amino}piperidin-1-yl)propanenitrile;

3-(6-{[(1S)-1-Phenylethyl]amino}imidazo[1,2-b]pyridazin-3-yl)pyridin-2(1H)-one;

3-(6-{[(1S)-1-(5-Fluoropyridin-2-yl)ethyl]amino}imidazo[1,2-b]pyridazin-3-yl)pyridin-2(1H)-one;

3-(6-{[(1R)-1-(5-Fluoropyridin-2-yl)ethyl]amino}imidazo[1,2-b]pyridazin-3-yl)pyridin-2(1H)-one;

3-(6-{[(1S)-1-(5-Fluoropyrimidin-2-yl)ethyl]amino}imidazo[1,2-b]pyridazin-3-yl)pyridin-2(1H)-one;

4-(6-{[(1S)-1-Phenylethyl]amino}imidazo[1,2-b]pyridazin-3-yl)pyridazin-3(2H)-one;

5-Fluoro-3-(6-{[(1S)-1-(5-fluoropyridin-2-yl)ethyl]amino}imidazo[1,2-b]pyridazin-3-yl)pyridin-2(1H)-one;

5-Chloro-3-(6-{[(1S)-1-(5-fluoropyridin-2-yl)ethyl]amino}imidazo[1,2-b]pyridazin-3-yl)pyridin-2(1H)-one;

3-(6-{[(1S)-1-(5-Fluoropyridin-2-yl)ethyl]amino}-7-methylimidazo[1,2-b]pyridazin-3-yl)pyridin-2(1H)-one;

5-Fluoro-3-(6-{[(1S)-1-(5-fluoropyridin-2-yl)ethyl]amino}-7-methylimidazo[1,2-b]pyridazin-3-yl)pyridin-2(1H)-one;

(S)-5-(difluoromethyl)-3-(6-(1-(5-fluoropyridin-2-yl)ethylamino)imidazo[1,2-b]pyridazin-3-yl)pyridin-2(1H)-one;

(S)-3-(6-(1-(5-fluoropyridin-2-yl)ethylamino)imidazo[1,2-b]pyridazin-3-yl)-5-methylpyridin-2(1H)-one;

(S)-3-(6-(1-(5-fluoropyridin-2-yl)ethylamino)-8-(2-methoxyethoxy)imidazo[1,2-b]pyridazin-3-yl)pyridin-2(1H)-one;

(S)-3-(6-(1-(5-fluoropyridin-2-yl)ethylamino)-8-(4-(methylsulfonyl)piperazin-1-yl)imidazo[1,2-b]pyridazin-3-yl)pyridin-2(1H)-one;

(S)-3-(6-(1-(5-fluoropyrimidin-2-yl)ethylamino)-7-methylimidazo[1,2-b]pyridazin-3-yl)pyridin-2(1H)-one;

(S)-5-fluoro-3-(6-(1-(5-fluoropyrimidin-2-yl)ethylamino)imidazo[1,2-b]pyridazin-3-yl)pyridin-2(1H)-one;

(S)-5-fluoro-3-(6-(1-(5-fluoropyrimidin-2-yl)ethylamino)-7-methylimidazo[1,2-b]pyridazin-3-yl)pyridin-2(1H)-one;

and pharmaceutically acceptable salts, solvates, N-oxides, stereoisomers and deuterated derivatives thereof.

Examples of the preferred compounds in this embodiment are:

3-oxo-3-((3R)-3-{[3-(2-oxo-1,2-dihydropyridin-3-yl)imidazo[1,2-b]pyridazin-6-yl]amino}piperidin-1-yl)propanenitrile;

3-(6-{[(1S)-1-Phenylethyl]amino}imidazo[1,2-b]pyridazin-3-yl)pyridin-2(1H)-one;

3-(6-{[(1S)-1-(5-Fluoropyridin-2-yl)ethyl]amino}imidazo[1,2-b]pyridazin-3-yl)pyridin-2(1H)-one;

3-(6-{[(1R)-1-(5-Fluoropyridin-2-yl)ethyl]amino}imidazo[1,2-b]pyridazin-3-yl)pyridin-2(1H)-one;

3-(6-{[(1S)-1-(5-Fluoropyrimidin-2-yl)ethyl]amino}imidazo[1,2-b]pyridazin-3-yl)pyridin-2(1H)-one;

4-(6-{[(1S)-1-Phenylethyl]amino}imidazo[1,2-b]pyridazin-3-yl)pyridazin-3(2H)-one;

5-Fluoro-3-(6-{[(1S)-1-(5-fluoropyridin-2-yl)ethyl]amino}imidazo[1,2-b]pyridazin-3-yl)pyridin-2(1H)-one;

5-Chloro-3-(6-{[(1S)-1-(5-fluoropyridin-2-yl)ethyl]amino}imidazo[1,2-b]pyridazin-3-yl)pyridin-2(1H)-one;

3-(6-{[(1S)-1-(5-Fluoropyridin-2-yl)ethyl]amino}-7-methylimidazo[1,2-b]pyridazin-3-yl)pyridin-2(1H)-one;

5-Fluoro-3-(6-{[(1S)-1-(5-fluoropyridin-2-yl)ethyl]amino}-7-methylimidazo[1,2-b]pyridazin-3-yl)pyridin-2(1H)-one;

and pharmaceutically acceptable salts, solvates, N-oxides, stereoisomers and deuterated derivatives thereof.

According to one embodiment of the present invention, compounds of general sub-Formula (I-a) may be prepared by the following synthetic route as illustrated in Scheme 1.

Scheme 1

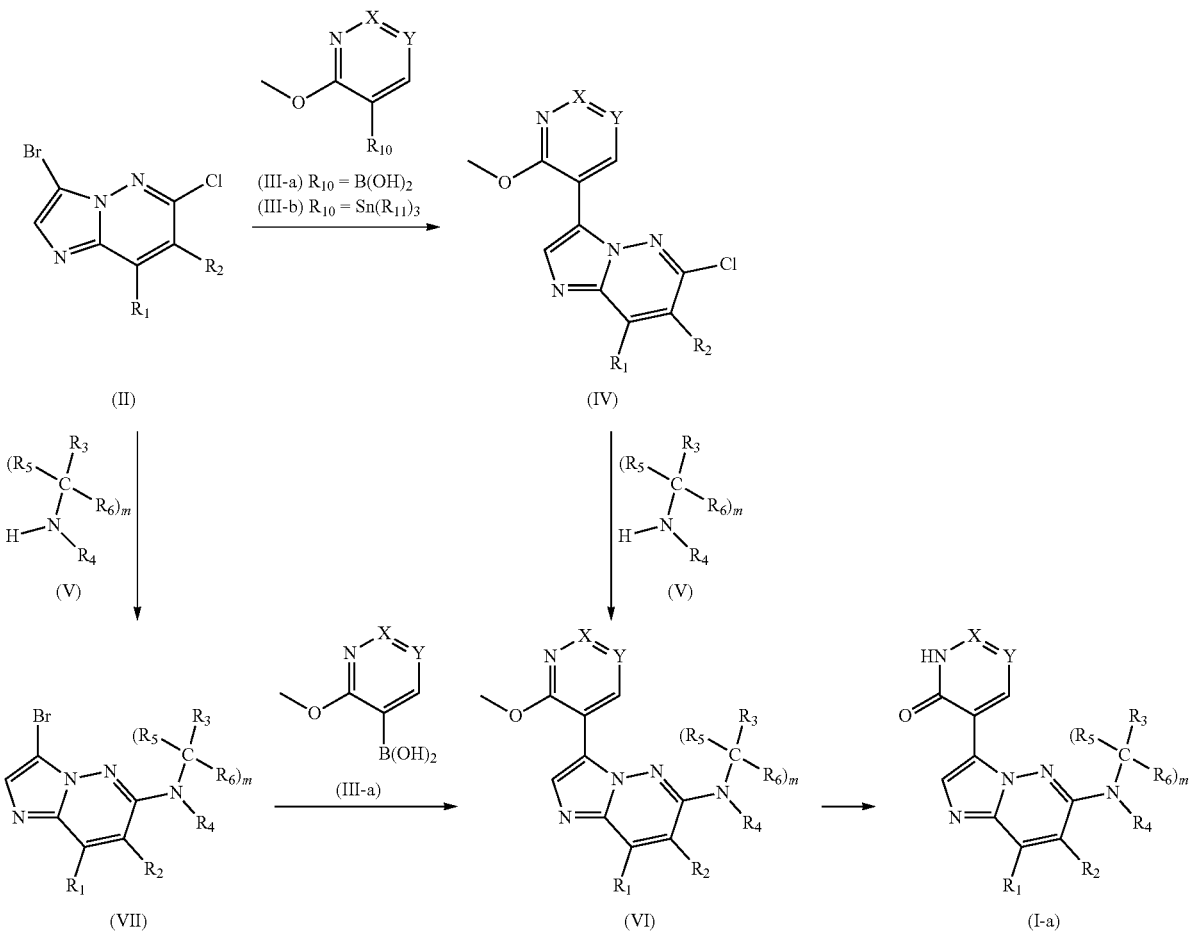

Compounds of sub-Formula (I-a) may be obtained from methoxy derivatives of Formula (VI) by reaction with suitable reagents such as trimethylsilylchloride/sodium iodide in a suitable solvent such as acetonitrile at reflux. Compounds of Formula (VI) may be prepared by reaction of chloroimidazopyridazines of Formula (IV) with amines of Formula (V) using a suitable catalyst such as tris(dibencylidenoacetone)dipalladium(0), in the presence of a ligand such as 2'-(dicyclohexylphosphino)-N,N-dimethylbiphenyl-2-amine, and a base, for example sodium tert-butoxide, in a solvent such as toluene at a temperature ranging from 80° C. to reflux.

Heteroaryl intermediates of Formula (III) (where $R_{10}$ represents a boronic acid or a trialkyl tin residue such as tributyltin) may be reacted with dihaloderivatives of Formula (II) under palladium-catalyzed coupling conditions with a suitable catalyst to furnish compounds of Formula (IV).

In a particular case, compounds of sub-Formula (III-a) in which $R_{10}$ represents a boronic acid ($R_{10}$=B(OH)$_2$) may be reacted with dihaloderivatives of Formula (II) under Suzuki-Miyaura reaction conditions (Miyaura, N.; Suzuki, A. Chem. Rev. 1995, 95, 2457) to give compounds of Formula (IV). Such reactions may be catalyzed by a suitable palladium catalyst such as [1,1'-bis(diphenylphosphino)ferrocene]-dichloropalladium(II) complex with dichloromethane (1:1) in a solvent such as 1,4-dioxane, in the presence of a base such as cesium carbonate, at temperatures ranging from 80° C. to reflux with or without the use of microwave irradiation.

In another particular case, compounds of sub-Formula (III-b), in which $R_{10}$ represents a trialkyltin moiety, where $R_{11}$ represents a $C_1$-$C_6$ alkyl group such as a n-butyl group ($R_{10}$=Sn($R_{11}$)$_3$), may be reacted with dihaloderivatives of Formula (II) in the presence of a suitable catalyst such as tetrakis(triphenylphosphine)palladium(0) and copper(I) iodide in a solvent such as N,N-dimethylformamide at temperatures ranging from 80-130° C. with or without the use of microwave irradiation to give compounds of Formula (IV).

In another synthetic pathway, compounds of Formula (VI) may be prepared by reaction of bromoderivatives of Formula (VII) with boronic acids of Formula (III-a) under Suzuki-Miyaura reaction conditions. Such reactions may be catalyzed by a suitable palladium catalyst such as [1,1'-bis(diphenylphosphino)ferrocene]-dichloropalladium(II) complex with dichloromethane (1:1) in a solvent such as 1,4-dioxane, in the presence of a base such as cesium carbonate, at temperatures ranging from 80° C. to reflux with or without the use of microwave irradiation.

Treatment of compounds of Formula (II) with amines of Formula (V), in the presence of a base, such as cesium fluoride, in a solvent such as dimethylsulfoxide, at temperatures ranging from 100 to 180° C. in a sealed tube gives rise to bromoderivatives of Formula (VII).

Intermediate halogenated imidazopyridazines of Formula (II) may be prepared by the following synthetic route as illustrated in Scheme 2:

Scheme 2

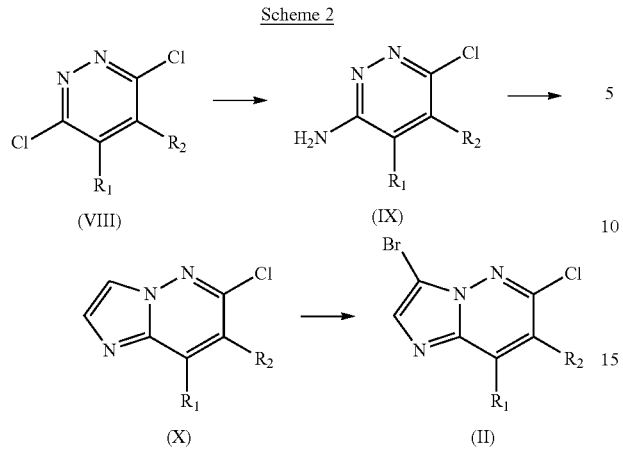

Reaction of dichloropyridazines of Formula (VIII) with aqueous ammonia in a solvent such as ethanol at 100° C. in a sealed tube furnishes amino derivatives of Formula (IX). Treatment of aminopyridazines of Formula (IX) with a suitable alkylating agent such as 2-chloro- or 2-bromoacetaldehyde in a suitable solvent such as n-butanol at temperatures ranging from 60 to 130° C. gives rise to imidazopyridazines of Formula (X). Compounds of Formula (X) may be transformed into dihaloderivatives of Formula (II) by treatment with a brominating reagent such as bromine in a solvent such as acetic acid at ambient temperature.

Heteroaryl intermediates of Formulae (III-a) and (III-b) may be prepared by the following synthetic route as illustrated in Scheme 3:

Scheme 3

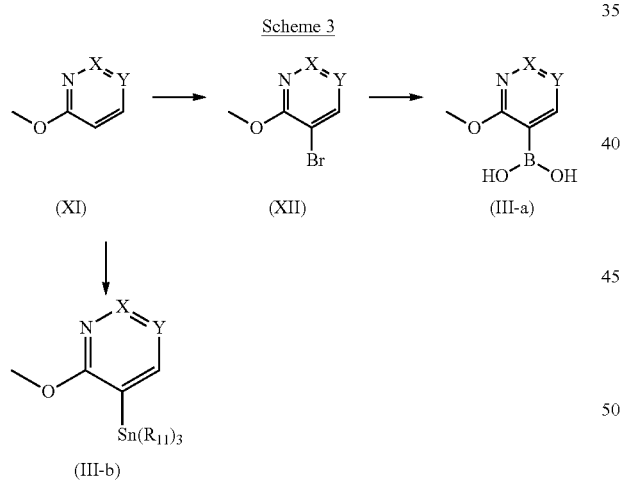

In a particular case, reaction of methoxy derivatives of Formula (XI) with a brominating agent, such as bromine, in the presence of a suitable base, such as sodium acetate, in a suitable solvent such as acetic acid at temperatures ranging from ambient temperature to 100° C. gives rise to bromoderivatives of Formula (XII). Compounds of Formula (XII) may be converted to boronic acids of Formula (III-a) by first formation of the corresponding organolithium intermediates by reaction with an appropriate alkyllithium reagent, such as n-butyllithium, in a suitable solvent, such as tetrahydrofuran, at −100° C. followed by addition of an appropriate trialkylborate, such as triisopropylborate, and hydrolysis of the intermediate boronate esters by treatment with aqueous hydrochloric acid.

In another particular case, methoxy derivatives of Formula (XII) may be converted to heteroaryl stannanes of Formula (III-b) by first formation of the corresponding organolithium intermediates by reaction with lithium 2,2,6,6-tetramethylpiperidide in a suitable solvent, such as diethyl ether, at temperatures ranging from −78 to 0° C. followed by addition of an appropriate chlorotrialkylstannane, such as chlorotributylstannane.

In another embodiment of the present invention, compounds of general sub-Formula (I-b) may be prepared by the following synthetic route as illustrated in Scheme 4:

Scheme 4

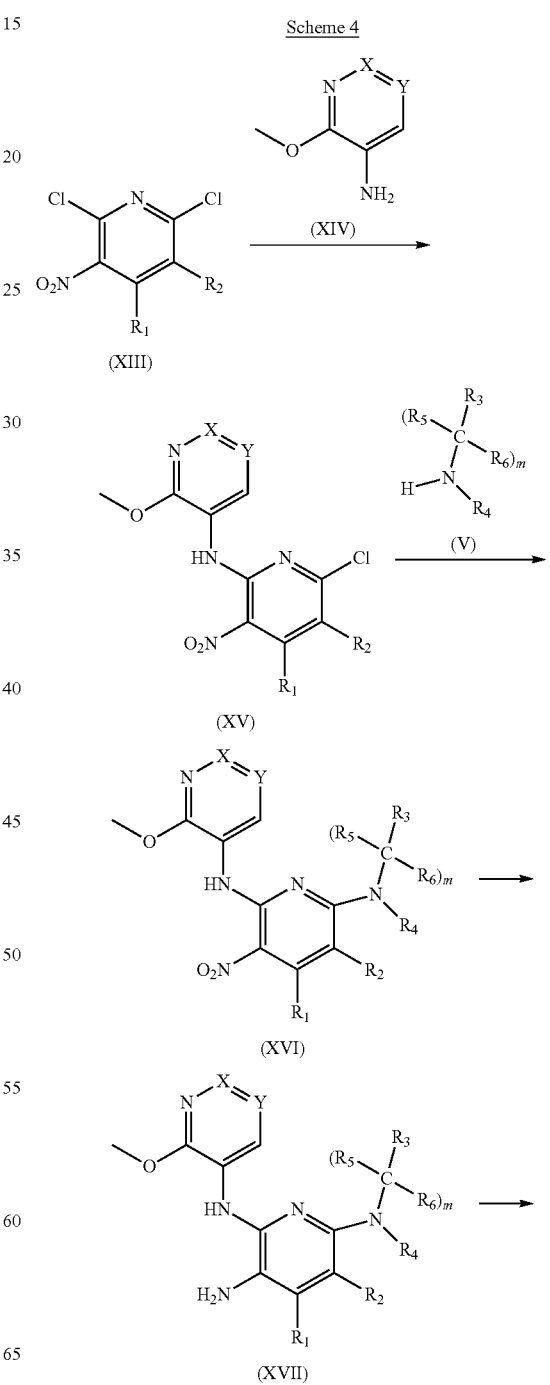

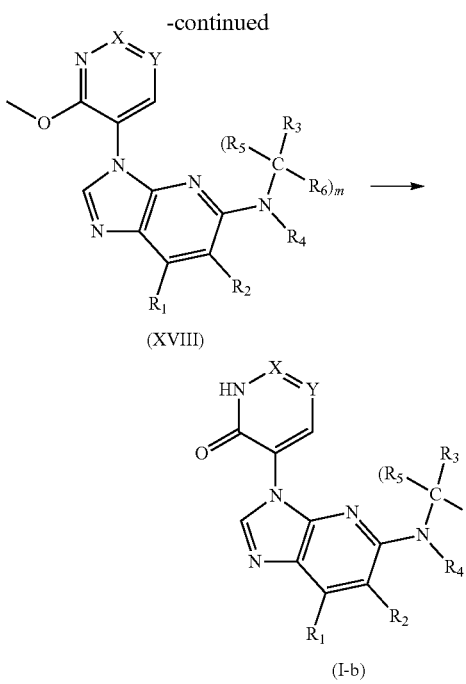

Pyridines of Formula (XIII) may be reacted with heteroaromatic amines of Formula (XIV) in the presence of a base, such as triethylamine, in a solvent such as acetonitrile at temperatures ranging from ambient temperature to 90° C. to furnish compounds of Formula (XV).

Treatment of compounds of Formula (XV) with amines of Formula (V) in the presence of a suitable base such as diisopropylethylamine in a solvent such as n-butanol at 80° C. with or without the use of microwave irradiation gives rise to compounds of Formula (XVI).

Compounds of Formula (XVI) may in turn be converted to amines of Formula (XVII) by reduction with hydrogen gas at atmospheric pressure using a suitable catalyst such as palladium on carbon or Raney®-Nickel in a solvent such as ethanol or ethyl acetate at ambient temperature.

Reaction of amines of Formula (XVII) with a suitable reagent such as formamidine acetate in a solvent such as ethanol at 85° C. furnishes imidazopyridines of Formula (XVIII).

Treatment of compounds of Formula (XVIII) with a suitable reagent, such as a mixture of trimethylsilyl chloride and sodium iodide in a solvent such as acetonitrile at temperatures ranging from ambient temperature to reflux or with aqueous hydrogen bromide solution at 100° C. gives rise to compounds of Formula (I-b).

When the defined R groups are susceptible to chemical reaction under the conditions of the hereinbefore described processes or are incompatible with said processes, conventional protecting groups may be used in accordance with standard practice, for example see T. W. Greene and P. G. M. Wuts in 'Protective Groups in Organic Synthesis', 3rd Edition, John Wiley & Sons (1999). It may be that deprotection will form the last step in the synthesis of compounds of sub-Formulae (I-a) or (I-b).

The term amino-protecting group refers to a protecting group suitable for preventing undesired reactions at amino nitrogen. Representative amino-protecting groups include, but are not limited to, formyl; acyl groups, for example alkanoyl groups such as acetyl; alkoxycarbonyl groups such as tert-butoxycarbonyl (Boc); arylmethoxycarbonyl groups such as benzyloxycarbonyl (Cbz) and 9-fluorenylmethoxycarbonyl (Fmoc); arylmethyl groups such as benzyl (Bn), trityl (Tr), and 1,1-di-(4'-methoxyphenyl)methyl; silyl groups such as trimethylsilyl (TMS) and tert-butyldimethylsilyl (TBS); and the like.

The term hydroxy-protecting group refers to a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

In a particular case, compounds of general sub-Formulae (I-a) or (I-b), in which the residue at $R_3$, $R_5$ or $R_6$ contains, in part, an amine moiety functionalized with an appropriate protecting group such as tert-butoxycarbonyl (BOC), may be deprotected at the amine moiety under standard conditions (*Greene's Protective Groups in Organic Synthesis*). The corresponding free amine may then be further functionalized by, for example, alkylation, amidation, sulfonamidation or arylation under standard reaction conditions.

EXAMPLES

The syntheses of the compounds of the invention and of the intermediates for use therein are illustrated by the following Examples (1-21) (including Preparation Examples (Preparations 1-25)) are given in order to provide a person skilled in the art with a sufficiently clear and complete explanation of the present invention, but should not be considered as limiting of the essential aspects of its subject, as set out in the preceding portions of this description.

Preparation 1

3-Bromo-6-chloroimidazo[1,2-b]pyridazine a) 6-Chloroimidazo[1,2-b]pyridazine

Hydrobromic acid (48% solution in water, 1.8 mL, 15.47 mmol) was added to a solution of 2-bromo-1,1-diethoxyethane (11.6 mL, 77.11 mmol) in water (18 mL) at ambient temperature and the resulting mixture was heated at 110° C. After 45 minutes, the reaction mixture was cooled and diethyl ether was added. The organic layer was separated, dried over magnesium sulphate and the solvent evaporated to obtain a colorless oil, which was added to a suspension at 0° C. of 6-chloropyridazin-3-amine (5.0 g, 38.60 mmol) in n-butanol (8 mL). The resulting mixture was heated at 130° C. overnight. The solvent was removed under reduced pressure, the residue was taken up in a mixture of ethyl acetate and water and the organic layer was separated. The aqueous layer was treated with solid sodium hydrogencarbonate until a basic pH was reached and extracted several times with ethyl acetate. The organic layers were combined, dried over magnesium sulphate and the solvent removed under reduced pressure. The resulting residue was treated with diisopropyl ether, filtered and dried in vacuo to yield the title compound (4.8 g, 85%) as a beige solid.

LRMS (m/z): 154 (M+1)$^+$.

$^1$H-NMR δ (300 MHz, CDCl$_3$): 7.08 (d, 1H), 7.81 (s, 1H), 7.88-7.99 (m, 2H).

b) 3-Bromo-6-chloroimidazo[1,2-b]pyridazine

Bromine (3.8 mL, 74.19 mmol) was added dropwise to a solution of 6-chloroimidazo[1,2-b]pyridazine (Preparation 1a, 4.8 g, 31.06 mmol) in glacial acetic acid (80 mL) and the resulting mixture was stirred at ambient temperature for 20 minutes. The precipitate formed was collected by filtration, washed with diethyl ether several times and dried in vacuo. The solid obtained was partitioned between ethyl acetate and a saturated aqueous solution of potassium carbonate. The organic layer was separated and washed with a saturated aqueous solution of potassium carbonate, dried over magnesium sulphate and the solvent removed under reduced pressure. The crude was then treated with pentane, filtered and the solid obtained was dried in vacuo to yield the title compound (6.6 g, 92%) as a pale yellow solid.

LRMS (m/z): 232 (M+1)$^+$.

$^1$H-NMR δ (300 MHz, CDCl$_3$): 7.13 (d, 1H), 7.80 (s, 1H), 7.92 (d, 1H).

Preparation 2

6-Chloro-3-(2-methoxypyridin-3-yl)imidazo[1,2-b]pyridazine

A mixture of 3-bromo-6-chloroimidazo[1,2-b]pyridazine (Preparation 1b, 6.0 g, 25.81 mmol), (2-methoxypyridin-3-yl)boronic acid (3.3 g, 21.58 mmol), cesium carbonate (30 mL of a 2M solution in water, 60 mmol) and 1,4-dioxane (250 mL) in a Schlenk vial was subjected to three cycles of evacuation backfilling with argon. [1,1'-Bis(diphenyl phosphino)ferrocene]-dichloropalladium(II) complex with dichloromethane (1:1) (1.8 g, 2.16 mmol) was then added and the resulting mixture was again subjected to three further cycles of evacuation backfilling before being heated at 100° C. for 2 hours. Subsequently, the reaction was cooled down, diluted with water and extracted with ethyl acetate. The organic layer was dried over magnesium sulphate and the solvent removed under reduced pressure. The residue was treated with ethyl acetate and the solid formed was filtered, washed with dichloromethane and dried in vacuo to yield the title compound (3.5 g, 62%) as a yellow solid.

LRMS (m/z): 261 (M+1)$^+$.

$^1$H-NMR δ (300 MHz, CDCl$_3$): 4.07 (s, 3H), 7.02-7.16 (m, 2H), 7.99 (d, 1H), 8.22 (dd, 1H), 8.33 (s, 1H), 8.59 (dd, 1H).

Preparation 3

3-((3R)-3-{[3-(2-Methoxypyridin-3-yl)imidazo[1,2-b]pyridazin-6-yl]amino}piperidin-1-yl)-3-oxopropanenitrile a) Tert-Butyl (3R)-3-{[3-(2-methoxypyridin-3-yl)imidazo[1,2-b]pyridazin-6-yl]-amino}piperidine-1-carboxylate A mixture of 6-chloro-3-(2-methoxypyridin-3-yl)imidazo[1,2-b]pyridazine (Preparation 2, 0.15 g, 0.58 mmol), tert-butyl (3R)-3-aminopiperidine-1-carboxylate (0.23 g, 1.15 mmol), 2'-(dicyclohexylphosphino)-N,N-dimethylbiphenyl-2-amine (0.03 g, 0.09 mmol), sodium tert-butoxide (0.08 g, 0.81 mmol) and toluene (4 mL) in a Schlenk vial was subjected to three cycles of evacuation backfilling with argon. Tris(dibenzylidene acetone)dipalladium(0) (0.04 g, 0.04 mmol) was then added and the resulting mixture was subjected to three further cycles of evacuation backfilling before being heated at 110° C. for 20 hours. Subsequently, the reaction was cooled down, filtered through Celite® eluting with ethyl acetate and dichloromethane, and the filtrate was evaporated to dryness. The crude was purified by flash chromatography (1:1 hexanes/ethyl acetate to 100% ethyl acetate) to give the title compound (0.105 g, 42%) as a solid.

LRMS (m/z): 425 (M+1)$^+$.

$^1$H-NMR δ (300 MHz, CDCl$_3$): 1.18-1.51 (m, 10H), 1.67-1.86 (m, 2H), 1.86-2.03 (m, 1H), 3.33-3.52 (m, 3H), 3.81-3.98 (m, 1H), 4.06 (s, 3H), 4.33-4.58 (m, 1H), 6.45 (d, 1H), 6.95-7.09 (m, 1H), 7.72 (d, 1H), 8.09 (s, 1H), 8.10-8.17 (m, 1H), 8.73 (d, 1H).

b) 3-(2-Methoxypyridin-3-yl)-N-[(3R)-piperidin-3-yl]imidazo[1,2-b]pyridazin-6-amine A mixture of tert-butyl (3R)-3-{[3-(2-methoxypyridin-3-yl)imidazo[1,2-b]pyridazin-6-yl]-amino}piperidine-1-carboxylate (Preparation 3a, 0.1 g, 0.24 mmol) and a solution of hydrogen chloride in methanol (1.25 N solution, 4 mL) was stirred at ambient temperature for 5 hours. The reaction mixture was then carefully diluted with aqueous saturated sodium hydrogencarbonate solution and extracted with dichloromethane (×3). The organic layer was dried eluting through a Phase Separator® membrane and the solvent removed under reduced pressure to yield the title compound (0.08 g, 98%) as a yellow solid.

LRMS (m/z): 325 (M+1)*.

$^1$H-NMR δ (300 MHz, CDCl$_3$): 1.25 (br.s., 1H), 1.78-2.00 (m, 3H), 2.72-3.07 (m, 4H), 3.10-3.28 (m, 1H), 4.05 (s, 3H), 5.14-5.43 (m, 1H), 6.55 (d, 1H), 7.00 (d, 1H), 7.70 (d, 1H), 8.05 (s, 1H), 8.13 (d, 1H), 8.68 (d, 1H).

c) 3-((3R)-3-{[3-(2-Methoxypyridin-3-yl)imidazo[1,2-b]pyridazin-6-yl]amino}-piperidin-1-yl)-3-oxopropanenitrile 3-[(2,5-Dioxopyrrolidin-1-yl)oxy]-3-oxopropanenitrile (prepared as described in BE875054(A1), 75 mg, 0.23 mmol) was added to a stirred solution of 3-(2-methoxy pyridin-3-yl)-N-[(3R)-piperidin-3-yl]imidazo[1,2-b]pyridazin-6-amine (Preparation 3b, 63 mg, 0.35 mmol) in dichloromethane (4 mL) and the mixture was stirred at ambient temperature for 18 hours. The solvent was then removed under reduced pressure and the residue was purified by flash chromatography (100% ethyl acetate to 3:2 ethyl acetate/ethanol) to give the title compound (58 mg, 64%) as a solid.

LRMS (m/z): 392 (M+1)$^+$.

Preparation 4

3-(2-Methoxypyridin-3-yl)-N-[(1S)-1-phenylethyl]imidazo[1,2-b]pyridazin-6-amine

Obtained as a brown oil (34%) from 6-chloro-3-(2-methoxypyridin-3-yl)imidazo[1,2-b]pyridazine (Preparation 2) and [(1S)-1-phenylethyl]amine following the experimental procedure as described in Preparation 3a followed by purification by flash chromatography (1:1 hexanes/ethyl acetate to 100% ethyl acetate to 7:3 ethyl acetate/ethanol).

LRMS (m/z): 346 (M+1)$^+$.

$^1$H-NMR δ (300 MHz, CDCl$_3$): 1.58 (d, 3H), 4.03 (s, 3H), 4.76 (d, 1H), 4.84-5.00 (m, 1H), 6.52 (d, 1H), 6.85 (dd, 1H), 7.32-7.42 (m, 5H), 7.70 (d, 1H), 8.05 (s, 1H), 8.09 (dd, 1H), 8.14 (d, 1H), 8.16 (d, 1H).

Preparation 5

N-[(1S)-1-(5-Fluoropyridin-2-yl)ethyl]-3-(2-methoxypyridin-3-yl)imidazo[1,2-b]pyridazin-6-amine Obtained as pale yellow solid (31%) from 6-chloro-3-(2-methoxypyridin-3-yl)imidazo[1,2-b]pyridazine (Preparation 2) and (S)-1-(5-fluoropyridin-2-yl)ethanamine (prepared according to the method described in WO2006/82392A1) following the experimental procedure as described in Preparation 3a followed by purification by flash chromatography (1:1 hexanes/ethyl acetate to 100% ethyl acetate to 7:3 ethyl acetate/ethanol).

LRMS (m/z): 365 (M+1)⁺.

¹H-NMR δ (300 MHz, CDCl₃): 1.59 (d, 3H), 4.04 (s, 3H), 4.98-5.11 (m, 1H), 5.40 (d, 1H), 6.56 (d, 1H), 6.97 (dd, 1H), 7.27-7.39 (m, 2H), 7.71 (d, 1H), 8.04 (s, 1H), 8.14 (dd, 1H), 8.39-8.46 (m, 2H).

Preparation 6

N-[(1R)-1-(5-Fluoropyridin-2-yl)ethyl]-3-(2-methoxypyridin-3-yl)imidazo[1,2-b]pyridazin-6-amine Obtained as a solid (12%) from 6-chloro-3-(2-methoxypyridin-3-yl)imidazo[1,2-b]pyridazine (Preparation 2) and (R)-1-(5-fluoropyridin-2-yl)ethanamine (prepared according to the method described in WO2009/058298A1) following the experimental procedure as described in Preparation 3a followed by purification by flash chromatography (1:1 hexanes/ethyl acetate to 100% ethyl acetate to 3:2 ethyl acetate/ethanol).

LRMS (m/z): 365 (M+1)⁺.

¹H-NMR δ (300 MHz, CDCl₃): 1.59 (d, 3H), 4.04 (s, 3H), 4.98-5.11 (m, 1H), 5.40 (d, 1H), 6.56 (d, 1H), 6.97 (dd, 1H), 7.27-7.39 (m, 2H), 7.71 (d, 1H), 8.04 (s, 1H), 8.14 (dd, 1H), 8.39-8.46 (m, 2H).

Preparation 7

N-[(1S)-1-(5-Fluoropyrimidin-2-yl)ethyl]-3-(2-methoxypyridin-3-yl)imidazo[1,2-b]pyridazin-6-amine Obtained as a solid (14%) from 6-chloro-3-(2-methoxypyridin-3-yl)imidazo[1,2-b]pyridazine (Preparation 2) and (1S)-1-(5-fluoropyrimidin-2-yl)ethanamine (prepared according to the method described in WO2006/82392A1) following the experimental procedure as described in Preparation 3a followed by purification by flash chromatography (1:1 hexanes/ethyl acetate to 100% ethyl acetate to 3:2 ethyl acetate/ethanol).

LRMS (m/z): 366 (M+1)⁺.

¹H-NMR δ (300 MHz, CDCl₃): 1.64 (d, 3H), 4.05 (s, 3H), 5.17-5.33 (m, 1H), 5.47 (d, 1H), 6.60 (d, 1H), 6.99-7.08 (m, 1H), 7.73 (d, 1H), 8.09 (s, 1H), 8.11-8.19 (m, 1H), 8.55 (s, 2H), 8.61 (d, 1H).

Preparation 8

3-Methoxy-4-(tributylstannyl)pyridazine a) 3-Methoxypyridazine

Palladium on carbon (10%, 0.1 g) and ammonium formate (2.1 g, 33.3 mmol) were added to a stirred solution of 3-chloro-6-methoxypyridazine (2.5 g, 26.43 mmol) in methanol (10 mL) and the resulting mixture was stirred at 50° C. for 1 hour. The reaction was cooled down, filtered through Celite® under nitrogen atmosphere eluting with methanol and the filtrate was evaporated to dryness. The crude product was diluted with dichloromethane and washed with water. The organic layer was dried over magnesium sulphate and the solvent removed under reduced pressure to yield the title compound (1.55 g, 86%) as a pale yellow oil.

¹H-NMR δ (300 MHz, CDCl₃): 4.16 (s, 3H), 7.00 (dd, 1H), 7.38 (dd, 1H), 8.82-8.87 (m, 1H).

b) 3-Methoxy-4-(tributylstannyl)pyridazine n-Butyllithium (2.5 M solution in hexanes, 7.1 mL, 17.75 mmol) was slowly added (0.2 mL/min) to a solution of 2,2,6,6-tetramethylpiperidine (3 mL, 17.75 mmol) in dry diethyl ether (16 mL) at −30° C. under argon atmosphere. The reaction mixture was stirred at 0° C. for 30 minutes before being cooled down to −78° C. and a solution of 3-methoxypyridazine (Preparation 8a, 0.85 g, 7.72 mmol) in dry diethyl ether (4 mL) was slowly added (0.03 mL/min). The reaction mixture was stirred at this temperature for 10 additional minutes before the addition of tributylchlorostannane (2.5 mL, 9.22 mmol). After stirring at −78° C. for 45 minutes, a mixture of diethyl ether and aqueous saturated solution of ammonium chloride (15 mL/5 mL) was added and the temperature was allowed to warm up to ambient temperature. Additional diethyl ether (300 mL) was then added to the mixture and the organic layer was separated, washed with saturated aqueous solution of ammonium chloride, dried over magnesium sulphate and the solvent removed under reduced pressure. The residue was purified by flash chromatography (100% hexanes to 1:1 hexanes/diethyl ether) to give the title compound (0.31 g, 10%) as a pale yellow oil.

¹H-NMR δ (300 MHz, CDCl₃): 0.88 (t, 9H), 1.03-1.19 (m, 6H), 1.23-1.40 (m, 6H), 1.43-1.61 (m, 6H), 4.09 (s, 3H), 7.44 (d, 1H), 8.69 (d, 1H).

Preparation 9

3-(3-Methoxypyridazin-4-yl)-N-[(1S)-1-phenylethyl]imidazo[1,2-b]pyridazin-6-amine a) 6-Chloro-3-(3-methoxypyridazin-4-yl)imidazo[1,2-b]pyridazine A mixture of 3-bromo-6-chloroimidazo[1,2-b]pyridazine (Preparation 1b, 182 mg, 0.78 mmol), 3-methoxy-4-(tributylstannyl)pyridazine (Preparation 8b, 313 mg, 0.78 mmol), copper(I) iodide (15 mg, 0.08 mmol) and dry N,N'-dimethylformamide (4 mL) in a Schlenk vial was subjected to three cycles of evacuation backfilling with argon. Tetrakis(triphenylphosphine)palladium(0) (91 mg, 0.08 mmol) was then added and the resulting mixture was subjected to three further cycles of evacuation backfilling with argon before being stirred at 100° C. for 20 hours. The reaction mixture was cooled down, the solvent was removed under reduced pressure and the residue was purified by flash chromatography (1:1 hexanes/ethyl acetate to 100% ethyl acetate) to give the title compound (131 mg, 64%) as a beige solid.

LRMS (m/z): 262 (M+1)⁺.

b) 3-(3-Methoxypyridazin-4-yl)-N-[(1S)-1-phenylethyl]imidazo[1,2-b]pyridazin-6-amine Obtained as a solid (21%) from 6-chloro-3-(3-methoxypyridazin-4-yl)imidazo[1,2-b]pyridazine (Preparation 9a) and [(1S)-1-phenylethyl]amine following the experimental procedure as described in Preparation 3a followed by purification by flash chromatography (100% dichloromethane to 97:3 dichloromethane/methanol).

LRMS (m/z): 347 (M+1)⁺.

Preparation 10

(5-Fluoro-2-methoxypyridin-3-yl)boronic acid n-Butyllithium (1.6 M solution in hexanes, 20 mL, 32 mmol) was slowly added (0.4 mL/min) to a solution of 3-bromo-5-fluoro-2-methoxypyridine (6.0 g, 29.12 mmol) and triisopropylborate (8.4 mL, 36.62 mmol) in dry tetrahydrofuran (70 mL) at −100° C. under argon atmosphere. The reaction mixture was stirred at −100° C. for 2 hours and afterwards the temperature was allowed to warm up slowly overnight to ambient temperature before being cooled down to 0° C. Aqueous hydrochloric acid (1N solution, 120 mL) was slowly added and the mixture was stirred at 0° C. for 1 hour. A solution of sodium hydroxide (32% in water) was then added until pH was around 6 and the resulting mixture was extracted with diethyl ether (×3). The combined organic layers were dried over magnesium sulphate and the solvent removed under reduced pressure to yield the title compound (3.28 g, 66%) as a white solid.

LRMS (m/z): 172 (M+1)$^+$.
$^1$H-NMR δ (300 MHz, CDCl$_3$): 4.04 (s, 3H), 6.00 (s, 2H), 7.88 (dd, 1H), 8.09 (d, 1H).

Preparation 11

6-Chloro-3-(5-fluoro-2-methoxypyridin-3-yl)imidazo[1,2-b]pyridazine

Obtained as a yellow solid (55%) from (5-fluoro-2-methoxypyridin-3-yl)boronic acid (Preparation 10) and 3-bromo-6-chloroimidazo[1,2-b]pyridazine (Preparation 1b) following the experimental procedure as described in Preparation 2.

LRMS (m/z): 279 (M+1)$^+$.
$^1$H-NMR δ (300 MHz, CDCl$_3$): 4.07 (s, 3H), 7.15 (d, 1H), 7.95-8.06 (m, 2H), 8.47 (s, 1H), 8.64 (d, 1H).

Preparation 12

3-(5-Fluoro-2-methoxypyridin-3-yl)-N-[(1S)-1-(5-fluoropyridin-2-yl)ethyl]imidazo-[1,2-b]pyridazin-6-amine Obtained as a pale orange solid (20%) from 6-chloro-3-(5-fluoro-2-methoxypyridin-3-yl)imidazo[1,2-b]pyridazine (Preparation 11) and (S)-1-(5-fluoropyridin-2-yl)ethanamine (prepared according to the method described in WO2006/82392A1) following the experimental procedure as described in Preparation 3a followed by purification by flash chromatography (1:1 hexanes/ethyl acetate to 100% ethyl acetate to 7:3 ethyl acetate/ethanol).

LRMS (m/z): 383 (M+1)$^+$.
$^1$H-NMR δ (300 MHz, CDCl$_3$): 1.60 (br. s., 3H), 4.05 (s, 3H), 4.99-5.26 (m, 1H), 5.38-5.65 (m, 1H), 6.47-6.77 (m, 1H), 7.30-7.54 (m, 3H), 7.64-7.83 (m, 1H), 7.87-8.09 (m, 1H), 8.31-8.51 (m, 1H), 8.51-8.72 (m, 1H).

Preparation 13

(5-Chloro-2-methoxypyridin-3-yl)boronic acid a) 3-Bromo-5-chloro-2-methoxypyridine

A solution of bromine (1.5 mL, 29.28 mmol) in glacial acetic acid (7 mL) was slowly added to a mixture of 5-chloro-2-methoxypyridine (2.1 g, 14.63 mmol) and sodium acetate (1.2 g, 14.63 mmol) in glacial acetic acid (7 mL) and the resulting mixture was stirred at 80° C. for 6 hours. The reaction was allowed to cool down to ambient temperature and then diethyl ether and water were added. The organic layer was separated, washed with a 1N aqueous solution of sodium hydroxide and a 4% aqueous solution of sodium bisulphite, dried over magnesium sulphate and the solvent removed under reduced pressure. The residue was purified by flash chromatography (100% hexanes) to give the title compound (2.1 g, 64%) as a white solid.

$^1$H-NMR δ (300 MHz, CDCl$_3$): 3.99 (s, 3H), 7.81 (d, 1H), 8.05 (d, 1H).

b) (5-Chloro-2-methoxypyridin-3-yl)boronic acid

Obtained as white solid (72%) from 3-bromo-5-chloro-2-methoxypyridine (Preparation 13a) and triisopropylborate following the experimental procedure as described in Preparation 10.

LRMS (m/z): 188 (M+1)$^+$.
$^1$H-NMR δ (300 MHz, CDCl$_3$): 4.03 (s, 3H), 5.94 (s, 2H), 8.08 (d, 1H), 8.19 (d, 1H).

Preparation 14

6-Chloro-3-(5-chloro-2-methoxypyridin-3-yl)imidazo[1,2-b]pyridazine

Obtained as a yellow solid (40%) from (5-chloro-2-methoxypyridin-3-yl)boronic acid (Preparation 13b) and 3-bromo-6-chloroimidazo[1,2-b]pyridazine (Preparation 1b) following the experimental procedure as described in Preparation 2.

LRMS (m/z): 295 (M+1)$^+$.
$^1$H-NMR δ (300 MHz, DMSO-d$_6$): 3.99 (s, 3H), 7.51 (d, 1H), 8.31 (d, 1H), 8.33 (d, 1H), 8.37 (s, 1H), 8.63 (d, 1H).

Preparation 15

3-(5-Chloro-2-methoxypyridin-3-yl)-N-[(1S)-1-(5-fluoropyridin-2-yl)ethyl]imidazo-[1,2-b]pyridazin-6-amine Obtained as a brown solid (30%) from 6-chloro-3-(5-chloro-2-methoxypyridin-3-yl) imidazo[1,2-b]pyridazine (Preparation 14) and (S)-1-(5-fluoropyridin-2-yl)ethanamine (prepared according to the method described in WO2006/82392A1) following the experimental procedure as described in Preparation 3a followed by purification by flash chromatography (97:3 dichloromethane/methanol).

LRMS (m/z): 399 (M4-1)$^+$.
$^1$H-NMR δ (300 MHz, CDCl$_3$): 1.63 (d, 3H), 4.06 (s, 3H), 5.03-5.29 (m, 1H), 5.75 (d, 1H), 6.60 (d, 1H), 7.32-7.49 (m, 2H), 7.71 (d, 1H), 8.07 (br. s., 1H), 8.16 (s, 1H), 8.41 (br. s., 1H), 8.93 (br. s., 1H).

Preparation 16

3-Bromo-6-chloro-7-methylimidazo[1,2-b]pyridazine a) 6-Chloro-5-methylpyridazin-3-amine (+6-chloro-4-methylpyridazin-3-amine)

Ammonia (32% solution in water, 54 mL) was added to a solution of 3,6-dichloro-4-methylpyridazine (5.0 g, 30.67 mmol) in ethanol (25 mL) in a sealed tube. The resulting mixture was stirred at 100° C. for 70 hours, cooled down and the solvent was removed under reduced pressure. The residue was purified by flash chromatography (3:2 hexanes/ethyl acetate to 100% ethyl acetate) to yield the title compound (3.8 g, 57%) as a mixture of two isomers which was used in the next step without further purification.
LRMS (m/z): 144 (M+1)$^+$.

b) 6-Chloro-7-methylimidazo[1,2-b]pyridazine

Obtained as a beige solid (41%) from the mixture of 6-chloro-4-methylpyridazin-3-amine and 6-chloro-5-methylpyridazin-3-amine (Preparation 16a) following the experimental procedure as described in Preparation 1a followed by purification by flash chromatography (100% hexanes to 7:3 hexanes/ethyl acetate).
LRMS (m/z): 168 (M+1)$^+$.
$^1$H-NMR δ (300 MHz, CDCl$_3$): 2.46 (s, 3H), 7.72 (s, 1H), 7.78 (s, 1H), 7.87 (s, 1H).

c)
3-Bromo-6-chloro-7-methylimidazo[1,2-b]pyridazine

Obtained as a beige solid (100%) from 6-chloro-7-methylimidazo[1,2-b]pyridazine (Preparation 16b) following the experimental procedure as described in Preparation 1b.
LRMS (m/z): 246 (M+1)$^+$.
$^1$H-NMR δ (300 MHz, CD$_3$OD): 2.55 (s, 3H), 7.91 (s, 1H), 8.06 (br. s., 1H).

Preparation 17

6-Chloro-3-(2-methoxypyridin-3-yl)-7-methylimidazo[1,2-b]pyridazine

Obtained as a green solid (76%) from (2-methoxypyridin-3-yl)boronic acid and 3-bromo-6-chloro-7-methylimidazo[1,2-b]pyridazine (Preparation 16c) following the experimental procedure as described in Preparation 2.
LRMS (m/z): 275 (M+1)$^+$.
$^1$H-NMR δ (300 MHz CDCl$_3$): 2.50 (s, 3H), 4.08 (s, 3H), 7.09 (dd, 1H), 7.85 (s, 1H), 8.20 (d, 1H), 8.27 (s, 1H), 8.62 (d, 1H).

Preparation 18

N-[(1S)-1-(5-Fluoropyridin-2-yl)ethyl]-3-(2-methoxypyridin-3-yl)-7-methylimidazo-[1,2-b]pyridazin-6-amine Obtained as a beige solid (25%) from 6-chloro-3-(2-methoxypyridin-3-yl)-7-methyl imidazo[1,2-b]pyridazine (Preparation 17) and (S)-1-(5-fluoropyridin-2-yl)ethanamine (prepared according to the method described in WO2006/82392A1) following the experimental procedure as described in Preparation 3a followed by purification by flash chromatography (1:1 hexanes/ethyl acetate to 100% ethyl acetate to 7:3 ethyl acetate/ethanol).
LRMS (m/z): 379 (M+1)$^+$.
$^1$H-NMR δ (300 MHz, CDCl$_3$): 1.62 (d, 3H), 2.35 (s, 3H), 4.05 (s, 3H), 5.05-5.17 (m, 1H), 5.48 (d, 1H), 6.98 (dd, 1H), 7.24-7.39 (m, 2H), 7.55 (s, 1H), 8.01 (s, 1H), 8.13 (d, 1H), 8.43 (d, 1H), 8.49 (dd, 1H).

Preparation 19

6-Chloro-3-(5-fluoro-2-methoxypyridin-3-yl)-7-methylimidazo[1,2-b]pyridazine

Obtained as a beige solid (56%) from (5-fluoro-2-methoxypyridin-3-yl)boronic acid (Preparation 10) and 3-bromo-6-chloro-7-methylimidazo[1,2-b]pyridazine (Preparation 16c) following the experimental procedure as described in Preparation 2.
LRMS (m/z): 293 (M+1)$^+$.
$^1$H-NMR δ (300 MHz, CDCl$_3$): 2.51 (s, 3H), 4.07 (s, 3H), 7.87 (s, 1H), 8.00 (d, 1H), 8.41 (s, 1H), 8.66 (dd, 1H).

Preparation 20

3-(5-Fluoro-2-methoxypyridin-3-yl)-N-[(1S)-1-(5-fluoropyridin-2-yl)ethyl]-7-methyl-imidazo[1,2-b]pyridazin-6-amine Obtained as a beige solid (27%) from 6-chloro-3-(5-fluoro-2-methoxypyridin-3-yl)-7-methylimidazo[1,2-b]pyridazine (Preparation 19) and (S)-1-(5-fluoropyridin-2-yl)ethanamine (prepared according to the method described in WO2006/82392A1) following the experimental procedure as described in Preparation 3a followed by purification by flash chromatography (1:1 hexanes/ethyl acetate to 100% ethyl acetate to 7:3 ethyl acetate/ethanol).
LRMS (m/z): 397 (M+1)$^+$.
$^1$H-NMR δ (300 MHz, CDCl$_3$): 1.65 (d, 3H), 2.37 (s, 3H), 4.06 (s, 3H), 5.10-5.25 (m, 1H), 5.62 (d, 1H), 7.38 (d, 1H), 7.41 (d, 1H), 7.58 (s, 1H), 7.93 (d, 1H), 8.18 (s, 1H), 8.42 (s, 1H), 8.69 (dd, 1H).

Preparation 21

3-(5-Fluoro-2-methoxypyridin-3-yl)-N-[(1S)-1-(5-fluoropyrimidin-2-yl)ethyl]imidazo[1,2-b]pyridazin-6-amine a) 3-Bromo-N-[(1S)-1-(5-fluoropyrimidin-2-yl)ethyl]imidazo[1,2-b]pyridazin-6-amine A mixture of 3-bromo-6-chloroimidazo[1,2-b]pyridazine (Preparation 1b, 0.2 g, 0.86 mmol), (1S)-1-(5-fluoropyrimidin-2-yl)ethanamine (prepared according to the method described in WO2006/82392A1, 0.24 g, 1.72 mmol), cesium fluoride (1.31 g, 8.60 mmol) and dimethylsulfoxide (5 mL) was heated at 180° C. for 2 hours in a sealed tube. The reaction was cooled down, filtered through Celite® eluting with ethyl acetate and the filtrate was washed with water, dried over magnesium sulphate and the solvent removed under reduced pressure. The residue was purified by flash chromatography (40-70% acetone in hexanes) to give the title compound (0.11 g, 64%) as a brown foam.
$^1$H-NMR δ (250 MHz, CDCl$_3$): 1.67 (d, 3H), 5.29-5.41 (m, 1H), 5.68 (d, 1H), 6.57 (d, 1H), 7.46 (s, 1H), 7.60 (d, 1H), 8.58 (s, 2H).

b) 3-(5-Fluoro-2-methoxypyridin-3-yl)-N-[(1S)-1-(5-fluoropyrimidin-2-yl)ethyl]imidazo[1,2-b]pyridazin-6-amine Obtained as a yellow solid (54%) from 3-bromo-N-[(1S)-1-(5-fluoropyrimidin-2-yl)ethyl]imidazo[1,2-b]pyridazin-6-amine (Preparation 21b) and (5-fluoro-2-methoxypyridin-3-yl)boronic acid (Preparation 10) following the experimental procedure as described in Preparation 2 followed by purification by flash chromatography (40-60% acetone/hexanes).
$^1$H-NMR δ (250 MHz, CDCl$_3$): 1.66 (d, 3H), 4.02 (s, 3H), 5.18-5.32 (m, 1H), 5.50 (d, 1H), 6.62 (d, 1H), 7.73 (d, 1H), 7.93 (d, 1H), 8.20 (s, 1H), 8.54 (d, 1H), 8.57 (s, 2H).

Preparation 22

N-[(1S)-1-(5-Fluoropyridin-2-yl)ethyl]-3-(2-methoxypyridin-3-yl)-3H-imidazo[4,5-b]pyridin-5-amine a) 6-Chloro-N-(2-methoxypyridin-3-yl)-3-nitropyridin-2-amine

Triethylamine (6.5 mL, 46.6 mmol) was added to a solution of 2-methoxypyridin-3-amine (1.0 g, 8.1 mmol) and 2,6-dichloro-3-nitropyridine (1.62 g, 8.4 mmol) in acetonitrile (30 mL) and the resulting mixture was stirred at ambient temperature for 5 days and then at 50° C. for 24 h. The precipitate formed was filtered, washed with acetonitrile and dried in vacuo. The solid was then treated with tetrahydrofuran, filtered, washed with more tetrahydrofuran and the combined filtrate and washings were concentrated to dryness under reduced pressure to yield the title compound (0.32 g, 11%) as an orange solid.

LRMS (m/z): 281, 283 $(M+1)^+$.
$^1$H-NMR δ (300 MHz, $CDCl_3$): 4.11 (s, 3H), 6.86 (d, 1H), 6.99 (dd, 4.94 Hz, 1H), 7.93 (d, 1H), 8.51 (d, 1H), 8.80 (d, 1H); 10.79 (br. s, 1H).

b) $N^6$-[(1S)-1-(5-Fluoropyridin-2-yl)ethyl]-$N^2$-(2-methoxypyridin-3-yl)-3-nitro pyridine-2,6-diamine Diisopropylethylamine (0.49 mL, 2.81 mmol) was added to a solution of 6-chloro-N-(2-methoxypyridin-3-yl)-3-nitropyridin-2-amine (Preparation 22a, 0.26 g, 0.69 mmol) and (S)-1-(5-fluoropyridin-2-yl)ethanamine hydrochloride (prepared according to the method described in WO2006/82392A1, 0.13 g, 0.74 mmol) in butanol (5 mL) and the resulting mixture was stirred at 80° C. overnight. Subsequently, the reaction was cooled down, diluted with ethyl acetate and washed with brine (×3). The organic phase was separated, dried over anhydrous magnesium sulphate and the solvent removed under reduced pressure. The residue was purified by flash chromatography (hexanes 100% to 1:1 hexanes/ethyl acetate) to give the title compound (253 mg, 94%) as a yellow solid.

LRMS (m/z): 385 $(M+1)^+$.
$^1$H-NMR δ (300 MHz, $CDCl_3$): 1.60 (s, 3H), 4.08 (s, 3H), 5.26 (br. s., 1H), 6.03 (d, 1H), 6.38 (d, 1H), 6.91 (dd, 1H), 7.39 (t, 1H), 7.89 (d, 1H), 8.28 (d, 1H), 8.45 (d, 1H), 8.62 (br. s., 1H), 11.22 (br. s., 1H).

c) $N^6$-[(1S)-1-(5-Fluoropyridin-2-yl)ethyl]-$N^2$-(2-methoxypyridin-3-yl)pyridine-2,3,6-triamine $N^6$-[(1S)-1-(5-Fluoropyridin-2-yl)ethyl]-$N^2$-(2-methoxypyridin-3-yl)-3-nitropyridine-2,6-diamine (Preparation 22b, 131 mg, 0.34 mmol) was added to a suspension of palladium on carbon (10%, 18 mg) in ethanol (5 mL) and the reaction mixture was stirred at ambient temperature under a hydrogen atmosphere. After 7 hours, additional palladium on carbon was added (18 mg) and the reaction mixture was stirred at ambient temperature under a hydrogen atmosphere for further 15 hours. The mixture was then filtered through Celite® and the filter cake was washed with ethanol (5×10 mL). The combined filtrate and washings containing the title compound as a methanolic solution was used in the next synthetic step without further purification.

d) N-[(1S)-1-(5-Fluoropyridin-2-yl)ethyl]-3-(2-methoxypyridin-3-yl)-3H-imidazo[4,5-b]pyridin-5-amine Formamidine acetate (141 mg, 1.35 mmol) was added to a solution of $N^6$-[(1S)-1-(5-fluoropyridin-2-yl)ethyl]$N^2$-(2-methoxypyridin-3-yl)pyridine-2,3,6-triamine in ethanol (Preparation 22c) and the resulting mixture was heated at 85° C. for 5 hours. The reaction was cooled down and diluted with ethyl acetate (50 mL), washed with brine (2×100 mL) and water (50 mL), dried over magnesium sulphate and the solvent removed under reduced pressure. The residue was purified by flash chromatography (9:1 hexanes/ethyl acetate to 100% ethyl acetate) to give the title compound (104 mg, 84%, two steps) as a green oil.

Preparation 23

5-Chloro-2-methoxypyridin-3-amine a) 5-Chloro-2-methoxy-3-nitropyridine

A solution of sodium methoxide (0.84 g, 16.6 mmol) in methanol (4 mL) was added dropwise to a solution of 2,5-dichloro-3-nitropyridine (1.00 g, 5.2 mmol) in methanol (10 mL) and the mixture was stirred and heated to reflux. After 7 hours, the mixture was cooled and diluted with water and the precipitate was filtered and washed with water to give the title compound (0.95 g, 97%) as a white solid.

$^1$H NMR δ (300 MHz, $CDCl_3$): 4.11 (s, 3H), 8.23 (s, 1H), 8.32 (s, 1H).

b) 5-Chloro-2-methoxypyridin-3-amine

Zinc bromide (226 mg, 1 mmol) and platinum on carbon (5%, 491 mg, 2.52 mmol) were added to a solution of 5-chloro-2-methoxy-3-nitropyridine (Preparation 23a, 950 mg, 5.04 mmol) in ethyl acetate (15 mL) and the reaction mixture was stirred at ambient temperature for 5 hours under a hydrogen atmosphere. The mixture was then filtered through Celite® and the filter cake was washed with methanol. The combined filtrate and washings were concentrated to give the title compound (820 mg, 100%) as a white solid.

LRMS (m/z): 159 $(M+1)^+$.
$^1$H NMR δ (300 MHz, $CDCl_3$): 3.97 (s, 3H), 6.98 (s, 1H), 7.50 (s, 1H).

Preparation 24

3-(5-Chloro-2-methoxypyridin-3-yl)-N-[(1S)-1-(5-fluoropyridin-2-yl)ethyl]-3H-imidazo[4,5-b]pyridin-5-amine a) 6-Chloro-N-(5-chloro-2-methoxypyridin-3-yl)-3-nitropyridin-2-amine

Triethylamine (2.7 mL) and a catalytic amount of 4-diaminopyrimidine were added to a solution of 2,6-dichloro-3-nitropyridine (639 mg, 3.31 mmol) and 5-chloro-2-methoxy pyridin-3-amine (Preparation 23, 501 mg, 3.16 mmol) in acetonitrile (20 mL) and the resulting mixture was stirred overnight at 90° C. Solvent was then removed under reduced pressure until a solid precipitated. The solid was filtered, washed with acetonitrile and dried. The solid was then treated with dichloromethane, filtered, washed with more dichloromethane and the combined filtrate and washings were concentrated to dryness under reduced pressure to yield the title compound (390 mg 30%) as an orange solid.

$^1$H-NMR δ (300 MHz, CDCl$_3$): 4.08 (s, 3H), 6.89 (d, 1H), 7.82 (d, 1H), 8.50 (d, 1H), 8.86 (d, 1H), 10.74 (bs, 1H).

b) N$^2$-(5-Chloro-2-methoxypyridin-3-yl)-N$^6$-[(1S)-1-(5-fluoropyridin-2-yl)ethyl]-3-nitropyridine-2,6-diamine Obtained as a yellow solid (61%) from 6-chloro-N-(5-chloro-2-methoxypyridin-3-yl)-3-nitropyridin-2-amine (Preparation 24a) and (S)-1-(5-fluoropyridin-2-yl)ethanamine (prepared according to the method described in WO2006/82392A1) following the experimental procedure as described in Preparation 22b. Reaction was heated at 80° C. for 3 hours under microwave irradiation. After work-up, the resulting crude was purified by flash chromatography (1:9 ethyl acetate/hexanes to 100% ethyl acetate).
LRMS (m/z): 419 (M+1)$^+$.
$^1$H-NMR δ (300 MHz, CDCl$_3$): 1.64 (d, 3H), 4.08 (s, 3H), 5.37 (bs, 1H), 6.08 (d, 1H), 7.33-7.47 (m, 2H), 7.83 (d, 1H), 8.28 (d, 1H), 8.44 (d, 1H), 9.02 (d, 1H), 11.30 (bs, 1H).

c) N$^2$-(5-Chloro-2-methoxypyridin-3-yl)-N$^6$-[(1S)-1-(5-fluoropyridin-2-yl)ethyl]pyridine-2,3,6-triamine A solution of N$^2$-(5-chloro-2-methoxypyridin-3-yl)-N$^6$-[(1S)-1-(5-fluoropyridin-2-yl)ethyl]-3-nitropyridine-2,6-diamine (Preparation 24b, 160 mg, 0.38 mmol) in ethyl acetate (11 mL) was hydrogenated using a H-Cube® Continuous-flow hydrogenation reactor and a Raney®-Nickel catalyst cartridge under a 80 bar pressure (flow=0.3 ml/min). Solvent was then concentrated to dryness under reduced pressure to yield the title compound (100 mg, 64%) as a green oil which was used in the next synthetic step without further purification.
LRMS (m/z): 389 (M+1)$^+$.
$^1$H-NMR δ (300 MHz, CDCl$_3$): 1.57 (d, 3H), 4.02 (s, 3H), 4.98 (bs, 1H), 5.80 (d, 1H), 6.94 (d, 1H), 7.26-7.43 (m, 2H), 7.55 (bs, 1H), 7.61 (d, 1H), 8.41 (d, 1H), 8.81 (d, 1H).

d) 3-(5-Chloro-2-methoxypyridin-3-yl)-N-[(1S)-1-(5-fluoropyridin-2-yl)ethyl]-3H-imidazo[4,5-b]pyridin-5-amine Obtained as an oil (76%) from N$^2$-(5-chloro-2-methoxypyridin-3-yl)-N$^6$-[(1S)-1-(5-fluoro pyridin-2-yl)ethyl]pyridine-2,3,6-triamine (Preparation 24c) and formamidine acetate following the experimental procedure as described in Preparation 22d followed by purification by flash chromatography (9:1 hexanes/ethyl acetate to 100% ethyl acetate).
LRMS (m/z): 399 (M+1)$^+$.
$^1$H-NMR δ (300 MHz, CDCl$_3$): 1.54 (d, 3H), 3.98 (s, 3H), 4.98-5.14 (m, 1H), 5.48 (d, 1H), 6.43 (d, 1H), 7.29-7.39 (m, 2H), 7.78 (d, 1H), 8.11-8.13 (m, 2H), 8.14 (s, 1H), 8.39 (s, 1H).

Preparation 25

3-(5-Chloro-2-methoxypyridin-3-yl)-N-[(1S)-1-(5-fluoropyridin-2-yl)ethyl]-6-methyl-3H-imidazo[4,5-b]pyridin-5-amine a) 6-Chloro-N-(5-chloro-2-methoxypyridin-3-yl)-5-methyl-3-nitropyridin-2-amine Sodium hydride (60% dispersion in mineral oil, 0.23 g, 5.80 mmol) was added to a stirred solution of 5-chloro-2-methoxypyridin-3-amine (Preparation 23b, 1.15 g, 7.25 mmol) in tetrahydrofuran (11 mL) and the resulting mixture was stirred at ambient temperature for 30 minutes. A solution of 2,6-dichloro-3-methyl-5-nitropyridine (prepared according to the method described in WO2010/094645(A1), 1.0 g, 4.83 mmol) in tetrahydrofuran (10 mL) was then added and the reaction mixture was heated at reflux overnight and then stirred at ambient temperature for 3 days. Solvent was evaporated under reduced pressure and the resulting residue was treated with methanol, filtered, washed with additional methanol and dried to yield the title compound (1.18 g, 74%) as an orange solid.
$^1$H-NMR δ (250 MHz, CDCl$_3$): 2.38 (s, 3H), 4.09 (s, 3H), 7.81 (d, 1H), 8.41 (s, 1H), 8.87 (d, 1H), 10.61 (br.s., 1H).

b) N$^6$-(5-Chloro-2-methoxypyridin-3-yl)-N$^2$-[(1S)-1-(5-fluoropyridin-2-yl)ethyl]-3-methyl-5-nitropyridine-2,6-diamine Obtained as an orange solid (88%) from 6-chloro-N-(5-chloro-2-methoxypyridin-3-yl)-5-methyl-3-nitropyridin-2-amine (Preparation 25a) and (S)-1-(5-fluoropyridin-2-yl)ethanamine (prepared according to the method described in WO2006/82392A1) following the experimental procedure as described in Preparation 22b.
$^1$H-NMR δ (250 MHz, CDCl$_3$): 1.65 (d, 3H), 2.20 (s, 3H), 4.07 (s, 3H), 5.41 (m, 1H), 6.97 (d, 1H), 7.40 (m, 2H), 7.80 (d, 1H), 8.11 (br.s., 1H), 8.45 (d, 1H), 9.07 (d, 1H), 11.25 (br. S., 1H)

c) N$^2$-(5-Chloro-2-methoxypyridin-3-yl)-N$^6$-[(1S)-1-(5-fluoropyridin-2-yl)ethyl]-5-methylpyridine-2,3,6-triamine Raney®-Nickel (0.7 g) was added to a solution of N$^6$-(5-chloro-2-methoxypyridin-3-yl)-N$^2$-[(1S)-1-(5-fluoropyridin-2-yl)ethyl]-3-methyl-5-nitropyridine-2,6-diamine (Preparation 25b, 0.67 g, 1.56 mmol) in ethanol (15 mL) and the resulting mixture was stirred at ambient temperature for 2 hours under a hydrogen atmosphere. The mixture was then filtered through Celite® and the filter cake was washed with methanol (30 mL). The combined filtrate and washings containing the title compound as a methanolic solution were concentrated under reduced pressure to half of their volume and were used in the next synthetic step without further purification.

d) 3-(5-Chloro-2-methoxypyridin-3-yl)-N-[(1S)-1-(5-fluoropyridin-2-Methyl]-6-methyl-3H-imidazo[4,5-b]pyridin-5-amine Obtained as a green oil (33%, two steps) from N$^2$-(5-chloro-2-methoxypyridin-3-yl)-N$^6$-[(1S)-1-(5-fluoropyridin-2-yl)ethyl]-5-methylpyridine-2,3,6-triamine (Preparation 25c) and formamidine acetate following the experimental procedure as described in Preparation 22d followed by purification by flash chromatography (20-40% acetone/hexanes).
$^1$H-NMR δ (250 MHz, CDCl$_3$): 1.57 (d, 3H), 2.30 (s, 3H), 3.99 (s, 3H), 5.26 (m, 1H), 5.39 (d, 1H), 7.33 (m, 2H), 7.69 (s, 1H), 8.16 (m, 3H), 8.39 (br.s., 1H).

Example 1

3-Oxo-3-((3R)-3-{[3-(2-oxo-1,2-dihydropyridin-3-yl)imidazo[1,2-b]pyridazin-6-yl]amino}piperidin-1-yl)propanenitrile A mixture of 3-((3R)-3-{[3-(2-methoxypyridin-3-yl)imidazo[1,2-b]pyridazin-6-yl]amino}piperidin-1-yl)-3-oxopropanenitrile (Preparation 3c, 58 mg, 0.15 mmol), chloro(trimethyl)silane (0.06 mL, 0.44 mmol) and sodium iodide (67 mg, 0.45 mmol) in acetonitrile (1.5 mL) was stirred at 80° C. for 50 minutes. The solvent was removed under reduced pressure and the residue was treated with water. The precipitate obtained was filtered, washed with more water and diethyl ether and dried in vacuo to give a solid that was purified by reverse phase chromatography (100% water to 1:1 water/(acetonitrile/methanol 1:1)) to yield the title compound (20 mg, 35%) as a solid.

LRMS (m/z): 378 (M+1)$^+$.

$^1$H-NMR δ (300 MHz, CD$_3$COD): 1.45-1.72 (m, 2H), 1.73-1.88 (m, 1H), 2.04 (dd, 1H), 2.63-2.78 (m, 1H), 3.21 (s, 2H), 3.53-3.90 (m, 3H), 4.60-4.71 (m, 1H), 6.47 (t, 1H), 6.54-6.72 (m, 2H), 7.23-7.42 (m, 1H), 7.53-7.64 (m, 1H), 8.29 (s, 1H), 8.57 (d, 1H), 9.01 (d, 1H).

Example 2

3-(6-{[(1S)-1-Phenylethyl]amino}imidazo[1,2-b]pyridazin-3-yl)pyridin-2(1H)-one

Obtained as a brown solid (56%) from 3-(2-methoxypyridin-3-yl)-N-[(1S)-1-phenylethyl]imidazo[1,2-b]pyridazin-6-amine (Preparation 4) following the experimental procedure as described in Example 1 followed by purification by reverse phase chromatography (100% water to 2:3 water/(acetonitrile/methanol 1:1)).

LRMS (m/z): 332 (M+1)$^+$.

$^1$H-NMR δ (300 MHz, CD$_3$OD): 1.55 (d, 3H), 3.53-3.67 (m, 1H), 3.73 (d, 1H), 6.30-6.45 (m, 1H), 6.86 (d, 1H), 7.12-7.26 (m, 1H), 7.29-7.48 (m, 5H), 7.65 (d, 1H), 8.30 (br. s., 1H), 8.38 (d, 1H).

Example 3

3-(6-{[(1S)-1-(5-Fluoropyridin-2-yl)ethyl]amino}imidazo[1,2-b]pyridazin-3-yl) pyridin-2(1H)-one Obtained as a yellow solid (64%) from N-[(1S)-1-(5-fluoropyridin-2-yl)ethyl]-3-(2-methoxypyridin-3-yl)imidazo[1,2-b]pyridazin-6-amine (Preparation 5) following the experimental procedure as described in Example 1 followed by purification by reverse phase chromatography (100% water to 2:3 water/(acetonitrile/methanol 1:1)).

LRMS (m/z): 351 (M+1)$^+$.

$^1$H-NMR δ (300 MHz, DMSO-d$_6$): 1.51 (d, 3H), 4.91 (t, 1H), 6.17-6.33 (m, 1H), 6.86 (d, 1H), 7.31 (d, 1H), 7.43-7.54 (m, 1H), 7.65 (t, 1H), 7.71-7.86 (m, 2H), 8.34-8.43 (m, 2H), 8.57 (br. s., 1H).

Example 4

3-(6-{[(1R)-1-(5-Fluoropyridin-2-yl)ethyl]amino}imidazo[1,2-b]pyridazin-3-yl) pyridin-2(1H)-one Obtained as a yellow solid (42%) from N-[(1S)-1-(5-fluoropyridin-2-yl)ethyl]-3-(2-methoxypyridin-3-yl)imidazo[1,2-b]pyridazin-6-amine (Preparation 6) following the experimental procedure as described in Example 1 followed by purification by reverse phase chromatography (100% water to 3:2 water/(acetonitrile/methanol 1:1)).

LRMS (m/z): 351 (M+1)$^+$.

$^1$H-NMR δ (300 MHz, CD$_3$OD): 1.59 (d, 3H), 4.97 (q, 1H), 6.43 (t, 1H), 6.89 (d, 1H), 7.36 (d, 1H), 7.52 (d, 2H), 7.70 (d, 1H), 8.34 (s, 1H), 8.42-8.50 (m, 2H).

Example 5

3-(6-{[(1S)-1-(5-Fluoropyrimidin-2-yl)ethyl]amino}imidazo[1,2-b]pyridazin-3-yl)pyridin-2(1H)-one Obtained as a brown solid (56%) from N-[(1R)-1-(5-fluoropyrimidin-2-yl)ethyl]-3-(2-methoxypyridin-3-yl)imidazo[1,2-b]pyridazin-6-amine (Preparation 7) following the experimental procedure as described in Example 1 followed by purification by reverse phase chromatography (100% water to 3:2 water/(acetonitrile/methanol 1:1)).

LRMS (m/z): 352 (M+1)$^+$.

$^1$H-NMR δ (300 MHz, CD$_3$OD): 1.64 (d, 3H), 5.08-5.23 (m, 1H), 6.47-6.61 (m, 1H), 6.93 (d, 1H), 7.40 (d, 1H), 7.71 (d, 1H), 8.38 (s, 1H), 8.65-8.77 (m, 3H).

Example 6

4-(6-{[(1S)-1-Phenylethyl]amino}imidazo[1,2-b]pyridazin-3-yl)pyridazin-3(2H)-one Obtained as a yellow solid (26%) from 3-(3-methoxypyridazin-4-yl)-N-[(1S)-1-phenyl ethyl]imidazo[1,2-b]pyridazin-6-amine (Preparation 9b) following the experimental procedure as described in Example 1 followed by purification by reverse phase chromatography (100% water to 2:3 water/(acetonitrile/methanol 1:1)).

LRMS (m/z): 333 (M−1-1)$^+$.

$^1$H-NMR δ (300 MHz, CD$_3$OD): 1.58 (d, 3H), 3.27-3.33 (m, 1H), 6.96 (d, 1H), 7.22 (t, 1H), 7.37 (t, 2H), 7.42-7.50 (m, 2H), 7.72 (d, 1H), 7.80 (d, 1H), 8.20 (d, 1H), 8.57 (s, 1H), 8.55-8.60 (m, 1H).

Example 7

5-Fluoro-3-(6-{[(1S)-1-(5-fluoropyridin-2-yl)ethyl]amino}imidazo[1,2-b]pyridazin-3-yl)pyridin-2(1H)-one Obtained as a yellow solid (95%) from 3-(5-fluoro-2-methoxypyridin-3-yl)-N-[(1S)-1-(5-fluoropyridin-2-yl)ethyl]imidazo-[1,2-b]pyridazin-6-amine (Preparation 12) following the experimental procedure as described in Example 1.

LRMS (m/z): 369 (M+1)$^+$.

$^1$H-NMR δ (300 MHz, DMSO-d$_6$): 1.58 (d, 3H), 4.85-5.12 (m, 1H), 6.96 (d, 1H), 7.52 (br. s., 2H), 7.60-7.74 (m, 1H), 7.88 (d, 2H), 8.40-8.71 (m, 3H), 11.88 (br. s., 1H).

Example 8

5-Chloro-3-(6-{[(1S)-1-(5-fluoropyridin-2-yl)ethyl]amino}imidazo[1,2-b]pyridazin-3-yl)pyridin-2(1H)-one Obtained as a brown solid (57%) from 3-(5-chloro-2-methoxypyridin-3-yl)-N-[(1S)-1-(5-fluoropyridin-2-yl)ethyl]imidazo-[1,2-b]pyridazin-6-amine (Preparation 15) following the experimental procedure as described in Example 1.

LRMS (m/z): 385 (M+1)$^+$.

$^1$H-NMR δ (300 MHz, DMSO-d$_6$): 1.57 (d, 3H), 4.93-5.12 (m, 1H), 7.10 (d, 1H), 7.51 (dd, 1H), 7.61-7.74 (m, 2H), 7.93 (d, 1H), 8.07 (d, 1H), 8.52 (d, 1H), 8.58 (s, 1H), 8.75 (d, 1H), 12.33 (br. s., 1H).

Example 9

3-(6-{[(1S)-1-(5-Fluoropyridin-2-yl)ethyl]amino}-7-methylimidazo[1,2-b]pyridazin-3-yl)pyridin-2(1H)-one Obtained as a beige solid (51%) from N-[(1S)-1-(5-fluoropyridin-2-yl)ethyl]-3-(2-methoxypyridin-3-yl)-7-methylimidazo-[1,2-b]pyridazin-6-amine (Preparation 18) following the experimental procedure as described in Example 1.
LRMS (m/z): 365 (M+1)$^+$.
$^1$H-NMR δ (300 MHz, DMSO-d$_6$): 1.63 (d, 3H), 2.43 (s, 3H), 4.93-5.18 (m, 1H), 6.29 (t, 1H), 6.87 (d, 1H), 7.33 (d, 1H), 7.50-7.61 (m, 1H), 7.62-7.71 (m, 1H), 7.74 (s, 1H), 8.38-8.49 (m, 2H), 8.61 (br. s., 1H), 11.84 (br. s., 1H).

Example 10

5-Fluoro-3-(6-{[(1S)-1-(5-fluoropyridin-2-yl)ethyl]amino}-7-methylimidazo[1,2-b]pyridazin-3-yl)pyridin-2(1H)-one Obtained as a solid (99%) from 3-(5-fluoro-2-methoxypyridin-3-yl)-N-[(1S)-1-(5-fluoropyridin-2-yl)ethyl]-7-methyl-imidazo[1,2-b]pyridazin-6-amine (Preparation 20) following the experimental procedure as described in Example 1.
LRMS (m/z): 382 (M+1)$^+$.
$^1$H-NMR δ (300 MHz, DMSO-d$_6$): 1.61 (d, 3H), 2.39 (s, 3H), 4.97-5.15 (m, 1H), 6.89 (d, 1H), 7.41-7.55 (m, 2H), 7.55-7.67 (m, 1H), 7.74 (s, 1H), 8.36-8.61 (m, 2H).

Example 11

5-Fluoro-3-(6-{[(1S)-1-(5-fluoropyrimidin-2-yl)ethyl]amino}imidazo[1,2-b]pyridazin-3-yl)pyridin-2(1H)-one Obtained as a yellow solid (14%) from 3-(5-fluoro-2-methoxypyridin-3-yl)-N-[(1S)-1-(5-fluoropyrimidin-2-yl)ethyl]imidazo[1,2-b]pyridazin-6-amine (Preparation 21b) following the experimental procedure as described in Example 1 followed by purification by preparative thin layer chromatography (1:9 methanol/dichloromethane).
$^1$H-NMR δ (250 MHz, DMSO-d$_6$): 1.57 (d, 3H), 4.97-5.13 (m, 1H), 6.91 (d, 1H), 7.49 (t, 1H), 7.81 (d, 1H), 7.89 (d, 1H), 8.47 (s, 1H), 8.60 (dd, 1H), 8.78 (s, 2H), 11.87 (br. s, 1H).

Example 12

3-(5-{[(1S)-1-(5-Fluoropyridin-2-yl)ethyl]amino}-3H-imidazo[4,5-b]pyridin-3-yl)pyridin-2(1H)-one Obtained as a pink solid (48%) from N-[(1S)-1-(5-fluoropyridin-2-yl)ethyl]-3-(2-methoxy pyridin-3-yl)-3H-imidazo[4,5-b]pyridin-5-amine (Preparation 22d) following the experimental procedure as described in Example 1 followed by purification by reverse phase chromatography (methanol to 95:5 water/methanol).
LRMS (m/z): 351 (M+1)$^+$.

$^1$H-NMR δ (250 MHz, DMSO-d$_6$): 1.45 (d, 3H), 4.86-4.99 (m, 1H), 6.31 (t, 1H), 6.59 (d, 1H), 7.28-7.47 (m, 3H), 7.54-7.65 (m, 1H), 7.66-7.77 (m, 2H), 8.44 (s, 1H), 8.50 (s, 1H), 12.25 (br.s., 1H).

Example 13

5-Chloro-3-(5-{[(1S)-1-(5-fluoropyridin-2-yl)ethyl]amino}-3H-imidazo[4,5-b]pyridin-3-yl)pyridin-2(1H)-one A suspension of 3-(5-chloro-2-methoxypyridin-3-yl)-N-[(1S)-1-(5-fluoropyridin-2-yl)ethyl]-3H-imidazo[4,5-b]pyridin-5-amine (Preparation 24d, 69 mg, 0.17 mmol) in aqueous hydrogen bromide solution (48%, 0.6 mL) was heated to 100° C. for 3 hours. After cooling to ambient temperature, water was removed under reduced pressure and the residue was treated with acetonitrile. The solid was filtered, washed with acetonitrile and dried to give the title compound as a hydrobromide salt (80 mg). The solid was then added to a stirred solution of aqueous saturated potassium carbonate (10 mL) and the resulting suspension was stirred for 2 hours. Ethyl acetate (15 mL) was added and the aqueous layer was separated and washed with ethyl acetate (2×15 mL). The combined organic extracts were dried over sodium sulphate and the solvents evaporated in vacuo to yield the title compound (44 mg, 66%) as a pink solid.
LRMS (m/z): 385 (M+1)$^+$.
$^1$H-NMR δ (300 MHz, CDCl$_3$): 1.53 (d, 3H), 5.03 (d, 1H), 6.61 (d, 1H), 7.42-7.48 (m, 2H), 7.69 (s, 2H), 7.71 (bs, 1H), 8.36 (s, 1H), 8.46 (s, 1H).

Example 14

5-Chloro-3-(5-{[(1S)-1-(5-fluoropyridin-2-yl)ethyl]amino}-6-methyl-3H-imidazo[4,5-b]pyridin-3-yl)pyridin-2(1H)-one Obtained as a beige solid (62%) from 3-(5-chloro-2-methoxypyridin-3-yl)-N-[(1S)-1-(5-fluoropyridin-2-yl)ethyl]-6-methyl-3H-imidazo[4,5-b]pyridin-5-amine (Preparation 25d) following the experimental procedure as described in Example 1.
LRMS (m/z): 399 (M+1)$^+$.
$^1$H-NMR δ (400 MHz, DMSO-d$_6$): 1.55 (d, 3H), 2.26 (s, 3H), 5.20 (m, 1H), 6.04 (br.s., 1H), 7.40 (dd, 1H), 7.49 (m, 2H), 7.63 (s, 1H), 8.15 (m, 1H), 8.40 (d, 1H), 8.51 (s, 1H), 12.11 (br.s., 1H).

Following a similar procedure to that described above, the following compounds were obtained:

Example 15

(S)-5-(Difluoromethyl)-3-(6-(1-(5-fluoropyridin-2-yl)ethylamino)imidazo[1,2-b]pyridazin-3-yl)pyridin-2(1H)-one Example 16

(S)-3-(6-(1-(5-Fluoropyridin-2-yl)ethylamino)imidazo[1,2-b]pyridazin-3-yl)-5-methylpyridin-2(1H)-one Example 17

(S)-3-(6-(1-(5-Fluoropyridin-2-Methylamino)-8-(2-methoxyethoxy)imidazo[1,2-b]pyridazin-3-yl)pyridin-2(1H)-one

Example 18

(S)-3-(6-(1-(5-Fluoropyridin-2-yl)ethylamino)-8-(4-(methylsulfonyl)piperazin-1-yl)imidazo[1,2-b]pyridazin-3-yl)pyridin-2(1H)-one

Example 19

(S)-3-(6-(1-(5-Fluoropyrimidin-2-yl)ethylamino)-7-methylimidazo[1,2-b]pyridazin-3-yl)pyridin-2(1H)-one

Example 20

(S)-5-Fluoro-3-(6-(1-(5-fluoropyrimidin-2-yl)ethylamino)-7-methylimidazo[1,2-b]pyridazin-3-yl)pyridin-2(1H)-one

Example 21

(S)-5-(6-(1-(5-fluoropyridin-2-yl)ethylamino)imidazo[1,2-b]pyridazin-3-yl)pyrimidin-4(3H)-one Pharmacological Activity
In Vitro JAK Kinase Assays Compounds were screened for their ability to inhibit JAK1, JAK2 and JAK3 using the assays as indicated below.

The catalytic domains of human JAK1 (aa 850-1154), JAK2 (aa 826-1132), JAK3 (aa 795-1124) and Tyk2 (aa 871-1187) were expressed as N-terminal GST-fusion proteins using a baculovirus expression system and were purchased from Carna Biosciences. The enzymatic activity was assayed using as substrate a biotinylated peptide, poly (GT)-Biotin (CisBio). The peptide concentration in the reactions was 60 nM for JAK1, nM for JAK2, 140 nM for JAK3 and 50 nM for Tyk2. The degree of phosphorylation was detected by TR-FRET (time-resolved fluorescence energy transfer).

$IC_{50}$s of compounds were measured for each kinase in a reaction mixture containing the enzyme, ATP and the peptide in 8 mM MOPS (pH 7.0), 10 mM $MgCl_2$, 0.05% 8-mercaptoethanol, 0.45 mg/ml BSA. The ATP concentration in the reactions was 3 μM for JAK1, 0.2 μM for JAK2, 0.6 μM for JAK3 and 1.8 μM for Tyk2. The enzymatic reactions took place for 30 minutes at room temperature. Then, the reactions were stopped with 20 μL of quench detection buffer (50 mM HEPES, 0.5 M KF, EDTA 0.25 M, 0.1% (w/v) BSA, pH 7.5) containing 0.115 μg/mL of anti-phosphoTyr (PT66)-Cryptate (CisBio) and a variable concentration of SA-XL665 (CisBio) to keep the SA-B ratio constant. Incubate for 3 h and read on Victor 2V spectrofluorometer (PerkinElmer) set to read fluorescence resonance energy transfer.

Some of the acronyms used above have the following meaning:
AA: aminoacids
GST: glutathione-S-transferase
MOPS: 3-(N-morpholino)propane sulfonic acid
BSA: bovine serum albumin
ATP: adenosine tri-phosphate
EDTA: ethylenediaminetetraacetic acid
HEPES: 4-(2-hydroxyethyl)-1-piperazineethanesulfonic acid Table 1 depicts $IC_{50}$ values for certain exemplary compounds described in the invention. In Table 1, "A" represents an $IC_{50}$ value of less than 0.1 μM (100 nM), "B" represents an $IC_{50}$ value in the range of 0.1 μM (100 nM) to 1 μM (1000 nM), and C represents an $IC_{50}$ value higher than 1 μM (1000 nM).

TABLE 1

| Example No. | $IC_{50}$ JAK3 (μM) | $IC_{50}$ JAK2 (μM) | $IC_{50}$ JAK1 (μM) |
|---|---|---|---|
| 1 | A | A | A |
| 4 | A | A | B |
| 5 | A | A | A |
| 6 | A | A | B |
| 8 | A | A | A |
| 9 | A | A | A |
| 13 | A | A | A |

It can be seen from Table 1 that the compounds of formula (I) are potent inhibitors of JAK1, JAK2 and JAK3 kinases. Our results show that the compounds of formula (I) are potent inhibitors of JAK1, JAK2 and JAK3 kinases having an $IC_{50}$ value for the inhibition of each JAK kinase (determined as defined above) of less than 1 μM. Preferred imidazo[1,2-b]pyridazine and imidazo[4,5-b]pyridine derivatives of the invention possess an $IC_{50}$ value for the inhibition of each JAK kinase of less than 0.8 μM, preferably of less than 0.5 μM, more preferably of less than 0.2 μM.

The invention is also directed to a compound of the invention as described herein for use in the treatment of the human or animal body by therapy. Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

Combinations

The imidazo[1,2-b]pyridazine and imidazo[4,5-b]pyridine derivatives defined herein may also be combined with other active compounds in the treatment of a pathological condition or disease susceptible to amelioration by inhibition of Janus Kinases.

The combinations of the invention can optionally comprise one or more additional active substances which are known to be useful in the treatment of myeloproliferative disorders (such as polycythemia vera, essential thrombocythemia or mielofibrosis), leukemia, lymphoid malignancies and solid tumors; bone marrow and organ transplant rejection; immune-mediated diseases and inflammatory diseases, more in particular wherein the pathological condition or disease is selected from rheumatoid arthritis, multiple sclerosis, inflammatory bowel disease, dry eye, uveitis, allergic conjunctivitis, allergic rhinitis, asthma, chronic obstructive pulmonary disease (COPD), atopic dermatitis and psoriasis, such as (a) Dyhydrofolate reductase inhibitors, such as Methotrexate or CH-1504; (b) Dihydroorotate dehydrogenase (DHODH) inhibitors such as leflunomide, teriflunomide, or the compounds described in the International Patent Application Nos. WO2008/077639 and WO2009/021696; (c) Immunomodulators such as Glatiramer acetate (Copaxone), Laquinimod or Imiquimod; (d) Inhibitors of DNA synthesis and repair, such as Mitoxantrone or Cladribine; (e) Immunosuppressants, such as Imuran (azathioprine) or Purinethol (6-mercaptopurine or 6-MP); (f) Anti-alpha 4 integrin antibodies, such as Natalizumab (Tysabri); (g) Alpha 4 integrin antagonists such as R-1295, TBC-4746, CDP-323, ELND-002, Firategrast or TMC-2003; (h) Corticoids and glucocorticoids such as prednisone or methylprednisolone, fluticasone, mometasone, budesonide, ciclesonide or beta-metasone; (i) Fumaric acid esters, such as BG-12; (j) Anti-tumor necrosis factor-alpha (Anti-TNF-alpha), such as Infliximab, Adalimumab, or Certolizumab pegol; (k) Soluble Tumor necrosis factor-alpha (TNF-alpha) receptors such as Etanercept; (l) Anti-CD20 (lymphocyte protein) monoclonal antibodies such as Rituximab, Ocrelizumab Ofatumumab or TRU-015; (m) Anti-CD52 (lymphocyte protein) monoclonal antibodies such as alemtuzumab; (n) Anti-CD25 (lymphocyte protein) such as daclizumab; (O) Anti-CD88 (lymphocyte protein), such as eculizumab or pexilizumab; (p) Anti-Interleukin 6 Receptor (IL-6R), such as tocilizumab; (q) Anti-Interleukin 12 Receptor (IL-12R)/Interleukin 23 Receptor (IL-23R), such as ustekinumab; (r) Calcineurin inhibitors such as cyclosporine A or tacrolimus; (s) Inosine-monophosphate dehydrogenase (IMPDH) inhibitors, such as mycophenolate mophetyl, ribavirin, mizoribine or mycophenolic acid; (t) Cannabinoid receptor agonists such as Sativex; (u) Chemokine CCR1 antagonists such as MLN-3897 or PS-031291; (v) Chemokine CCR2 antagonists such as INCB-8696; (w) Necrosis factor-kappaB (NF-kappaB or NFKB) Activation Inhibitors such as Sulfasalazine, Iguratimod or MLN-0415; (x) Adenosine $A_{2A}$ agonists, such as ATL-313, ATL-146e, CGS-21680, Regadenoson or UK-432,097; (y) Sphingosine-1 (SIP) phosphate receptor agonists such as fingolimod, BAF-312, or ACT128800; (z) Sphingosine-1 (S1P) liase inhibitors such as LX2931; (aa) Spleen tyrosine kinase (Syk) inhibitors, such as R-112; (bb) Protein Kinase Inhibitors (PKC) inhibitors, such as NVP-AEB071; (cc) Anti-cholinergic agents such as tiotropium or aclidinium; (dd) Beta adrenergic agonists such as formoterol, indacaterol or abediterol (LAS100977); (ee) Compounds having bifunctional Muscarinic Antagonist-Beta2 Agonist activity (MABAs); (ff) Histamine 1 (H1) receptor antagonists, such as azelastine or ebastine; (gg) Chemoattractant receptor homologous molecule expressed on $TH_2$ cells (CRTH2) inhibitors, such as OC-459, AZD-1981, ACT-129968, QAV-680; (hh) Vitamin D derivatives like calcipotriol (Daivonex); (ii) Anti-inflammatory agents, such as non-steroidal anti-inflammatory drugs (NSAIDs) or selective cyclooxygenase-2 (COX-2) inhibitors such as aceclofenac, diclofenac, ibuprofen, naproxen, apricoxib, celecoxib, cimicoxib, deracoxib, etoricoxib, lumiracoxib, parecoxib sodium, rofecoxib, selenocoxib-1 or valdecoxib; (jj) Anti-allergic agents; (kk) Anti-viral agents; (ll) Phosphodiestearase (PDE) III inhibitors; (mm) Phosphosdiesterase (PDE) IV inhibitors such as roflumilast or GRC-4039; (nn) Dual Phosphodiestearase (PDE) III/IV inhibitors; (O) Xanthine derivatives, such as theophylline or theobromine; (pp) p38 Mitogen-Activated Protein Kinase (p38 MAPK) Inhibitors such as ARRY-797; (qq) Mitogen-activated extracellular signal regulated kinase kinase (MEK) inhibitor, such as ARRY-142886 or ARRY-438162; (rr) Phosphoinositide 3-Kinases (PI3Ks) inhibitors; (ss) Interferons comprising Interferon beta 1a such as Avonex from Biogen Idec, CinnoVex from CinnaGen and Rebif from EMD Serono, and Interferon beta 1b such as Betaferon from Schering and Betaseron from Berlex; and (tt) Interferon alpha such as Sumiferon MP.

Specific examples of suitable corticoids and glucocorticoids that can be combined with the JAK inhibitors of the present invention are prednisolone, methylprednisolone, dexamethasone, dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone farnesylate, ciclesonide, butixocort propionate, RPR-106541, deprodone propionate, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate and hydrocortisone probutate.

Specific examples of suitable Syk kinase inhibitors that can be combined with the JAK inhibitors of the present invention are fosfamatinib (from Rigel), R-348 (from Rigel), R-343 (from Rigel), R-112 (from Rigel), piceatannol, 2-(2-Aminoethylamino)-4-[3-(trifluoromethyl)phenylamino]pyrimidine-5-carboxamide, R-091 (from Rigel), 6-[5-Fluoro-2-(3,4,5-trimethoxyphenylamino)pyrimidin-4-ylamino]-2,2-dimethyl-3,4-dihydro-2H-pyrido[3,2-b][1,4]oxazin-3-one benzenesulfonate (R-406 from Rigel), 1-(2,4,6-Trihydroxyphenyl)-2-(4-methoxyphenyl)ethan-1-one, N-[4-[6-(Cyclobutylamino)-9H-purin-2-ylamino]phenyl]-N-methylacetamide (QAB-205 from Novartis), 2-[7-(3,4-Dimethoxyphenyl)imidazo[1,2-c]pyrimidin-5-ylamino]pyridine-3-carboxamide Specific examples of suitable corticoids and glucocorticoids that can be combined with the JAK inhibitors of the present invention are prednisolone, methylprednisolone, dexamethasone, dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone farnesylate, ciclesonide, butixocort propionate, RPR-106541, deprodone propionate, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate and hydrocortisone probutate.

Specific examples of suitable Syk kinase inhibitors that can be combined with the JAK inhibitors of the present invention are fosfamatinib (from Rigel), R-348 (from Rigel), R-343 (from Rigel), R-112 (from Rigel), piceatannol, 2-(2-Aminoethylamino)-4-[3-(trifluoromethyl)phenylamino]pyrimidine-5-carboxamide, R-091 (from Rigel), 6-[5-Fluoro-2-(3,4,5-trimethoxyphenylamino)pyrimidin-4-ylamino]-2,2-dimethyl-3,4-dihydro-2H-pyrido[3,2-b][1,4]oxazin-3-one benzenesulfonate (R-406 from Rigel), 1-(2,4,6-Trihydroxyphenyl)-2-(4-methoxyphenyl)ethan-1-one, N-[4-[6-(Cyclobutylamino)-9H-purin-2-ylamino]phenyl]-N-methylacetamide (QAB-205 from Novartis), 2-[7-(3,4-Dimethoxyphenyl)imidazo[1,2-c]pyrimidin-5-ylamino]pyridine-3-carboxamide dihydrochloride (BAY-61-3606 from Bayer) and AVE-0950 (from Sanofi-Aventis).

Specific examples of suitable M3 antagonists (anticholinergics) that can be combined with the JAK inhibitors of the present invention are tiotropium salts, oxitropium salts, flutropium salts, ipratropium salts, glycopyrronium salts, trospium salts, zamifenacin, revatropate, espatropate, darotropium bromide, CI-923, NPC-14695, BEA-2108, 3-[2-Hydroxy-2,2-bis(2-thienyl)acetoxy]-1-(3-phenoxypropyl)-1-azoniabicyclo[2.2.2]octane salts (in particular aclidinium salts, more preferably aclidinium bromide), 1-(2-Phenylethyl)-3-(9H-xanthen-9-ylcarbonyloxy)-1-azoniabicyclo[2.2.2]octane salts, 2-oxo-1,2,3,4-tetrahydroquinazoline-3- carboxylic acid endo-8-methyl-8-azabicyclo[3.2.1]oct-3-yl ester salts (DAU-5884), 3-(4-Benzylpiperazin-1-yl)-1-cyclobutyl-1-hydroxy-1-phenylpropan-2-one (NPC-14695), N-[1-(6-Aminopyridin-2-ylmethyl)piperidin-4-yl]-2(R)-[3,3-difluoro-1(R)-cyclopentyl]-2-hydroxy-2-phenylacetamide (J-104135), 2(R)-Cyclopentyl-2-hydroxy-N-[1-[4(S)-methylhexyl]piperidin-4-yl]-2-phenylacetamide (J-106366), 2(R)-Cyclopentyl-2-hydroxy-N-[1-(4-methyl-3-pentenyl)-4-piperidyl]-2-phenylacetamide (J-104129), 1-[4-(2-Aminoethyl)piperidin-1-yl]-2(R)[3,3-difluorocyclopent-[(R)-yl]-2-hydroxy-2-phenylethan-1-one (Banyu-280634), N—[N-[2N-[1-(Cyclohexylmethyl)piperidin-3(R)-ylmethyl]carbamoyl]ethyl]carbamoylmethyl]-3,3,3-triphenylpropionamide (Banyu CPTP), 2(R)-Cyclopentyl-2-hydroxy-2-phenylacetic acid 4-(3-azabicyclo[3.1.0]hex-3-yl)-2-butynyl ester (Ranbaxy 364057), 3(R)-[4,4-Bis(4-fluorophenyl)-2-oxoimidazolidin-1-yl]-1-methyl-1-[2-oxo-2-(3-thienyl)ethyl]pyrrolidinium iodide, N-[1-(3-Hydroxybenzyl)-1-methylpiperidinium-3(S)-yl]-N—[N-[4-(isopropoxycarbonyl)phenyl]carbamoyl]-L-tyrosinamide trifluoroacetate, UCB-101333, Merck's OrM3, 7-endo-(2-hydroxy-2,2-diphenylacetoxy)-9,9-dimethyl-3-oxa-9-azoniatricyclo[3.3.1.0(2,4)]nonane salts, 3(R)-[4,4-Bis(4-fluorophenyl)-2-oxoimidazolidin-1-yl]-1-methyl-1-(2-phenylethyl)pyrrolidinium iodide, trans-4-[2-[Hydroxy-2,2-(dithien-2-yl)acetoxy]-1-methyl-1-(2-phenoxyethyl) piperidinium bromide from Novartis (412682), 7-(2,2-diphenylpropionyloxy)-7,9,9-trimethyl-3-oxa-9-azoniatricyclo[3.3.1.0*2,4*]nonane salts, 7-hydroxy-7,9,9-trimethyl-3-oxa-9-azoniatricyclo[3.3.1.0*2,4]nonane 9-methyl-9H-fluorene-9-carboxylic acid ester salts, all of them optionally in the form of their racemates, their enantiomers, their diastereomers and mixtures thereof, and optionally in the form of their pharmacologically-compatible acid addition salts. Among the salts chlorides, bromides, iodides and methanesulphonates are preferred.

Specific examples of suitable beta adrenergic agonists (β2-agonists) that can be combined with the JAK inhibitors of the present invention are terbutaline sulphate, eformoterol fumarate, formoterol fumarate, bambuterol, ibuterol, isoprenaline hydrochloride, dopexamine, metaprotenerol, tulobuterol, procaterol hydrochloride, sibenadet hydrochloride, mabuterol hydrochloride, albuterol sulphate, salbutamol sulphate, salmefamol, salmeterol xinafoate, carmoterol hydrochloride, (R)-albuterol hydrochloride, Levalbuterol hydrochloride; Levosalbutamol hydrochloride; (−)-Salbutamol hydrochloride, formoterol, (R,R)-Formoterol tartrate; Arformoterol tartrate, sulfonterol, Bedoradrine sulphate, Indacaterol, Trantinterol hydrochloride, Milveterol hydrochloride, Olodaterol, fenoterol hydrobromide, rimoterol hydrobromide, riproterol hydrochloride, Vilanterol broxaterol, pirbuterol hydrochloride, bitolterol mesylate, clenbuterol hydrochloride, AZD-3199, GSK-159802; GSK-597901, GSK-678007, GSK-961081; 4-[2-[3-(1H-Benzimidazol-1-yl)-1,1-dimethylpropylamino]-1-hydroxyethyl]-2-(4-methoxybenzylamino)phenol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-domethoxyphenyl)-2-methyl-2-propylamino]ethanol, 1-[2H-5-hydroxy-3-oxo-4H-1,4-benzoxazin-8-yl]-2-[3-(4-n-butyloxyhenyl)-2-methyl-2-propylamino]ethanol, KUL-1248, HOKU-81, SM-110444, RP-58802B, LAS 100977 and compounds described in PCT patent applications Nos. WO 2007/124898, WO 2006/122788A1, WO 2008/046598, WO 2008095720, WO 2009/068177 and WO 2010/072354.

Specific examples of suitable Phosphosdiesterase IV (PDE IV) inhibitors that can be combined with the JAK inhibitors of the present invention are benafentrine dimaleate, etazolate, denbufylline, rolipram, cipamfylline, zardaverine, arofylline, filaminast, tipelukast, tofimilast, piclamilast, tolafentrine, mesopram, drotaverine hydrochloride, lirimilast, roflumilast, cilomilast, oglemilast, apremilast, tetomilast, filaminast, (R)-(+)-4-[2-(3-Cyclopentyloxy-4-methoxyphenyl)-2-phenylethyl]pyridine (CDP-840), N-(3,5-Dichloro-4-pyridinyl)-2-[1-(4-fluorobenzyl)-5-hydroxy-1H-indol-3-yl]-2-oxoacetamide (GSK-842470), 9-(2-Fluorobenzyl)-N6-methyl-2-(trifluoromethyl)adenine (NCS-613), N-(3,5-Dichloro-4-pyridinyl)-8-methoxyquinoline-5-carboxamide (D-4418), 3-[3-(Cyclopentyloxy)-4-methoxybenzyl]-6-(ethylamino)-8-isopropyl-3H-purine hydrochloride (V-11294A), 6-[3-(N,N-Dimethylcarbamoyl)phenylsulfonyl]-4-(3-methoxyphenylamino)-8-methylquinoline-3-carboxamide hydrochloride (GSK-256066), 4-[6,7-Diethoxy-2,3-bis(hydroxymethyl)naphthalen-1-yl]-1-(2-methoxyethyl) pyridin-2(1H)-one (T-440), (−)-trans-2-[3'-[3-(N-Cyclopropylcarbamoyl)-4-oxo-1,4-dihydro-1,8-naphthyridin-1-yl]-3-fluorobiphenyl-4-yl] cyclopropanecarboxylic acid, MK-0873, CDC-801, UK-500001, BLX-914, 2-carbomethoxy-4-cyano-4-(3-cyclopropylmethoxy-4-difluoromethoxyphenyl)cyclohexan1-one, cis[4-cyano-4-(3-cyclopropylmethoxy-4-difluoromethoxyphenyl)cyclohexan-1-ol, 5(S)-[3-(Cyclopentyloxy)-4-methoxyphenyl]-3(S)-(3-methylbenzyl)piperidin-2-one (IPL-455903), ONO-6126 (Eur Respir J 2003, 22(Suppl. 45): Abst 2557) and the compounds claimed in the PCT patent applications number WO 03/097613, WO 2004/058729, WO 2005/049581, WO 2005/123693, WO 2005/123692, and WO 2010/069504.

Examples of suitable Phosphoinositide 3-Kinases (PI3Ks) inhibitors that can be combined with the JAK inhibitors of the present invention are 2-Methyl-2-[4-[3-methyl-2-oxo-8-(3-quinolinyl)-2,3-dihydro-1H-imidazo[4,5-c]quinolin-1-yl] phenyl]propanenitrile (BEZ-235 from Novartis), CAL-101 (from Calistoga Pharmaceuticals) and N-Ethyl-N'-[3-(3,4,5-trimethoxyphenylamino)pyrido[2,3-b]pyrazin-6-yl]thiourea (AEZS-126 from Aeterna Zentaris).

The compounds of formula (I) and the combinations of the invention may be used in the treatment of myeloproliferative disorders, leukemia, lymphoid malignancies and solid tumors; bone marrow and organ transplant rejection; immune-mediated diseases and inflammatory diseases, wherein the use of a JAK inhibitor is expected to have a beneficial effect, for example rheumatoid arthritis, multiple sclerosis, inflammatory bowel disease (such as ulcerative colitis or Crohn's disease), dry eye, uveitis, allergic conjunctivitis, allergic rhinitis, asthma, chronic obstructive pulmonary disease (COPD), atopic dermatitis and psoriasis.

The active compounds in the combination product may be administered together in the same pharmaceutical composition or in different compositions intended for separate, simultaneous, concomitant or sequential administration by the same or a different route.

It is contemplated that all active agents would be administered at the same time, or very close in time. Alternatively, one or two actives could be administered in the morning and the other (s) later in the day. Or in another scenario, one or two actives could be administered twice daily and the other (s) once daily, either at the same time as one of the twice-a-day dosing occurred, or separately. Preferably at least two, and more preferably all, of the actives would be administered together at the same time. Preferably, at least two, and more preferably all actives would be administered as an admixture.

The invention is also directed to a combination product of the compounds of the invention together with one or more other therapeutic agents for use in the treatment of a pathological condition or disease susceptible to amelioration by inhibiton of Janus Kinases (JAK), in particular wherein the pathological condition or disease is selected from myeloproliferative disorders, leukemia, lymphoid malignancies and solid tumors; bone marrow and organ transplant rejection; immune-mediated diseases and inflammatory diseases, more in particular wherein the pathological condition or disease is selected from rheumatoid arthritis, multiple sclerosis, inflammatory bowel disease, dry eye, uveitis, allergic conjunctivitis, allergic rhinitis, asthma, chronic obstructive pulmonary disease (COPD), atopic dermatitis and psoriasis.

The invention also encompasses the use of a combination of the compounds of the invention together with one or more other therapeutic agents for the manufacture of a formulation or medicament for treating these diseases.

The invention also provides a method of treatment of a pathological condition or disease susceptible to amelioration by inhibition of Janus Kinases (JAK), in particular wherein the pathological condition or disease is selected from myeloproliferative disorders, leukemia, lymphoid malignancies and solid tumors; bone marrow and organ transplant rejection; immune-mediated diseases and inflammatory diseases, more in particular wherein the pathological condition or disease is selected from rheumatoid arthritis, multiple sclerosis, inflammatory bowel disease, dry eye, uveitis, allergic conjunctivitis, allergic rhinitis, asthma, chronic obstructive pulmonary disease (COPD), atopic dermatitis and psoriasis; comprising administering a therapeutically effective amount of a combination of the compounds of the invention together with one or more other therapeutic agents.

The active compounds in the combinations of the invention may be administered by any suitable route, depending on the nature of the disorder to be treated, e.g. orally (as syrups, tablets, capsules, lozenges, controlled-release preparations, fast-dissolving preparations, etc); topically (as creams, ointments, lotions, nasal sprays or aerosols, etc); by injection (subcutaneous, intradermic, intramuscular, intravenous, etc.) or by inhalation (as a dry powder, a solution, a dispersion, etc).

The active compounds in the combination, i.e. the imidazo[1,2-b]pyridazine and imidazo[4,5-b]pyridine derivatives of the invention, and the other optional active compounds may be administered together in the same pharmaceutical composition or in different compositions intended for separate, simultaneous, concomitant or sequential administration by the same or a different route.

One execution of the present invention consists of a kit of parts comprising a imidazo[1,2-b]pyridazine or imidazo[4,5-b]pyridine derivative of the invention together with instructions for simultaneous, concurrent, separate or sequential use in combination with another active compound useful in the treatment of myeloproliferative disorders, leukemia, lymphoid malignancies and solid tumors; bone marrow and organ transplant rejection; immune-mediated diseases and inflammatory diseases, more in particular useful in the treatment of rheumatoid arthritis, multiple sclerosis, inflammatory bowel disease, dry eye, uveitis, allergic conjunctivitis, allergic rhinitis, asthma, chronic obstructive pulmonary disease (COPD), atopic dermatitis and psoriasis.

Another execution of the present invention consists of a package comprising a imidazo[1,2-b]pyridazine or imidazo[4,5-b]pyridine derivative of the invention and another active compound useful in the treatment of myeloproliferative disorders, leukemia, lymphoid malignancies and solid tumors; bone marrow and organ transplant rejection; immune-mediated diseases and inflammatory diseases, more in particular useful in the treatment of rheumatoid arthritis, multiple sclerosis, inflammatory bowel disease, dry eye, uveitis, allergic conjunctivitis, allergic rhinitis, asthma, chronic obstructive pulmonary disease (COPD), atopic dermatitis and psoriasis.

Pharmaceutical Compositions

Pharmaceutical compositions according to the present invention comprise the compounds of the invention in association with a pharmaceutically acceptable diluent or carrier.

As used herein, the term pharmaceutical composition refers to a mixture of one or more of the compounds described herein, or physiologically/pharmaceutically acceptable salts, solvates, N-oxides, stereoisomers, deuterated derivatives thereof or prodrugs thereof, with other chemical components, such as physiologically/pharmaceutically acceptable carriers and excipients. The purpose of a pharmaceutical composition is to facilitate administration of a compound to an organism.

As used herein, a physiologically/pharmaceutically acceptable diluent or carrier refers to a carrier or diluent that does not cause significant irritation to an organism and does not abrogate the biological activity and properties of the administered compound.

The invention further provides pharmaceutical compositions comprising the compounds of the invention in association with a pharmaceutically acceptable diluent or carrier together with one or more other therapeutic agents for use in the treatment of a pathological condition or disease susceptible to amelioration by inhibition of Janus Kinases (JAK), such as the ones previously described.

The invention is also directed to pharmaceutical compositions of the invention for use in the treatment of a pathological condition or disease susceptible to amelioration by inhibition of Janus Kinases (JAK), in particular wherein the pathological condition or disease is selected from myeloproliferative disorders, leukemia, lymphoid malignancies and solid tumors; bone marrow and organ transplant rejection; immune-mediated diseases and inflammatory diseases, more in particular wherein the pathological condition or disease is selected from rheumatoid arthritis, multiple sclerosis, inflammatory bowel disease, dry eye, uveitis, allergic conjunctivitis, allergic rhinitis, asthma, chronic obstructive pulmonary disease (COPD), atopic dermatitis and psoriasis. The invention also encompasses the use of a pharmaceutical composition of the invention for the manufacture of a medicament for treating these diseases.

The invention also provides a method of treatment of a pathological condition or disease susceptible to amelioration by inhibition of Janus Kinases (JAK), in particular wherein the pathological condition or disease is selected from myeloproliferative disorders, leukemia, lymphoid malignancies and solid tumors; bone marrow and organ transplant rejection; immune-mediated diseases and inflammatory diseases, more in particular wherein the pathological condition or disease is selected from rheumatoid arthritis, multiple sclerosis, inflammatory bowel disease, dry eye, uveitis, allergic conjunctivitis, allergic rhinitis, asthma, chronic obstructive pulmonary disease (COPD), atopic dermatitis and psoriasis, comprising administering a therapeutically effective amount of a pharmaceutical composition of the invention.

The present invention also provides pharmaceutical compositions which comprise, as an active ingredient, at least a compound of formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight, of the composition depending upon the nature of the formulation and whether further dilution is to be made prior to application. Preferably the compositions are made up in a form suitable for oral, inhalation, topical, nasal, rectal, percutaneous or injectable administration.

Pharmaceutical compositions suitable for the delivery of compounds of the invention and methods for their preparation will be readily apparent to those skilled in the art. Such compositions and methods for their preparation can be found, for example, in Remington: The Science and Practice of Pharmacy, 21st Edition, Lippincott Williams & Wilkins, Philadelphia, Pa., 2001.

The pharmaceutically acceptable excipients which are admixed with the active compound or salts of such compound, to form the compositions of this invention are well-known per se and the actual excipients used depend inter alia on the intended method of administering the compositions. Examples, without limitation, of excipients include calcium carbonate, calcium phosphate, various sugars and types of starch, cellulose derivatives, gelatin, vegetable oils and polyethylene glycols.

Additional suitable carriers for formulations of the compounds of the present invention can be found in Remington: The Science and Practice of Pharmacy, 21st Edition, Lippincott Williams & Wilkins, Philadelphia, Pa., 2001.

i) Oral Administration

The compounds of the invention may be administered orally (peroral administration; per os (latin)). Oral administration involve swallowing, so that the compound is absorbed from the gut and delivered to the liver via the portal circulation (hepatic first pass metabolism) and finally enters the gastrointestinal (GI) tract.

Compositions for oral administration may take the form of tablets, retard tablets, sublingual tablets, capsules, inhalation aerosols, inhalation solutions, dry powder inhalation, or liquid preparations, such as mixtures, solutions, elixirs, syrups or suspensions, all containing the compound of the invention; such preparations may be made by methods well-known in the art. The active ingredient may also be presented as a bolus, electuary or paste.

Where the composition is in the form of a tablet, any pharmaceutical carrier routinely used for preparing solid formulations may be used. Examples of such carriers include magnesium stearate, talc, gelatine, acacia, stearic acid, starch, lactose and sucrose.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent.

Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet. Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant. Tablet blends may be compressed directly or by roller to form tablets. Tablet blends or portions of blends may alternatively be wet-, dry-, or melt-granulated, melt congealed, or extruded before tabletting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., 1980. Where the composition is in the form of a capsule, any routine encapsulation is suitable, for example using the aforementioned carriers in a hard gelatine capsule. Where the composition is in the form of a soft gelatine capsule any pharmaceutical carrier routinely used for preparing dispersions or suspensions may be considered, for example aqueous gums, celluloses, silicates or oils, and are incorporated in a soft gelatine capsule.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent. Liquid formulations may also be prepared by the reconstitution of a solid, for example, from a sachet.

ii) Oral Mucosal Administration

The compounds of the invention can also be administered via the oral mucosal. Within the oral mucosal cavity, delivery of drugs is classified into three categories: (a) sublingual delivery, which is systemic delivery of drugs through the mucosal membranes lining the floor of the mouth, (b) buccal delivery, which is drug administration through the mucosal membranes lining the cheeks (buccal mucosa), and (c) local delivery, which is drug delivery into the oral cavity.

Pharmaceutical products to be administered via the oral mucosal can be designed using mucoadhesive, quick dissolve tablets and solid lozenge formulations, which are formulated with one or more mucoadhesive (bioadhesive) polymers (such as hydroxy propyl cellulose, polyvinyl pyrrolidone, sodium carboxymethyl cellulose, hydroxy propyl methyl cellulose, hydroxy ethyl cellulose, polyvinyl alcohol, polyisobutylene or polyisoprene); and oral mucosal permeation enhancers (such as butanol, butyric acid, propranolol, sodium lauryl sulphate and others)

iii) Inhaled Administration

The compounds of the invention can also be administered by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge may generally contain between 0.001-50 mg, more preferably 0.01-5 mg of active ingredient or the equivalent amount of a pharmaceutically acceptable salt thereof. Alternatively, the active ingredient(s) may be presented without excipients.

Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices.

For inhalers of the first type, single doses have been weighed by the manufacturer into small containers, which are mostly hard gelatine capsules. A capsule has to be taken from a separate box or container and inserted into a receptacle area of the inhaler.

Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients.

Other drawbacks related to the use of hard gelatine capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported (e.g. Nielsen et al, 1997).

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e.g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (Ex. EP0069715) or disks (Ex. GB 2041763; EP 0424790; DE 4239402 and EP 0674533), rotatable cylinders (Ex. EP 0166294; GB 2165159 and WO 92/09322) and rotatable frustums (Ex. WO 92/00771), all having cavities which have to be filled with powder from the container. Other multi dose devices have measuring slides (Ex. U.S. Pat. No. 5,201,308 and WO 97/00703) or measuring plungers with a local or circumferential recess to displace a certain volume of powder from the container to a delivery chamber or an air conduit (Ex. EP 0505321, WO 92/04068 and WO 92/04928), or measuring slides such as the Genuair® (formerly known as Novolizer SD2FL), which is described the following patent applications Nos: WO97/000703, WO03/000325 and WO2006/008027.

Reproducible dose measuring is one of the major concerns for multi dose inhaler devices.

The powder formulation has to exhibit good and stable flow properties, because filling of the dose measuring cups or cavities is mostly under the influence of the force of gravity.

For reloaded single dose and multiple unit dose inhalers, the dose measuring accuracy and reproducibility can be guaranteed by the manufacturer. Multi dose inhalers on the other hand, can contain a much higher number of doses, whereas the number of handlings to prime a dose is generally lower.

Because the inspiratory air stream in multi-dose devices is often straight across the dose measuring cavity, and because the massive and rigid dose measuring systems of multi dose inhalers can not be agitated by this inspiratory air stream, the powder mass is simply entrained from the cavity and little de-agglomeration is obtained during discharge.

Consequently, separate disintegration means are necessary. However in practice, they are not always part of the inhaler design. Because of the high number of doses in multi-dose devices, powder adhesion onto the inner walls of the air conduits and the de-agglomeration means must be minimized and/or regular cleaning of these parts must be possible, without affecting the residual doses in the device. Some multi dose inhalers have disposable drug containers that can be replaced after the prescribed number of doses has been taken (Ex. WO 97/000703). For such semi-permanent multi dose inhalers with disposable drug containers, the requirements to prevent drug accumulation are even more strict.

Apart from applications through dry powder inhalers the compositions of the invention can be administered in aerosols which operate via propellant gases or by means of so-called atomisers, via which solutions of pharmacologically-active substances can be sprayed under high pressure so that a mist of inhalable particles results. The advantage of these atomisers is that the use of propellant gases can be completely dispensed with. Such atomiser is the Respimat® which is described, for example, in PCT Patent Applications Nos. WO 91/14468 and WO 97/12687, reference here is being made to the contents thereof.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the active ingredient (s) and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant.

The aerosol composition may be excipient free or may optionally contain additional formulation excipients well known in the art such as surfactants (eg oleic acid or lecithin) and cosolvens (eg ethanol). Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1-10 µm, preferably 2-5 µm. Particles having a size above 20 µm are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline.

Achieving high dose reproducibility with micronised powders is difficult because of their poor flowability and extreme agglomeration tendency. To improve the efficiency of dry powder compositions, the particles should be large while in the inhaler, but small when discharged into the respiratory tract. Thus, an excipient such as lactose or glucose is generally employed. The particle size of the excipient will usually be much greater than the inhaled medicament within the present invention. When the excipient is lactose it will typically be present as milled lactose, preferably crystalline alpha lactose monohydrate.

Pressurized aerosol compositions will generally be filled into canisters fitted with a valve, especially a metering valve. Canisters may optionally be coated with a plastics material e.g. a fluorocarbon polymer as described in WO96/32150. Canisters will be fitted into an actuator adapted for buccal delivery.

iv) Nasal Mucosal Administration

The compounds of the invention may also be administered via the nasal mucosal. Typical compositions for nasal mucosa administration are typically applied by a metering, atomizing spray pump and are in the form of a solution or suspension in an inert vehicle such as water optionally in combination with conventional excipients such as buffers, anti-microbials, tonicity modifying agents and viscosity modifying agents.

v) Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art. The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

vi) Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and microneedle or needle-free injection.

Formulations for topical administration may be formulated to be immediate and/or modified release. Modified release formulations include delayed-, sustained-, pulsed-, controlled-, targeted and programmed release.

vii) Rectal/Intravaginal Administration

Compounds of the invention may be administered rectally or vaginally, for example, in the form of a suppository, pessary, or enema. Cocoa butter is a traditional suppository base, but various alternatives may be used as appropriate. Formulations for rectal/vaginal administration may be formulated to be immediate and/or modified release. Modified release formulations include delayed-, sustained-, pulsed-, controlled-, targeted and programmed release.

viii) Ocular Administration

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable {e.g. absorbable gel sponges, collagen) and nonbiodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

ix) Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

The amount of the active compound administered will be dependent on the subject being treated, the severity of the disorder or condition, the rate of administration, the disposition of the compound and the discretion of the prescribing physician. However, an effective dosage is typically in the range of 0.01-3000 mg, more preferably 0.5-1000 mg of active ingredient or the equivalent amount of a pharmaceutically acceptable salt thereof per day. Daily dosage may be administered in one or more treatments, preferably from 1 to 4 treatments, per day.

Preferably, the pharmaceutical compositions of the invention are made up in a form suitable for oral, inhalation or topical administration, being particularly preferred oral or inhalation administration.

The pharmaceutical formulations may conveniently be presented in unit dosage form and may be prepared by any of the methods well known in the art of pharmacy. Preferably the composition is in unit dosage form, for example a tablet, capsule or metered aerosol dose, so that the patient may administer a single dose.

The amount of each active which is required to achieve a therapeutic effect will, of course, vary with the particular active, the route of administration, the subject under treatment, and the particular disorder or disease being treated.

The following preparations forms are cited as formulation examples:

Formulation Example 1

Capsule for Oral Administration 50,000 capsules, each containing 100 mg of 3-(6-{[(1S)-1-(5-Fluoropyridin-2-yl)ethyl]amino}-7-methylimidazo[1,2-b]pyridazin-3-yl)pyridin-2(1H)-one (active ingredient), were prepared according to the following formulation:

| Active ingredient | 5 Kg |
| Lactose monohydrate | 10 Kg |
| Colloidal silicon dioxide | 0.1 Kg |
| Corn starch | 1 Kg |
| Magnesium stearate | 0.2 Kg |

Procedure

The above ingredients were sieved through a 60 mesh sieve, and were loaded into a suitable mixer and filled into 50,000 gelatine capsules.

Formulation Example 2

Tablet for Oral Administration 50,000 tablets, each containing 50 mg of 3-(6-{[(1S)-1-(5-Fluoropyridin-2-yl)ethyl]amino}-7-methylimidazo[1,2-b]pyridazin-3-yl)pyridin-2(1H)-one (active ingredient), are prepared from the following formulation:

| Active ingredient | 2.5 Kg |
| Microcrystalline cellulose | 1.95 Kg |
| Spray dried lactose | 9.95 Kg |
| Carboxymethyl starch | 0.4 Kg |
| Sodium stearyl fumarate | 0.1 Kg |
| Colloidal silicon dioxide | 0.1 Kg |

Procedure

All the powders are passed through a screen with an aperture of 0.6 mm, then mixed in a suitable mixer for 20 minutes and compressed into 300 mg tablets using 9 mm disc and flat bevelled punches.

Formulation Example 3

Oral Suspension

| Ingredient | Amount |
| --- | --- |
| Active Compound | 3 mg |
| Citric acid | 0.5 g |
| Sodium chloride | 2.0 g |
| Methyl paraben | 0.1 g |
| Granulated sugar | 25 g |
| Sorbitol (70% solution) | 11 g |
| Veegum K | 1.0 g |
| Flavoring | 0.02 g |
| Dye | 0.5 mg |
| Distilled water | q.s. to 100 mL |

Formulation Example 4

Hard Gelatine Capsule for Oral Administration

| Ingredient | Amount |
| --- | --- |
| Active Compound | 1 mg |
| Lactose | 150 mg |
| Magnesium stearate | 3 mg |

Formulation Example 5

Gelatin Cartridge for Inhalation

| Ingredient | Amount |
|---|---|
| Active Compound (micronized) | 0.2 mg |
| Lactose | 25 mg |

Formulation Example 6

Formulation for Inhalation with a DPI

| Ingredient | Amount |
|---|---|
| Active Compound (micronized) | 15 mg |
| Lactose | 3000 mg |

Formulation Example 7

Formulation for a MDI

| Ingredient | Amount |
|---|---|
| Active Compound (micronized) | 10 g |
| 1,1,1,2,3,3,3-heptafluoro-n-propane | q.s. to 200 mL |

In the formulation examples 3-7, active compound is 3-(6-{[(16)-1-(5-Fluoropyridin-2-yl)ethyl]amino}-7-methylimidazo[1,2-b]pyridazin-3-yl)pyridin-2(1H)-one.

Modifications, which do not affect, alter, change or modify the essential aspects of the compounds, combinations or pharmaceutical compositions described, are included within the scope of the present invention.

The invention claimed is:

1. A compound of Formula (I), or a pharmaceutically acceptable salt, stereoisomer, or tautomer thereof:

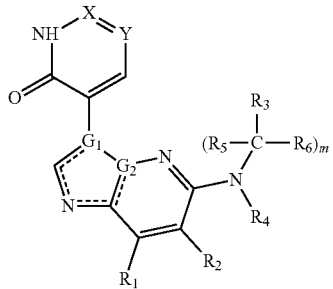

Formula (I)

wherein:
m is 0, 1, 2, or 3;
X is chosen from a nitrogen atom and a —$CR_7$ group;
Y is a —$CR_7$ group;
$G_1$ is a carbon atom;
$G_2$ is a nitrogen atom;
$R_1$ and $R_2$ are independently chosen from a hydrogen atom, a halogen atom, a hydroxy group, a cyano group, a linear or branched $C_1$-$C_6$ alkyl group, a $C_1$-$C_4$ haloalkyl group, a $C_1$-$C_4$ hydroxyalkyl group, a $C_3$-$C_{10}$ cycloalkyl group, a $C_3$-$C_{10}$ cycloalkenyl group, a monocyclic or polycyclic $C_5$-$C_{14}$ aryl group, a 5- to 14-membered heteroaryl group containing at least one heteroatom chosen from O, S and N, a 5- to 14-membered heterocyclyl group containing at least one heteroatom chosen from O, S and N,
wherein the alkyl, haloalkyl, hydroxyalkyl, cycloalkyl, cycloalkenyl, aryl, heteroaryl, and heterocyclyl groups are unsubstituted or substituted by one or more substituents chosen from a halogen atom, a cyano group, a linear or branched $C_1$-$C_6$ alkyl group, a $C_1$-$C_4$ haloalkyl group, a $C_1$-$C_4$ hydroxyalkyl group, a $C_1$-$C_4$ alkylsulfonyl group, a $C_3$-$C_7$ cycloalkyl group, a phenyl group, a pyridyl group, a pyrimidinyl group, and a piperidyl group;
or $R_1$ and $R_2$ are independently chosen from a —$(CH_2)_{0-2}OR_9$ group, a —O—$(CH_2)_{1-2}OR_9$ group, and a —$NR_8R_9$ group;
$R_3$ is chosen from a hydrogen atom, a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_{10}$ cycloalkyl group, a $C_3$-$C_{10}$ cycloalkenyl group, a monocyclic or polycyclic $C_5$-$C_{14}$ aryl group, a 5- to 14-membered heteroaryl group containing at least one heteroatom chosen from O, S and N, and a 5- to 14-membered heterocyclyl group containing at least one heteroatom chosen from O, S and N,
wherein the alkyl, haloalkyl, hydroxyalkyl, cycloalkyl, cycloalkenyl, aryl, heteroaryl, and heterocyclyl groups are unsubstituted or substituted by one or more substituents chosen from a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a phenyl group, a pyridyl group, a pyrimidinyl group, a piperidyl group, a —$(CH_2)_{0-2}OR_9$ group, a —$NR_8R_9$ group,
a —C(O)—$(CH_2)_{0-2}$—$R_6$ group, a —C(O)$(CH_2)_{0-2}$—$NR_6R_9$ group,
a —$S(O)_2(CH_2)_{0-2}R_9$ group, and a —$S(O)_2(CH_2)_{0-2}NR_8R_9$ group;
$R_4$ is chosen from a hydrogen atom, a $C_1$-$C_4$ haloalkyl group, a $C_1$-$C_4$ hydroxyalkyl group, and a linear or branched $C_1$-$C_6$ alkyl group, said alkyl group is unsubstituted or substituted by one or more substituents chosen from a cyano group, a $C_3$-$C_7$ cycloalkyl group, a phenyl group, a pyridyl group, a pyrimidinyl group, and a piperidyl group;
$R_5$ and $R_6$ are independently chosen from a hydrogen atom, a $C_1$-$C_4$ haloalkyl group, a $C_1$-$C_4$ hydroxyalkyl group, and a linear or branched $C_1$-$C_6$ alkyl group, said alkyl group is unsubstituted or substituted by one or more substituents chosen from a cyano group, a $C_3$-$C_7$ cycloalkyl group, a phenyl group, a pyridyl group, a pyrimidinyl group, and a piperidyl group;
$R_7$ is chosen from a hydrogen atom, a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_{10}$ cycloalkyl group, a $C_3$-$C_{10}$ cycloalkenyl group, a monocyclic or polycyclic $C_5$-$C_{14}$ aryl group, a 5- to 14-membered heteroaryl group containing at least one heteroatom chosen from O, S and N, and a 5- to 14-membered heterocyclyl group containing at least one heteroatom chosen from O, S and N,
wherein the alkyl, haloalkyl, hydroxyalkyl, cycloalkyl, cycloalkenyl, aryl, heteroaryl, and heterocyclyl groups are unsubstituted or substituted by one or more substituents chosen from a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl, a phenyl group, a pyridyl group, a pyrimidinyl group, and a piperidyl group;

$R_8$ is chosen from a hydrogen atom, a cyano group, a $C_1$-$C_4$ haloalkyl group, a $C_1$-$C_4$ hydroxyalkyl group or a linear or branched $C_1$-$C_6$ alkyl group, said alkyl group is unsubstituted or substituted by one or more substituents chosen from a cyano group, a $C_3$-$C_7$ cycloalkyl group, a phenyl group, a pyridyl group, a pyridinyl group, and a piperidyl group;

$R_9$ is chosen from a hydrogen atom, a $C_1$-$C_4$ haloalkyl group, a $C_1$-$C_4$ hydroxyalkyl group or a linear or branched $C_1$-$C_6$ alkyl group, said alkyl group is unsubstituted or substituted by one or more substituents chosen from a cyano group, a $C_3$-$C_7$ cycloalkyl group, a phenyl group, a pyridyl group, a pyrimidinyl group, and a piperidyl group.

2. The compound according to claim 1, wherein X is a nitrogen atom.

3. The compound according to claim 1, wherein X is a —$CR_7$ group.

4. The compound according to claim 1, wherein $R_1$ is chosen from a hydrogen atom, a halogen atom, a hydroxy group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a phenyl group, a 5- to 7-membered heteroaryl group containing one, two or three heteroatoms chosen from O, S and N, a 5 to 7-membered, a saturated N-containing heterocyclyl ring, said heterocyclyl ring is unsubstituted or substituted by one, two or three substituents chosen from a halogen atom, a cyano group, a linear or branched $C_1$-$C_4$ alkyl group, a $C_1$-$C_4$ alkylsulfonyl group, and a $C_3$-$C_7$ cycloalkyl group; or $R_1$ is chosen from a —$(CH_2)_{0-2}$$OR_9$ group, a —O—$(CH_2)_{1-2}$$OR_9$ group, and a —$NR_6R_9$ group.

5. The compound according to claim 1, wherein $R_2$ is chosen from a hydrogen atom, a halogen atom, a hydroxy group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a phenyl group, a 5- to 7-membered heteroaryl group containing one, two or three heteroatoms chosen from O, S and N, a 5- to 7-membered, saturated N-containing heterocyclyl ring, said heterocyclyl ring is unsubstituted or substituted by one, two or three substituents chosen from a halogen atom, a cyano group, a linear or branched $C_1$-$C_4$ alkyl group, a $C_1$-$C_4$ alkylsulfonyl group, and a $C_3$-$C_7$ cycloalkyl group; or $R_2$ is chosen from a —$(CH_2)_{0-2}$$OR_9$ group, a —O—$(CH_2)_{1-2}$$OR_9$ group, and a —$NR_8R_9$ group.

6. The compound according to claim 1, wherein $R_3$ is chosen from a linear or branched $C_1$-$C_8$ alkyl group, a $C_1$-$C_4$ haloalkyl group, a $C_1$-$C_4$ hydroxyalkyl group, a $C_3$-$C_7$ cycloalkyl group, a monocyclic or polycyclic $C_6$-$C_{14}$ aryl group, a 5- to 7-membered heteroaryl group containing one, two or three heteroatoms chosen from O, S and N, and a 5- to 7-membered heterocyclyl group containing one, two or three heteroatoms chosen from O, S and N, wherein the alkyl, haloalkyl, hydroxyalkyl, cycloalkyl, cycloalkenyl, aryl, heteroaryl, and heterocyclyl groups are unsubstituted or substituted by one or more substituents chosen from a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a phenyl group, a pyridyl group, a pyrimidinyl group, a piperidyl group, a —$(CH_2)_{0-2}$$OR_9$ group, a —$NR_8R_9$ group, a —C(O)—$(CH_2)_{0-2}$—$R_8$ group, a —C(O)—$(CH_2)_{0-2}$—$NR_8R_9$ group, a —$S(O)_2(CH_2)_{0-2}R_9$ group, and a —$S(O)_2(CH_2)_{0-2}NR_8R_9$ group.

7. The compound according to claim 6, wherein $R_3$ is chosen from a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a phenyl group, a pyridyl group, a pyrimidinyl group, and a piperidyl group, wherein the phenyl, pyridyl, pyrimidinyl or piperidyl groups are unsubstituted or substituted by one, two or three substituents chosen from a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl group, a phenyl group, a pyridyl group, a pyrimidinyl group, a piperidyl group, a —$(CH_2)_{0-2}$$OR_9$ group, a —$NR_8R_9$ group, a —C(O)—$(CH_2)_{0-2}$—$R_8$ group, a —C(O)—$(CH_2)_{0-2}$—$NR_8R_9$ group, a —$S(O)_2(CH_2)_{0-2}R_9$ group or a —$S(O)_2(CH_2)_{0-2}NR_8R_9$ group.

8. The compound according to claim 1, wherein $R_4$ is chosen from a hydrogen atom, a $C_1$-$C_4$ haloalkyl group, a $C_1$-$C_4$ hydroxyalkyl group, and a linear or branched $C_1$-$C_6$ alkyl group.

9. The compound according to claim 1, wherein $R_5$ and $R_6$ are independently chosen from a hydrogen atom, and a linear or branched $C_1$-$C_6$ alkyl group.

10. The compound according to claim 1, wherein $R_7$ is chosen from a hydrogen atom, a halogen atom, a cyano group, a linear or branched $C_1$-$C_4$ alkyl group, a $C_1$-$C_4$ haloalkyl group, a $C_1$-$C_4$ hydroxyalkyl group, a $C_3$-$C_7$ cycloalkyl group, a phenyl group, a naphthyl group, a pyridyl group, a pyrimidinyl group, and a piperidyl group, wherein the phenyl, naphthyl, pyridyl, pyrimidinyl or piperidyl groups are unsubstituted or substituted by one, two or three substituents chosen from a halogen atom, a cyano group, a linear or branched $C_1$-$C_6$ alkyl group, a $C_1$-$C_4$ haloalkyl group, a $C_1$-$C_4$ hydroxyalkyl group, a $C_3$-$C_7$ cycloalkyl, a phenyl group, a pyridyl group, a pyrimidinyl group, and a piperidyl group.

11. The compound according to claim 1, wherein the compound is of Formula (I-a):

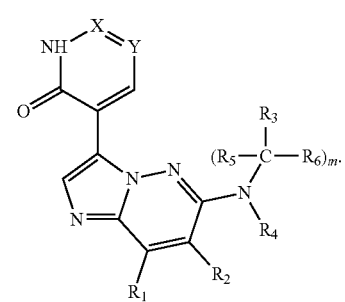

Formula (I-a)

12. The compound according to claim 1, wherein:
m is 0 or 1;
X is a nitrogen atom or a —$CR_7$ group;
Y is a —$CR_7$ group;
$G_1$ is a carbon atom;
$G_2$ is a nitrogen atom;
$R_1$ is chosen from a hydrogen atom, a halogen atom, a linear or branched $C_1$-$C_6$ alkyl group, a $C_3$-$C_7$ cycloalkyl group, a 5 to 7-membered, saturated N-containing heterocyclyl ring, said heterocyclyl ring is substituted by a $C_1$-$C_4$ alkylsulfonyl group, or $R_1$ is chosen from a —(CH$_2$)$_{0-2}$OR$_9$ group, a —O—(CH$_2$)$_{1-2}$OR$_9$ group, a —NR$_8$R$_9$ group, wherein R$_8$ and R$_9$ are independently chosen from a hydrogen atom and a linear or branched C$_1$-C$_3$ alkyl group;

R$_2$ is chosen from a hydrogen atom, a halogen atom, a linear or branched C$_1$-C$_6$ alkyl group, a C$_3$-C$_7$ cycloalkyl group, a —(CH$_2$)$_{0-2}$OR$_9$ group, a —O—(CH$_2$)$_{1-2}$OR$_9$ group, and a —NR$_8$R$_9$ group, wherein R$_3$ and R$_9$ are independently chosen from a hydrogen atom and a linear or branched C$_1$-C$_3$ alkyl group;

R$_3$ is chosen from a linear or branched C$_1$-C$_6$ alkyl group, a C$_1$-C$_4$ haloalkyl group, a C$_1$-C$_4$ hydroxyalkyl group, a C$_3$-C$_7$ cycloalkyl group, a monocyclic or polycyclic C$_6$-C$_{14}$ aryl group, a 5- to 7-membered heteroaryl group containing one, two or three heteroatoms selected from O, S and N, and a 5 to 7-membered heterocyclyl group containing one, two or three heteroatoms selected from O, S and N, wherein the alkyl, haloalkyl, hydroxyalkyl, cycloalkyl, aryl, heteroaryl, and heterocyclyl groups are unsubstituted or substituted by one, two or three substituents chosen from a halogen atom, a cyano group, a linear or branched C$_1$-C$_6$ alkyl group, a C$_1$-C$_4$ haloalkyl group, a C$_1$-C$_4$ hydroxyalkyl group, a C$_3$-C$_7$ cycloalkyl, a phenyl group, a pyridyl group, a pyrimidinyl group, a piperidyl group, a —(CH$_2$)$_{0-1}$OR$_9$ group, a —NR$_8$R$_9$ group, a —C(O)—(CH$_2$)$_{0-1}$—R$_8$ group, a —C(O)—(CH$_2$)$_{0-1}$—NR$_8$R$_9$ group, a —S(O)$_2$(CH$_2$)$_{0-1}$R$_9$, group, and a —S(O)$_2$(CH$_2$)$_{0-1}$NR$_8$R$_9$ group, wherein R$_8$ is a hydrogen atom, a cyano group, a linear or branched C$_1$-C$_3$ alkyl group, a C$_1$-C$_4$ haloalkyl group or a C$_3$-C$_7$ cycloalkyl group, and R$_9$ is chosen from a hydrogen atom and a linear or branched C$_1$-C$_3$ alkyl group;

R$_4$ is chosen from a hydrogen atom, a C$_1$-C$_4$ haloalkyl group, a C$_1$-C$_4$ hydroxyalkyl group, and a linear or branched C$_1$-C$_6$ alkyl group;

R$_5$ and R$_6$ are independently chosen from a hydrogen atom and a linear or branched C$_1$-C$_3$ alkyl group;

R$_7$ is chosen from a hydrogen atom, a halogen atom, a cyano group, a linear or branched C$_1$-C$_4$ alkyl group, a C$_1$-C$_4$ haloalkyl group, a C$_1$-C$_4$ hydroxyalkyl group, a C$_3$-C$_7$ cycloalkyl group, a phenyl group, a naphthyl group, a pyridyl group, a pyrimidinyl group, and a piperidyl group, wherein the phenyl, naphthyl, pyridyl, pyrimidinyl or piperidyl groups are unsubstituted or substituted by one, two or three substituents chosen from a halogen atom, a cyano group, a linear or branched C$_1$-C$_6$ alkyl group, a C$_1$-C$_4$ haloalkyl group, a C$_1$-C$_4$ hydroxyalkyl group, a C$_3$-C$_7$ cycloalkyl, a phenyl group, a pyridyl group, a pyrimidinyl group, and a piperidyl group.

13. The compound according to claim 12, wherein:
m is 0 or 1;
X is a nitrogen atom or a —CR$_7$ group;
Y is a —CR$_7$ group;
G$_1$ is a carbon atom;
G$_2$ is a nitrogen atom;
R$_1$ is chosen from a hydrogen atom, a halogen atom, a linear or branched C$_1$-C$_3$ alkyl group, and a 5- to 7-membered saturated N-containing heterocyclyl ring, said heterocyclyl ring is substituted by a C$_1$-C$_4$ alkylsulfonyl group; or R$_1$ is a —O—(CH$_2$)$_{1-2}$OR$_9$ group, wherein R$_9$ is a C$_1$-C$_3$ alkyl group;
R$_2$ is chosen from a hydrogen atom, a halogen atom, and a linear or branched C$_1$-C$_3$ alkyl group;

R$_3$ is chosen from a linear or branched C$_1$-C$_6$ alkyl group, a C$_1$-C$_4$ haloalkyl group, a C$_1$-C$_4$ hydroxyalkyl group, a C$_3$-C$_7$ cycloalkyl group, a phenyl group, a pyridyl group, a pyrimidinyl group, and a piperidinyl group, wherein the phenyl, pyridyl, pyrimidinyl or piperidinyl groups are unsubstituted or substituted by one or more substituents chosen from a halogen atom, a cyano group, a linear or branched C$_1$-C$_3$ alkyl group, a C$_1$-C$_4$ haloalkyl group, a C$_1$-C$_4$ hydroxyalkyl group, a C$_3$-C$_7$ cycloalkyl, and a —C(O)—(CH$_2$)$_{0-1}$—R$_8$ group, wherein R$_8$ is a cyano group, a linear or branched C$_1$-C$_3$ alkyl group, a C$_1$-C$_4$ haloalkyl group or a C$_3$-C$_7$ cycloalkyl group;

R$_4$ is chosen from a hydrogen atom and a methyl group;
R$_5$ and R$_6$ independently chosen from a hydrogen atom and a methyl group;
R$_7$ is chosen from a hydrogen atom, a halogen atom, a cyano group, a linear or branched C$_1$-C$_3$ alkyl group, a C$_1$-C$_4$ haloalkyl group, a C$_1$-C$_4$ hydroxyalkyl group, and a C$_3$-C$_7$ cycloalkyl group.

14. The compound according to claim 13, wherein:
m is 0 or 1;
X is a nitrogen atom or a —CR$_7$ group;
Y is a —CR$_7$ group;
G$_1$ is a carbon atom;
G$_2$ is a nitrogen atom;
R$_1$ is chosen from a hydrogen atom, a linear or branched C$_1$-C$_3$ alkyl group, and a 5- to 7-membered saturated N-containing heterocyclyl ring, said heterocyclyl ring is substituted by a C$_1$-C$_4$ alkylsulfonyl group; or R$_1$ is an —O—(CH$_2$)$_{1-2}$OR$_9$ group, wherein R$_9$ is a C$_1$-C$_3$ alkyl group;
R$_2$ is chosen from a hydrogen atom and a linear or branched C$_1$-C$_3$ alkyl group;
R$_3$ is chosen from a phenyl group, a pyridyl group, a pyrimidinyl group, and a piperidinyl group, wherein the phenyl, pyridyl, pyrimidinyl and piperidinyl groups are unsubstituted or substituted by one or more substituents chosen from a halogen atom and a —C(O)—(CH$_2$)$_{0-1}$—R$_8$ group, wherein R$_8$ is a cyano group;

R$_4$ is a hydrogen atom;
R$_5$ and R$_6$ are independently chosen from a hydrogen atom and a methyl group;
R$_7$ is chosen from a hydrogen atom, a halogen atom, a linear or branched C$_1$-C$_3$ alkyl group, and a C$_1$-C$_4$ haloalkyl group.

15. The compound according to claim 1 chosen from:
3-Oxo-3-((3R)-3-{[3-(2-oxo-1,2-dihydropyridin-3-yl)imidazo[1,2-b]pyridazin-6-yl]amino}piperidin-1-yl)propanenitrile;
3-(6-{[(1S)-1-Phenylethyl]amino}imidazo[1,2-b]pyridazin-3-yl)pyridin-2(1H)-one;
3-(6-{[(1S)-1-(5-Fluoropyridin-2-yl)ethyl]amino}imidazo[1,2-b]pyridazin-3-yl)pyridin-2(1H)-one;
3-(6-{[(1R)-(5-Fluoropyridin-2-yl)ethyl]amino}imidazo[1,2-b]pyridazin-3-yl)pyridin-2(1H)-one;
3-(6-{[(1S)-1-(5-Fluoropyrimidin-2-yl)ethyl]amino}imidazo[1,2-b]pyridazin-3-yl)pyridin-2(1H)-one;
4-(6-{[(1S)-1-Phenylethyl]amino}imidazo[1,2-b]pyridazin-3-yl)pyridazin-3(2H)-one;
5-Fluoro-3-(6-{[(1S)-1-(5-fluoropyridin-2-yl)ethyl]amino}imidazo[1,2-b]pyridazin-3-yl)pyridin-2(1H)-one;

5-Chloro-3-(6-{[(1S)-1-(5-fluoropyridin-2-yl)ethyl] amino}imidazo[1,2-b]pyridazin-3-yl)pyridin-2(1H)-one;

3-(6-{[(1S)-1-(5-Fluoropyridin-2-yl)ethyl]amino}-7-methylimidazo[1,2-b]pyridazin-3-yl)pyridin-2(1H)-one;

5-Fluoro-3-(6-{[(1S)-1-(5-fluoropyridin-2-yl)ethyl] amino}-7-methylimidazo[1,2-b]pyridazin-3-yl)pyridin-2(1H)-one;

(S)-5-fluoro-3-(6-(1-(5-fluoropyrimidin-2-yl)ethylamino) imidazo[1,2-b]pyridazin-3-yl)pyridin-2(1H)-one;

(S)-5-(difluoromethyl)-3-(6-(1-(5-fluoropyridin-2-yl) ethylamino)imidazo[1,2-b]pyridazin-3-yl)pyridin-2 (1H)-one;

(S)-3-(6-(1-(5-fluoropyridin-2-yl)ethylamino)imidazo[1, 2-b]pyridazin-3-yl)-5-methylpyridin-2(1H)-one;

(S)-3-(6-(1-(5-fluoropyridin-2-yl)ethylamino)-8-(2-methoxyethoxyl)imidazo[1,2-b]pyridazin-3-yl)pyridin-2 (1H)-one;

(S)-3-(6-(1-(5-fluoropyridin-2-yl)ethylamino)-8-(4-(methylsulfonyl)piperazin-1-yl)imidazo[1,2-b]pyridazin-3-yl)pyridin-2(1H)-one;

(S)-3-(6-(1-(5-fluoropyrimidin-2-yl)ethylamino)-7-methylimidazo[1,2-b]pyridazin-3-yl)pyridin-2(1H)-one; and (S)-5-fluoro-3-(6-(1-(5-fluoropyrimidin-2-yl)ethylamino)-7-methylimidazo[1,2-b]pyridazin-3-yl)pyridin-2(1H)-one;

or a pharmaceutically acceptable salt, stereoisomer, or tautomer thereof.

16. A pharmaceutical composition comprising the compound according to claim 1 and a pharmaceutically acceptable diluent or carrier.

17. A combination product comprising (i) the compound according to claim 1; and (ii) at least one additional compound chosen from:

a) Dyhydrofolate reductase inhibitors;
b) Dihydroorotate dehydrogenase (DHODH) inhibitors;
c) Immunomodulators;
d) Inhibitors of DNA synthesis and repair;
e) Immunosuppressants;
f) Anti-alpha 4 integrin antibodies;
g) Corticoids and glucocorticoids;
h) Fumaric acid esters;
i) Anti-tumor necrosis factor-alpha (Anti-TNF-alpha;
j) Soluble Tumor necrosis factor-alpha (TNF-alpha) receptors;
k) Anti-CD20 (lymphocyte protein) monoclonal antibodies;
l) Anti-CD52 (lymphocyte protein) monoclonal antibodies;
m) Anti-CD25 (lymphocyte protein);
n) Anti-CD88 (lymphocyte protein;
o) Anti-Interleukin 6 Receptor (IL-6R);
p) Anti-Interleukin 12 Receptor (IL-12R)/Interleukin 23 Receptor (IL-23R);
q) Calcineurin inhibitors;
r) inosine-monophosphate dehydrogenase (IMPDH) inhibitors;
s) Cannabinoid receptor agonists;
t) Chemokine CCR1 antagonists;
u) Chemokine CCR2 antagonists;
v) Necrosis factor-kappaB (NF-kappaB or NFKB) Activation Inhibitors;
w) Adenosine $A_{2A}$ agonists;
x) Sphingosine-1 (S1P) phosphate receptor agonists;
y) Sphingosine-1 (S1P) Base inhibitors;
z) Spleen tyrosine kinase (Syk) inhibitors;
aa) Protein Kinase Inhibitors (PKC) inhibitors;
bb) Anti-cholinergic agents;
cc) Beta adrenergic agonists;
dd) Compounds having bifunctional Muscarinic Antagonist-Beta2 Agonist activity (MABAs);
ee) Histamine 1 (H1) receptor antagonists;
ff) Chemoattractant receptor homologous molecule expressed on $TH_2$ cells (CRTH2) inhibitors;
gg) Vitamin D derivatives;
hh) Anti-inflammatory agents;
ii) Anti-allergic agents;
jj) Anti-viral agents;
kk) Phosphodiesterase (PDE) III inhibitors;
ll) Phosphodiesterase (PDE) IV inhibitors;
mm) Dual Phosphodiestearase (PDE) III/IV inhibitors;
nn) Xanthine derivatives;
oo) p38 Mitogen-Activated Protein Kinase (p38 MAPK) Inhibitors;
pp) Mitogen-activated extracellular signal regulated kinase kinase (MEK) inhibitor;
qq) Phosphoinositide 3-Kinases (PI3Ks) inhibitors;
rr) Interferons comprising Interferon beta 1a; and
ss) Interferon alpha;

for simultaneous, separate or sequential use in the treatment of the human or animal body.

18. The compound according to claim 4, wherein $R_1$ is chosen from a hydrogen atom, a halogen atom, a linear or branched $C_1$-$C_6$ alkyl group, a $C_3$-$C_7$ cycloalkyl group, and a 5- to 7-membered saturated N-containing heterocyclyl ring, said heterocyclyl ring is substituted by one two or three substituents chosen from a halogen atom, a cyano group, a linear or branched $C_1$-$C_4$ alkyl group, a $C_1$-$C_4$ alkylsulfonyl group, and a $C_3$-$C_7$ cycloalkyl group; or $R_1$ is chosen from a —$(CH_2)_{0-2}OR_9$ group, a —O—$(CH_2)_{1-2}OR_9$ group, and a —$NR_8R_9$ group, wherein $R_8$ and $R_9$ are independently chosen from a hydrogen atom and a linear or branched $C_1$-$C_3$ alkyl group.

19. The compound according to claim 4, wherein $R_1$ is chosen from a hydrogen atom, a linear or branched $C_1$-$C_3$ alkyl group, and a 5- to 7-membered saturated N-containing heterocyclyl ring, said heterocyclyl ring is substituted by a $C_1$-$C_4$ alkylsulfonyl group; or $R_1$ is chosen from a —O—$(CH_2)_{1-2}OR_9$ group and a —$NR_8R_9$ group, wherein $R_6$ and $R_9$ are independently chosen from a hydrogen atom and a linear or branched $C_1$-$C_3$ alkyl group.

20. The compound according to claim 4, wherein $R_1$ chosen from a hydrogen atom and a methyl group.

21. The compound according to claim 5, wherein $R_2$ is chosen from a hydrogen atom, a halogen atom, a linear or branched $C_1$-$C_6$ alkyl group, a $C_3$-$C_7$ cycloalkyl group, a —$(CH_2)_{0-2}OR_9$ group, a —O—$(CH_2)_{1-2}OR_9$ group, and a —$NR_8R_9$ group,
wherein $R_8$ and $R_9$ are independently chosen from a hydrogen atom and a linear or branched $C_1$-$C_3$ alkyl group.

22. The compound according to claim 5, wherein $R_2$ is chosen from a hydrogen atom, a halogen atom, a linear or branched $C_1$-$C_3$ alkyl group, and a —$NR_8R_9$ group, wherein $R_8$ and $R_9$ are independently chosen from a hydrogen atom and a linear or branched $C_1$-$C_3$ alkyl group.

23. The compound according to claim 5, wherein $R_2$ is chosen from a hydrogen atom and a methyl group.

24. The compound according to claim 8, wherein $R_4$ is chosen from a hydrogen atom, a $C_1$-$C_2$ haloalkyl group, a $C_1$-$C_2$ hydroxyalkyl group, and a linear or branched $C_1$-$C_3$ alkyl group.

25. The compound according to claim 8, wherein $R_4$ is chosen from a hydrogen atom and a linear or branched $C_1$-$C_3$ alkyl group.

26. The compound according to claim 8, wherein $R_4$ is chosen a hydrogen atom or a methyl group.

27. The compound according to claim 9, wherein $R_5$ and $R_6$ are independently chosen from a hydrogen atom and a linear or branched $C_1$-$C_3$ alkyl group.

28. The compound according to claim 9, wherein $R_5$ and $R_6$ are independently chosen from a hydrogen atom or a methyl group.

\* \* \* \* \*